United States Patent
Reedtz-Runge et al.

(10) Patent No.: US 10,195,255 B2
(45) Date of Patent: Feb. 5, 2019

(54) GLP-1 DERIVATIVES AND USES THEREOF

(71) Applicant: Novo Nordisk A/S, Bagsvaerd (DK)

(72) Inventors: Steffen Reedtz-Runge, Bikeroed (DK); Per Sauerberg, Farum (DK); Jacob Kofoed, Vaerloese (DK); Ingrid Pettersson, Frederiksberg (DK); Christian W. Tornoee, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 172 days.

(21) Appl. No.: 14/897,738

(22) PCT Filed: Jun. 19, 2014

(86) PCT No.: PCT/EP2014/062952
§ 371 (c)(1),
(2) Date: Dec. 11, 2015

(87) PCT Pub. No.: WO2014/202727
PCT Pub. Date: Dec. 24, 2014

(65) Prior Publication Data
US 2016/0143998 A1    May 26, 2016

Related U.S. Application Data

(60) Provisional application No. 61/841,995, filed on Jul. 2, 2013, provisional application No. 61/845,647, filed on Jul. 12, 2013.

(30) Foreign Application Priority Data

Jun. 20, 2013 (EP) .................................. 13173068
Jul. 4, 2013 (EP) .................................. 13175092

(51) Int. Cl.
| A61K 47/54 | (2017.01) |
| A61K 47/56 | (2017.01) |
| A61K 47/60 | (2017.01) |
| A61K 38/26 | (2006.01) |
| C07K 14/605 | (2006.01) |

(52) U.S. Cl.
CPC .............. *A61K 38/26* (2013.01); *A61K 47/54* (2017.08); *A61K 47/542* (2017.08); *A61K 47/56* (2017.08); *A61K 47/60* (2017.08); *C07K 14/605* (2013.01)

(58) Field of Classification Search
CPC ...... A61K 38/26; A61K 47/542; A61K 47/56; A61K 47/54; A61K 47/60; A61K 47/48038; A61K 47/48215; C07K 14/605
See application file for complete search history.

(56) References Cited

U.S. PATENT DOCUMENTS

| 9,006,178 B2 * | 4/2015 | Kofoed | ................ | A61K 47/542 514/7.2 |
| 2006/0014241 A1 * | 1/2006 | Glaesner | .............. | C07K 14/605 435/69.1 |
| 2008/0207507 A1 | 8/2008 | Lau et al. | | |
| 2010/0261637 A1 | 10/2010 | Spetzler et al. | | |
| 2011/0166321 A1 | 7/2011 | Garibay et al. | | |
| 2013/0116173 A1 * | 5/2013 | DiMarchi | ............ | C07K 14/605 514/5.3 |
| 2013/0143798 A1 | 6/2013 | Lau et al. | | |
| 2013/0244931 A1 | 9/2013 | Lau et al. | | |
| 2013/0288958 A1 | 10/2013 | Lau et al. | | |
| 2013/0288960 A1 | 10/2013 | Madsen et al. | | |
| 2014/0088005 A1 | 3/2014 | Wieczorek et al. | | |
| 2014/0179899 A1 | 6/2014 | Garibay et al. | | |
| 2017/0320927 A1 | 11/2017 | Sauerberg et al. | | |
| 2018/0258153 A1 | 9/2018 | Kofoed | | |

FOREIGN PATENT DOCUMENTS

| EP | 1060191 A1 | 12/2000 |
| WO | 200055119 A1 | 9/2000 |
| WO | 200135988 A1 | 5/2001 |
| WO | 0215981 A1 | 2/2002 |
| WO | 2004/093823 A2 | 11/2004 |
| WO | 2005/027978 A2 | 3/2005 |

(Continued)

OTHER PUBLICATIONS

Deacon et al., Diabetologia (1998) 41: 271±278, Summary,teach GLP-1 having N-terminally substitutions with threonine, glycine, serine or a-aminoisobutyric acid, and show improvements in half-life that they attribute to less degradation by dipeptidyl peptidase IV.*

(Continued)

*Primary Examiner* — Karlheinz R. Skowronek
*Assistant Examiner* — Joseph Fischer
(74) *Attorney, Agent, or Firm* — Jianjie Hu

(57) ABSTRACT

The invention relates to a derivative of a GLP-1 analogue, optionally C-terminally extended, which derivative comprises a first and a second protracting moiety in the form of a C20 or C22 diacid radical, a bis-amino branched linker, and a first and a second further linker each comprising an OEG-like linker element; wherein these elements are interconnected via amide bonds and attached to a Lys residue of the GLP-1 analogue. The invention also relates to intermediate products in the form of novel GLP-1 analogues incorporated in the derivatives of the invention, as well pharmaceutical compositions and medical uses of the derivatives. The derivatives have very long half-lives while maintaining a satisfactory potency, which makes them potentially suitable for once-monthly administration.

12 Claims, 1 Drawing Sheet
Specification includes a Sequence Listing.

(56) References Cited

FOREIGN PATENT DOCUMENTS

| WO | WO2005/02798 | * | 3/2005 | ............. A61K 47/48 |
|----|--------------|---|--------|--------------------------|
| WO | WO-2005027978 A2 | * | 3/2005 | ............. A61K 38/26 |
| WO | 2006/037810 | | 4/2006 | |
| WO | 2006097537 A2 | | 9/2006 | |
| WO | 2006124529 A1 | | 11/2006 | |
| WO | 2009/030738 A1 | | 3/2009 | |
| WO | 2009/030771 A1 | | 3/2009 | |
| WO | 2010/142665 A1 | | 12/2010 | |
| WO | 2011/080103 A1 | | 7/2011 | |
| WO | 2012/012352 A2 | | 1/2012 | |
| WO | 2012062803 A1 | | 5/2012 | |
| WO | 2012140117 A1 | | 10/2012 | |
| WO | 2012177929 A2 | | 12/2012 | |
| WO | 2013/167454 A1 | | 11/2013 | |
| WO | 2014202727 A1 | | 12/2014 | |
| WO | 2015000942 A1 | | 1/2015 | |

OTHER PUBLICATIONS

Knudsen L. B. et al., Potent Derivatives of Glucagon-like Peptide-1 with Pharmacokinetic Properties Suitable for Once Daily Administration, Journal of Medical Chemistry, 2000, vol. 43, No. 9, 1664-1669.

* cited by examiner

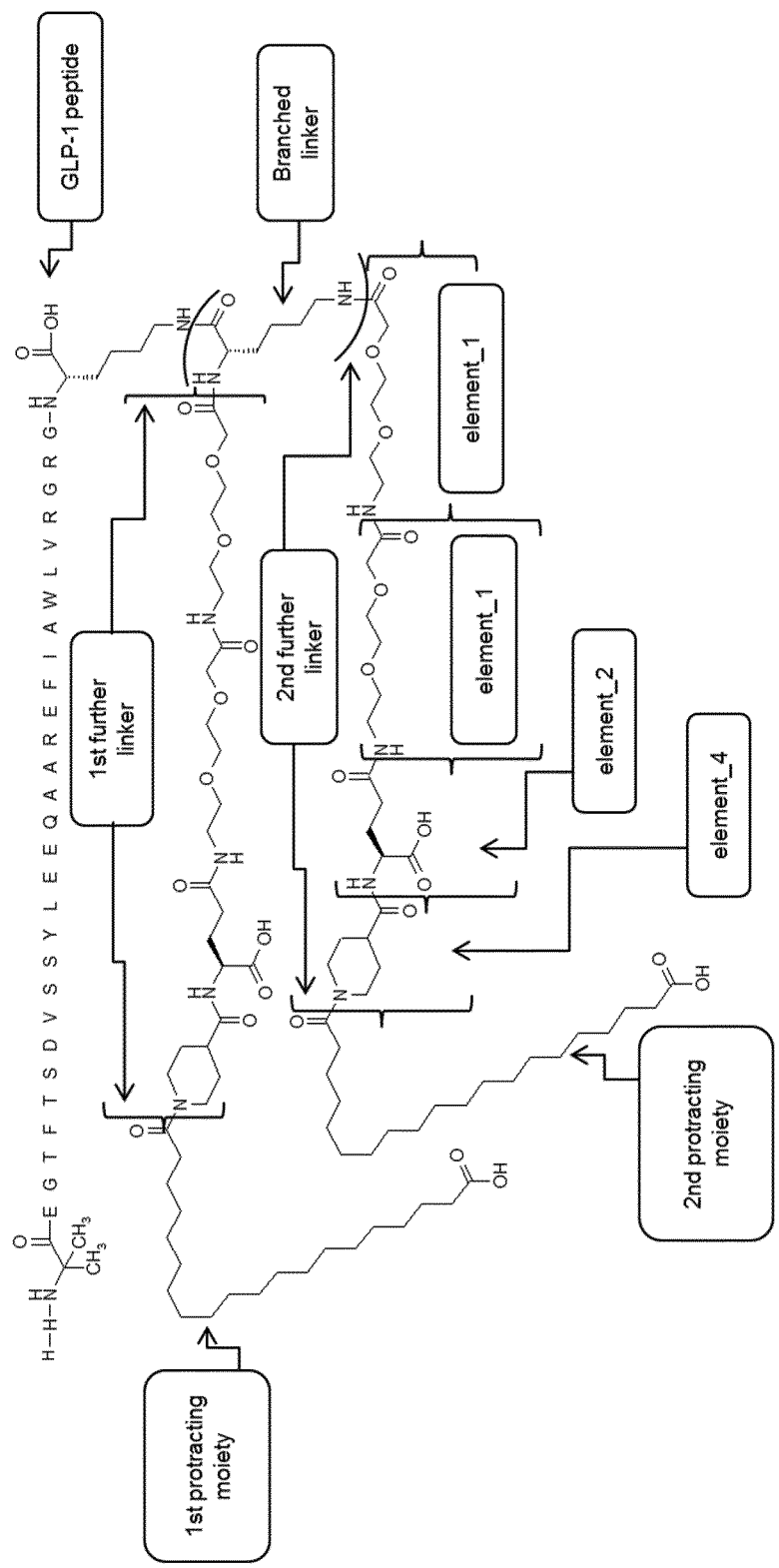

GLP-1 DERIVATIVES AND USES THEREOF

CROSS-REFERENCE TO RELATED APPLICATIONS

This application is a 35 U.S.C. § 371 National Stage application of International Application PCT/EP2014/062952(WO 2014/202727), filed Jun. 19, 2014, which claimed priority of European Patent Application 13175092.9, filed Jul. 4, 2013 and European Patent Application 13173068.1, filed Jun. 20, 2013 and of U.S. Provisional Application 61/845,647; filed Jul. 12, 2013 and U.S. Provisional Application 61/841,995 filed Jul. 2, 2013; the contents of which are incorporated herein by reference.

TECHNICAL FIELD

The present invention relates to derivatives of analogues of glucagon-like peptide 1 (GLP-1), more in particular to GLP-1 derivatives with a branched acylation, and their pharmaceutical use.

SEQUENCE LISTING

The instant application contains a Sequence Listing which has been submitted in ASCII format via EFS-Web and is hereby incorporated by reference in its entirety. Said ASCII copy, created on Nov. 18, 2015, is named 8705_SeqList.txt and is 9,213 bytes in size.

BACKGROUND

WO 2005/027978 A2 discloses a number of GLP-1 derivatives including some with a branched acylation of C12 or C14 fatty acids.

WO 2009/030771 A1 discloses a number of mono-acylated GLP-1 derivatives including some that are acylated with C20 fatty diacids, via various combinations of linker elements.

WO 2012/062803 A1 discloses a number of double-acylated GLP-1 derivatives including some that are acylated with C18 fatty diacids.

SUMMARY

Liraglutide is a GLP-1 derivative for once daily administration. It is marketed under the trade name of VICTOZA® by Novo Nordisk A/S.

Semaglutide is a GLP-1 derivative for once weekly administration. It is under development by Novo Nordisk A/S. This compound is disclosed in WO 2006/097537 Example 4.

The invention relates to GLP-1 derivatives which have potential for once-monthly administration.

In one aspect the invention relates to a derivative of a GLP-1 analogue which is acylated at a Lys residue with two acyl chains, via one and the same bis-amino linker (also called a branched linker). The GLP-1 analogue may be C-terminally extended as compared to native GLP-1. Each of the acyl chains is made up of two long fatty diacids, that are connected to the branched linker via a further linker which comprises a linker element of the OEG-type (amino-dioxa-carboxylic acid), and optionally additional linker elements.

In a second aspect the invention relates to pharmaceutical compositions comprising such derivatives and pharmaceutically acceptable excipients, as well as the medical use of the derivatives.

In a third aspect, the invention relates to intermediate products in the form of novel GLP-1 analogues, which can be incorporated in the GLP-1 derivatives of the invention. Such analogues may comprise the following amino acid changes when compared to GLP-1 (7-37) (SEQ ID NO: 1): iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii) (8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), or xvii) (8Aib, 22E, 26R, 34R, 37P, 38K) (SEQ ID NO: 18).

The amino acid sequence of native human GLP-1(7-37) is included in the sequence listing as SEQ ID NO: 1. SEQ ID NO's 2-18 are specific GLP-1 analogues of the GLP-1 derivatives of the invention, and SEQ ID NO: 19 is a GLP-1 analogue which is incorporated in two comparative compounds.

The derivatives of the invention represent a remarkable leap in the search for GLP-1 derivatives of very long half-lives and still with a very good potency.

BRIEF DESCRIPTION OF DRAWINGS

The structure of the derivatives of the invention is explained in more detail in the drawings, where FIG. 1 shows the structure of the derivative of Example 18 with added boxes and lines showing the terminology used herein for the various parts of the molecule.

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in μM=uM.

An asterisk (*) in a chemical formula designates i) a point of attachment, ii) a radical, and/or iii) an unshared electron.

In its first aspect the invention relates to a derivative of a GLP-1 peptide, wherein the GLP-1 peptide is of formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$, wherein Xaa$_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, α-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Lys, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg or Lys; Xaa$_{27}$ is Glu, Lys, or Leu; Xaa$_{30}$ is Ala, Glu, or Arg; Xaa$_{31}$ is Trp or His; Xaa$_{33}$ is Val, Lys, or Arg; Xaa$_{34}$ is Arg, Lys, His, Asn, or Gln; Xaa$_{35}$ is Gly or Ala; Xaa$_{36}$ is Arg or Gly; Xaa$_{37}$ is Gly, Pro, or Lys; Xaa$_{38}$ is Ser, Gly, Ala, Glu, Pro, Lys, or absent; Xaa$_{39}$ is Ser, Gly, Ala, Glu, Pro, Lys, or absent; Xaa$_{40}$ is Ser, Gly, Ala, Glu, Pro, Lys, or absent; Xaa$_{41}$ is Ser, Gly, Ala, Glu, Pro, Lys, or absent; Xaa$_{42}$ is Ser, Gly, Ala, Glu, Pro, Lys, or absent; and Xaa$_{43}$ is Ser, Gly, Ala, Glu, Pro, Lys, or absent; which GLP-1 peptide comprises a Lys residue at a position corresponding to position 27, 37, 38, 39, 40, 41, 42, or 43 of GLP-1(7-37) (SEQ ID NO: 1); which derivative comprises a first and a second protracting moiety selected from Chem. 1 and Chem. 1a:

HOOC—(CH$_2$)$_{18}$—CO—*, and         Chem. 1:

HOOC—(CH$_2$)$_{20}$—CO—*;         Chem. 1a:

a branched linker of formula Chem. 2:

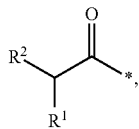

wherein R$^1$ is —(CH$_2$)$_q$—NH—*, wherein q is an integer in the range of 0-5, R$^2$ is —(CH$_2$)$_w$—NH—*, wherein w is an integer in the range of 0-5, with the provisos that when w is 0 q is an integer in the range of 1-5, and when q is 0 w is an integer in the range of 1-5; and a first and a second further linker, each comprising an element_1 of formula Chem. 3:

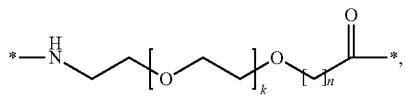

wherein k is an integer in the range of 1-15, and n is an integer in the range of 1-5; wherein the first protracting moiety is attached at its *—CO end to a first *—NH end of the branched linker, via the first further linker, the second protracting moiety is attached at its *—CO end to a second *—NH end of the branched linker, via the second further linker; and the branched linker is attached at its *—CO end to the epsilon amino group of the Lys residue of the GLP-1 peptide; or a pharmaceutically acceptable salt, amide, or ester thereof.

In its second aspect, the invention relates to a pharmaceutical composition comprising a derivative of the invention and a pharmaceutically acceptable excipient; and the use of the derivative or analogue of the invention as a medicament, in particular for use in the (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

In its third aspect, the invention relates to an intermediate product in the form of a GLP-1 analogue, which comprises the following amino acid changes when compared to GLP-1 (7-37) (SEQ ID NO: 1):

iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii)

(8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), or xvii) (8Aib, 22E, 26R, 34R, 37P, 38K) (SEQ ID NO: 18); or which is selected from the following analogues of GLP-1 (7-37) (SEQ ID NO: 1):

i) (8Aib, 22E, 26R, 27K, 34R) (SEQ ID NO: 10), iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii) (8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), and xvii) (8Aib, 22E, 26R, 34R, 37P, 38K) (SEQ ID NO: 18).

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

Structural Features

GLP-1 Peptides and Analogues

The term "GLP-1 peptide" as used herein refers to an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 peptide of the invention may be defined by the following formula I: $Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$, wherein $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, α-methyl-histidine, 3-pyridylalanine, 2-pyridylalanine, or 4-pyridylalanine; $Xaa_8$ is Ala, Gly, Ser, Aib, (1-aminocyclopropyl) carboxylic acid, or (1-aminocyclobutyl) carboxylic acid; $Xaa_{12}$ is Phe or Leu; $Xaa_{16}$ is Val or Leu; $Xaa_{18}$ is Ser, Val, Lys, Arg, or Leu; $Xaa_{19}$ is Tyr or Gln; $Xaa_{20}$ is Leu or Met; $Xaa_{22}$ is Gly or Glu; $Xaa_{23}$ is Gln, Glu, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Arg; $Xaa_{31}$ is Trp or His; $Xaa_{33}$ is Val, Lys, or Arg; $Xaa_{34}$ is Arg, Lys, His, Asn, or Gln; $Xaa_{35}$ is Gly or Ala; $Xaa_{36}$ is Arg or Gly; $Xaa_{37}$ is Gly, Pro, or Lys; $Xaa_{38}$ is Ser, Gly, Ala, Glu, Pro, Lys, or absent; $Xaa_{39}$ is Ser, Gly, Ala, Glu, Pro, Lys, or absent; $Xaa_{40}$ is Ser, Gly, Ala, Glu, Pro, Lys, or absent; $Xaa_{41}$ is Ser, Gly, Ala, Glu, Pro, Lys, or absent; $Xaa_{42}$ is Ser, Gly, Ala, Glu, Pro, Lys, or absent; and $Xaa_{43}$ is Ser, Gly, Ala, Glu, Pro, Lys, or absent; wherein a Lys residue is present at a position corresponding to position 27, 37, 38, 39, 40, 41, 42, or 43 of GLP-1(7-37) (SEQ ID NO: 1).

In this formula the numbering of the amino acid residues follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue, which in native GLP-1 is Gly with number 37, however the peptide of formula I may have a C-terminal tail or extension, as defined in the formula, up to and including position 43.

The numbering is done differently in the sequence listing, where the first amino acid residue of SEQ ID NO: 1 (His) is assigned no. 1, and the last (Gly) no. 31. However, herein we follow the established numbering practice in the art, as explained above.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1). These changes may represent, independently, one or more amino acid substitutions, additions, and/or deletions.

The following are non-limiting examples of suitable analogue nomenclature.

The GLP-1 analogue incorporated in the derivative of Example 20 herein may be referred to as (8Aib, 22E, 26R, 27K, 34R) GLP-1(7-37). When this Example 20 analogue is aligned with native GLP-1, the amino acid at the position in the analogue which corresponds, according to the alignment, to position 8 in native GLP-1 is Aib, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 27 in native GLP-1 is K, and the amino acid at the position in the analogue which corresponds to position 34 in native GLP-1 is R. All other amino acids in this analogue are identical to the corresponding amino acid in native GLP-1.

As another example the GLP-1 analogue which is incorporated in the derivative of Example 2 herein may be referred to as (8Aib, 22E, 26R, 34R, 38G, 39G, 40S, 41K) GLP-1(7-37). This is to be understood similarly as described above for the amino acids at those positions in the analogue which correspond to positions 8, 22, 26, and 34 of native GLP-1, i.e. as kind of substitutions, when compared to native GLP-1. The subsequent designations are to be understood as kind of C-terminal additions, when compared to native GLP-1. For example, 38G refers to the amino acid G being found at the C-terminus of the peptide, at the position next to the position which corresponds to position 37 in native GLP-1, when the analogue is aligned with native GLP-1. And then follows at the next position C-terminally also a G at the position in the analogue which would correspond to position 39 of native GLP-1; and an S at the subsequent position C-terminally, in the position in the analogue which would correspond to position 40 of native GLP-1; and lastly a K at the position which would correspond to position 41 of native GLP-1.

The general formula I is to be understood in a similar manner.

Analogues "comprising" certain specified changes may comprise further changes, when compared to SEQ ID NO: 1. In a particular embodiment, the analogue "has" the specified changes.

As is apparent from the above examples, amino acid residues may be identified by their full name, their one-letter code, and/or their three-letter code. These three ways are fully equivalent.

The expressions "a position equivalent to" or "corresponding position" may be used to characterise the site of change in a variant GLP-1(7-37) sequence by reference to a reference sequence such as native GLP-1(7-37) (SEQ ID NO: 1). Equivalent or corresponding positions, as well as the number of changes, are easily deduced, e.g. by simple handwriting and eyeballing; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below, in which sequence no. 1 is SEQ ID NO: 1, and sequence no. 2 is the analogue (8Aib, 22E, 26R, 34R, 38S, 39S, 40G, 41A, 42P, 43K) thereof:

```
# Aligned sequences: 2

1: 1

2: 2

Matrix: EBLOSUM62

Gap_penalty: 10.0

Extend_penalty: 0.5

Length: 37

Identity:      27/37 (73.0%)

Similarity:    29/37 (78.4%)

Gaps:           6/37 (16.2%)

Score: 143.0

1      1 HAEGTFTSDVSSYLEGQAAKEFIAWLVKGRG------   31
         |.||||||||||||.|||:|||||||:|||
2      1 HXEGTFTSDVSSYLEEQAAREFIAWLVRGRGSSGAPK   37
```

When 6 is added to the position numbers shown in this alignment (i.e., to "1" and "31" in sequence 1, and to "1" and "37" in sequence 2) one gets the position numbering as used herein. For example, in sequence 1 (which is identical to SEQ ID NO: 1), the N-terminal amino acid (H) has position number 7, and the C-terminal amino acid (G) has number 37.

Regarding sequence 2, the N-terminal amino acid (H) has number 7 and the C-terminal amino acid (K) has number 43.

In case specific amino acid residues or the like with no one-letter codon (such as Aib) are included in the sequence these may, for alignment purposes, be replaced with, e.g., X, as shown in the above alignment. If desired, X can later be manually corrected. The following are non-limiting examples of what can be inferred from the above alignment:

As one example it can be inferred that sequence 2 has 10 amino acid changes as compared to sequence 1 (namely at all those positions where a full stop ("."), a colon (":"), or a horizontal hyphen ("-") is shown in the alignment).

As another example it can be inferred that, e.g., sequence no. 2 comprises 38S, since it has an S at the position which corresponds, according to the alignment, to position 38 in the reference sequence (sequence 1, SEQ ID NO: 1).

And similarly all other changes in sequence 2 as compared to sequence 1 can be deduced from the alignment.

The term "peptide", as e.g. used in the context of the GLP-1 analogues of the derivatives of the invention, refers to a compound which comprises a series of amino acids interconnected by amide (or peptide) bonds.

The peptides of the invention comprise at least i) 31, ii) 32, iii) 33, iv) 34, v) 35, vi) 36, or vii) 37 amino acids.

In particular embodiments, the peptide is composed of i) 31, ii) 32, iii) 33, iv) 34, v) 35, vi) 36, or vii) 37 amino acids.

In additional particular embodiments, the peptide consists of i) 31, ii) 32, iii) 33, iv) 34, v) 35, vi) 36, or vii) 37 amino acids.

In a still further particular embodiment the peptide consists of amino acids interconnected by peptide bonds.

Amino acids are molecules containing an amine group and a carboxylic acid group, and, optionally, one or more additional groups, often referred to as a side chain.

The term "amino acid" includes proteinogenic (or natural) amino acids (amongst those the 20 standard amino acids), as well as non-proteinogenic (or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid, or 2-Aminoisobutyric acid), desaminohistidine (alternative name imidazopropionic acid or 3-(Imidazol-5-yl)propanoic acid, abbreviated Imp), as well as the D-isomers of the proteinogenic amino acids.

In what follows, all amino acids of the GLP-1 peptide for which the optical isomer is not stated is to be understood to mean the L-isomer (unless otherwise specified).

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 35, 36, 38, or 39 herein.

GLP-1 Derivatives

The term "derivative" as used herein in the context of a GLP-1 peptide or analogue means a chemically modified GLP-1 peptide, in which one or more substituents have been covalently attached to the peptide. The substituent may also be referred to as a side chain. In a particular embodiment the side chain of the derivatives of the invention has a branched structure with two legs.

In a particular embodiment, the side chain is capable of forming non-covalent complexes with albumin, thereby promoting the circulation of the derivative with the blood stream, and also having the effect of protracting the time of action of the derivative, due to the fact that the complex of the GLP-1-derivative and albumin is only slowly disintegrated to release the active pharmaceutical ingredient. Thus, the substituent, or side chain, as a whole is preferably referred to as an albumin binding moiety.

In another particular embodiment the albumin binding moiety comprises a portion which is particularly relevant for the albumin binding and thereby the protraction, which portion may accordingly be referred to as a protracting moiety. The protracting moiety may be near, preferably at, the terminal (or distal, or free) end of the albumin binding moiety, relative to its point of attachment to the peptide. The albumin binding moiety is attached to the peptide by acylation of a lysine residue of the peptide, in particular by acylation to the epsilon-amino group of the lysine residue.

The branched derivatives of the invention comprise a first and a second protracting moiety of formula Chem. 1: HOOC—$(CH_2)_{18}$—CO—*, or Chem. 1a: HOOC—$(CH_2)_{20}$—CO—*; which may also be referred to as C20 diacid, or C22 diacid, respectively.

In a still further particular embodiment the albumin binding moiety comprises a portion between the protracting moiety and the point of attachment to the peptide, which portion may be referred to as a linker, linker moiety, spacer, or the like. The branched derivatives of the invention comprise a bivalent bis-amino or branched linker of formula Chem. 2:

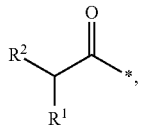

wherein $R^1$ is —$(CH_2)_q$—NH—* wherein q is an integer in the range of 0-5, $R^2$ is —$(CH_2)_w$—NH—* wherein w is an integer in the range of 0-5, with the provisos that when w is 0 q is an integer in the range of 1-5, and when q is 0 w is an integer in the range of 1-5.

In a particular embodiment, when q=4 and w=0, Chem. 2 represents a bis-amino radical of Lys, which may also be referred to as eps-Lys(Bis), where eps stands for epsilon, which in turn refers to the fact that the C-atom in the $R^1$-branch of Chem. 2 to which the NH—* group is bound is defined as the ε-atom. Likewise, when w=4 and q=0 Chem. 2 also represents eps-Lys(Bis).

In a particular embodiment the branched linker is attached to the epsilon-amino group of a Lys residue in the GLP-1 peptide at its CO—* end, under the formation of an amide bond, and to each of the first and second protracting moiety at each of its NH—* ends, respectively, via a further linker which comprises an element_1 of formula Chem. 3:

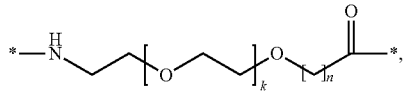

wherein k is an integer in the range of 1-15, and n is an integer in the range of 1-5, and, optionally, one or more additional linker elements, also under the formation of amide bonds.

In a particular embodiment, when k=1 and n=1, the Chem. 3 element_1 may be designated OEG, or a di-radical of 8-amino-3,6-dioxaoctanoic acid.

These are additional non-limiting examples of particular embodiments of the Chem. 3 element_1 group:

When k=3 and n=2, the element_1 may be designated dPEG4; when k=5 and n=2, the element_1 may be designated dPEG6; when k=11 and n=2, the element_1 may be designated dPEG12; and when k=15 and n=2, the element_1 may be designated dPEG16.

Each of the two acyl chains comprises a protracting moiety as defined above, attached to one or the other of the NH—* groups of the branched linker via a further linker, in each of the two legs. The two protracting moieties and the two further linkers may be referred to as the 1st and the 2nd protracting moiety, and the 1st and the 2nd further linker, respectively.

Each of these further linkers comprises the OEG-like element_1 of Chem. 3. They may comprise this element more than one time, and they may comprise additional linker elements, in various combinations.

Whenever the further linker is said to "comprise" a certain element, it may in addition contain other linker element, whereas the term "incorporates" is intended to mean the same as "has" or "includes only". Therefore, a further linker which "incorporates" five elements_1 of formula Chem. 3 has only five of these elements in its structure.

In a particular embodiment, each of the further linkers of the derivative may comprise, independently, an element_2 linker element, which is a Glu di-radical of formula Chem. 4:

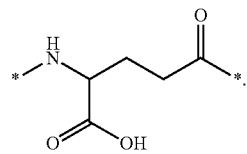

The Glu di-radical may also be included one or more times. It may be referred to as gamma-Glu, or briefly gGlu, due to the fact that it is the gamma carboxy group of the amino acid glutamic acid which is here used for connection to another linker element, or to the epsilon-amino group of lysine, as the case may be.

In still further particular embodiments, each of the further linkers of the derivative may comprise, independently, one or more additional linker elements such as an element_3 of formula Chem. 5, which may be referred to as Trx (for tranexamic acid), or an element_4 of formula Chem. 6, which may be referred to as Inp (isonipecotic acid).

Various particular combinations of linker elements are described in more detail below in the section headed "Particular embodiments". The sequence in which the elements are indicated here is generally from the N-terminus to the C-terminus.

As explained above, the GLP-1 derivatives of the invention are branched with two legs, each of which may be referred to in their entirety as albumin binding moieties.

In a particular embodiment, the two albumin binding moieties (i.e. the two legs) are similar, preferably substantially identical, or, most preferably, identical.

In another particular embodiment, the two protracting moieties are similar, preferably substantially identical, or, most preferably, identical.

In a still further particular embodiment, the two further linkers are similar, preferably substantially identical, or, most preferably identical.

The term "substantially identical" includes differences from identity which are due to formation of one or more esters and/or amides; preferably formation of one or more methyl esters, and simple amides; more preferably formation of no more than two methyl esters, and/or simple amides; or most preferably formation of no more than one methyl ester, and/or simple amide.

In the context of chemical compounds such as the albumin binding moieties, protracting moieties, and linkers, similarity and/or identity may be determined using any suitable computer program and/or algorithm known in the art.

For example, the similarity of two protracting moieties, two linkers, and/or two entire side chains may suitably be determined using molecular fingerprints. Fingerprints is a mathematical method of representing a chemical structure (see e.g. Chemoinformatics: A textbook, Johann Gasteiger and Thomas Engel (Eds), Wiley-VCH Verlag, 2003).

Examples of suitable fingerprints include, without limitation, UNITY fingerprints, MDL fingerprints, and/or ECFP fingerprints, such as ECFP_6 fingerprints (ECFP stands for extended-connectivity fingerprints).

In particular embodiments, the two protracting moieties, the two linkers, and/or the two entire side chains are represented as a) ECFP_6 fingerprints; b) UNITY fingerprints; and/or c) MDL fingerprints.

The Tanimoto coefficient is preferably used for calculating the similarity of the two fingerprints, whether a), b), or c) is used.

In particular embodiments, whether a), b), or c) is used, the two protracting moieties, the two linkers, and/or the two entire side chains, respectively, have a similarity of at least 0.5 (50%); preferably at least 0.6 (60%); more preferably at least 0.7 (70%), or at least 0.8 (80%); even more preferably at least 0.9 (90%); or most preferably at least 0.99 (99%), such as a similarity of 1.0 (100%).

UNITY fingerprints may be calculated using the programme SYBYL (available from Tripos, 1699 South Hanley Road, St. Louis, Mo. 63144-2319 USA). ECFP_6 and MDL fingerprints may be calculated using the programme Pipeline Pilot (available from Accelrys Inc., 10188 Telesis Court, Suite 100, San Diego, Calif. 92121, USA).

For more details, see for example J. Chem. Inf. Model. 2008, 48, 542-549; J. Chem. Inf. Comput. Sci. 2004, 44, 170-178; J. Med. Chem. 2004, 47, 2743-2749; J. Chem. Inf. Model. 2010, 50, 742-754; as well as SciTegic Pipeline Pilot Chemistry Collection: Basic Chemistry User Guide, March 2008, SciTegic Pipeline Pilot Data Modeling Collection, 2008—both from Accelrys Software Inc., San Diego, US, and the guides http://www.tripos.com/tripos_resources/file-root/pdfs/Unity_111408.pdf, and http://www.tripos.com/data/SYBYL/SYBYL_072505.pdf.

An example of a similarity calculation is inserted hereinbelow, in which a known entire side chain of a known GLP-1 derivative was compared with a methyl ester thereof:

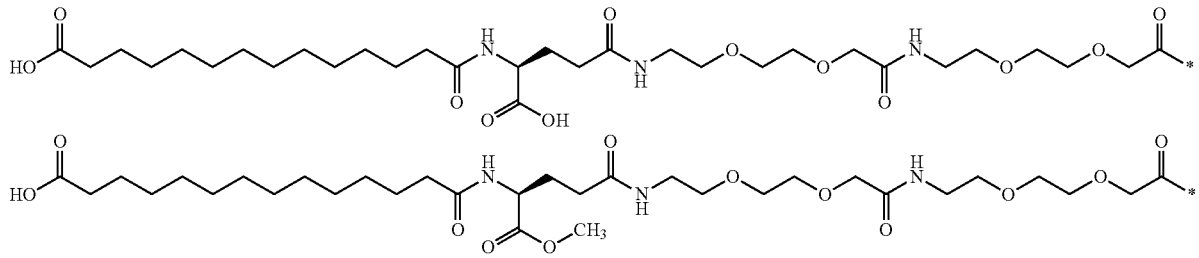

Using a) ECFP_6 fingerprints the similarity is 0.798, using b) UNITY fingerprints the similarity is 0.957; and using MDL fingerprints the similarity is 0.905.

In case of two identical side chains (albumin binding moieties) the derivative may be designated symmetrical.

In particular embodiments, the similarity coefficient is at least 0.80, preferably at least 0.85, more preferably at least 0.90, even more preferably at least 0.95, or most preferably at least 0.99.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channelled into the acceptor beads and triggered chemiluminescence which was measured in an Envision plate reader. The amount of light was proportional to the concentration of the compound.

Pharmaceutically Acceptable Salt, Amide, or Ester

The derivatives, analogues, and intermediate products of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

In a particular embodiment the derivatives and analogues of the invention are basic salts. The salts may, e.g., be formed between anionic groups in the peptide moiety and added sodium or potassium cations.

The ester of the derivatives of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In a particular embodiment, the peptide or derivative is in the form of a pharmaceutically acceptable salt. In another particular embodiment, the derivative is in the form of a pharmaceutically acceptable amide, preferably with an amide group at the C-terminus of the peptide. In a still further particular embodiment, the peptide or derivative is in the form a pharmaceutically acceptable ester.

Functional Properties

In a particular embodiment the derivatives of the invention have a very long half-life and at the same time a very good potency in vitro and in vivo, which makes them potentially suitable for once-monthly administration.

Thus, in a first functional aspect, the derivatives of the invention have a good potency. Also, or alternatively, in a second aspect, they bind very well to the GLP-1 receptor, e.g. at a high concentration of albumin. Preferably they are full GLP-1 receptor agonists as is reflected by their ability to bind strongly to the GLP-1 receptor combined with the capacity to activate the receptor. Also, or alternatively, in a third functional aspect, they have improved pharmacokinetic properties.

Biological Activity—In Vitro Potency

According to the first functional aspect, the derivatives of the invention, as well as the constituent GLP-1 peptides as such, are biologically active, or potent.

In a particular embodiment, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 35.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described above, and the $EC_{50}$ of the derivative in question determined. The lower the $EC_{50}$ value, the better the potency.

In a particular embodiment, the derivatives of the invention are very potent, despite the fact that they have very long half-lives. In a particular embodiment, the derivative of the invention has an in vitro potency determined using the method of Example 35 corresponding to an $EC_{50}$ at or below 300 pM.

Biological Activity—In Vivo Pharmacology

In another particular embodiment the derivatives of the invention as well as the constituent GLP-1 peptides as such are potent in vivo, which may be determined as is known in the art in any suitable animal model, as well as in clinical trials.

The diabetic db/db mouse is one example of a suitable animal model, and the blood glucose and/or body weight lowering effect may be determined in such mice in vivo, e.g. as described in Example 38. In a particular embodiment the derivatives of the invention are capable of lowering blood glucose and body weight in db/db mice for at least up to 96 hours.

The LYD pig is another example of a suitable animal model, and the reduction in food intake may be determined in a PD study in such pigs in vivo, e.g. as described in Example 39.

In a particular embodiment the derivatives of the invention are very potent in vivo and over a long time, which is evidenced by the results found in the experimental part and also referred to in the section headed "Particular embodiments".

Biological Activity—In Vitro Receptor Binding

According to the second functional aspect, the derivatives of the invention, as well as the constituent GLP-1 peptides as such bind very well to the GLP-1 receptor, e.g. at a high concentration of albumin. This may be determined as described in Example 36.

Generally, the binding to the GLP-1 receptor at low albumin concentration should be as good as possible, corresponding to a low $IC_{50}$ value.

The $IC_{50}$ value at high albumin concentration reflects the influence of serum albumin on the binding of the derivative to the GLP-1 receptor. As is known, the GLP-1 derivatives can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In a particular embodiment, the derivatives of the invention bind very well to the GLP-1 receptor at a low albumin concentration, but they also bind very well at a high albumin concentration.

As an example, in a particular embodiment, the GLP-1 receptor binding affinity ($IC_{50}$) of the derivatives of the invention in the presence of 2.0% HSA (high albumin) is at 300 nM or below.

Pharmacokinetics Profile

According to the third functional aspect, the derivatives of the invention have improved pharmacokinetic properties such as increased terminal half-life, and/or decreased clearance.

Increasing terminal half-life and/or decreasing of the clearance means that the compound in question is eliminated slower from the body. For the derivatives of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2} = \ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 37 herein.

In a particular embodiment the derivatives of the invention have an excellent terminal half-life in minipigs which makes them suitable for once-monthly administration. In a particular embodiment, the terminal half-life of the derivatives of the invention in minipigs after i.v. administration is at least 100 hours.

Additional particular embodiments of the derivatives of the invention are described in the section headed "Particular embodiments" before the experimental section.

Production Processes

The production of peptides like GLP-1(7-37) and GLP-1 analogues is well known in the art.

The GLP-1 moiety of the derivatives of the invention (or fragments thereof) may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli*, *Saccharomyces cerevisiae*, as well as mammalian BHK or CHO cell lines.

Those derivatives of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Pharmaceutical Compositions

The invention also relates to pharmaceutical compositions comprising a derivative of the invention or a pharmaceutically acceptable salt, amide, or ester thereof, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorophenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidine HCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728.

An administered dose may contain from 0.1 mg-100 mg of the derivative, from 1-100 mg of the derivative, or from 1-50 mg of the derivative.

The derivative may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative according to this invention may also be combined with a surgery that influences the glucose levels, and/or lipid homeostasis such as gastric banding or gastric bypass.

Pharmaceutical Indications

The present invention also relates to a derivative of the invention, for use as a medicament.

In particular embodiments, the derivative of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In a particular embodiment the indication is selected from the group consisting of (i)-(xiv), such as indications (i)-(viii), (x)-(xiii), and/or (xiv), and relates in one way or the other to diabetes.

In another particular embodiment, the indication is selected from the group consisting of (i)-(iii) and (v)-(viii), such as indications (i), (ii), and/or (iii); or indication (v), indication (vi), indication (vii), and/or indication (viii).

In a still further particular embodiment, the indication is (i). In a further particular embodiment the indication is (v). In a still further particular embodiment the indication is (viii). The following indications are particularly preferred: Type 2 diabetes, and/or obesity.

Particular Embodiments

The following are particular embodiments of the invention:

1. A derivative of a GLP-1 peptide, wherein the GLP-1 peptide is of formula I:

Formula I:

$Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$, wherein $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, α-methyl-histidine, 3-pyridylalanine, 2-pyridylalanine, or 4-pyridylalanine;

$Xaa_8$ is Ala, Gly, Ser, Aib, (1-aminocyclopropyl) carboxylic acid, or (1-aminocyclobutyl) carboxylic acid;

$Xaa_{12}$ is Phe or Leu;

$Xaa_{16}$ is Val or Leu;

$Xaa_{18}$ is Ser, Val, Lys, Arg, or Leu;

$Xaa_{19}$ is Tyr or Gln;

$Xaa_{20}$ is Leu or Met;

$Xaa_{22}$ is Gly or Glu;

$Xaa_{23}$ is Gln, Glu, or Arg;

$Xaa_{25}$ is Ala or Val;

$Xaa_{26}$ is Arg or Lys;

$Xaa_{27}$ is Glu, Lys, or Leu;

$Xaa_{30}$ is Ala, Glu, or Arg;

$Xaa_{31}$ is Trp or His;

$Xaa_{33}$ is Val, Lys, or Arg;

$Xaa_{34}$ is Arg, Lys, His, Asn, or Gln;

$Xaa_{35}$ is Gly or Ala;

$Xaa_{36}$ is Arg or Gly;

$Xaa_{37}$ is Gly, Pro, or Lys;

$Xaa_{38}$ is Ser, Gly, Ala, Glu, Pro, Lys, or absent;

$Xaa_{39}$ is Ser, Gly, Ala, Glu, Pro, Lys, or absent;

$Xaa_{40}$ is Ser, Gly, Ala, Glu, Pro, Lys, or absent;

$Xaa_{41}$ is Ser, Gly, Ala, Glu, Pro, Lys, or absent;

$Xaa_{42}$ is Ser, Gly, Ala, Glu, Pro, Lys, or absent; and $Xaa_{43}$ is Ser, Gly, Ala, Glu, Pro, Lys, or absent;

which GLP-1 peptide comprises a Lys residue at a position corresponding to position 27, 37, 38, 39, 40, 41, 42, or 43 of GLP-1(7-37) (SEQ ID NO: 1);

which derivative comprises
a first and a second protracting moiety selected from Chem. 1 and Chem. 1a:

HOOC—(CH$_2$)$_{18}$—CO—*, and                    Chem. 1:

HOOC—(CH$_2$)$_{20}$—CO—*;                         Chem. 1a:

a branched linker of formula Chem. 2:

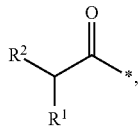

Chem. 2 wherein
R$^1$ is —(CH$_2$)$_q$—NH—*, wherein q is an integer in the range of 0-5,
R$^2$ is —(CH$_2$)$_w$—NH—*, wherein w is an integer in the range of 0-5,
with the provisos that when w is 0 q is an integer in the range of 1-5, and when q is 0 w is an integer in the range of 1-5; and
a first and a second further linker, each comprising an element_1 of formula Chem. 3:

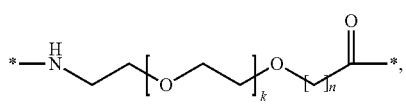

Chem. 3 wherein k is an integer in the range of 1-15, and n is an integer in the range of 1-5;
wherein
the first protracting moiety is attached at its *—CO end to a first *—NH end of the branched linker, via the first further linker,
the second protracting moiety is attached at its *—CO end to a second *—NH end of the branched linker, via the second further linker; and
the branched linker is attached at its *—CO end to the epsilon amino group of the Lys residue of the GLP-1 peptide;
or a pharmaceutically acceptable salt, amide, or ester thereof.

2. The derivative of embodiment 1, wherein q=4 and w=0.
3. The derivative of any of embodiments 1-2, wherein Chem. 2 represents eps-Lys(Bis).
4. The derivative of any of embodiments 1-3, wherein the first further linker and the second further linker each comprises at least one element_1 of formula Chem. 3.
5. The derivative of any of embodiments 1-4, wherein the first further linker and the second further linker each comprises at least two elements_1 of formula Chem. 3.
6. The derivative of any of embodiments 1-5, wherein the first further linker and the second further linker each comprises at least three elements_1 of formula Chem. 3.
7. The derivative of any of embodiments 1-6, wherein the first further linker and the second further linker each comprises at least four elements_1 of formula Chem. 3.
8. The derivative of any of embodiments 1-7, wherein the first further linker and the second further linker each comprises at least five elements_1 of formula Chem. 3.
9. The derivative of any of embodiments 1-8, wherein the first further linker and the second further linker each comprises at least six elements_1 of formula Chem. 3.
10. The derivative of any of embodiments 1-9, wherein the first further linker and the second further linker each incorporates one element_1 of formula Chem. 3.
11. The derivative of any of embodiments 1-10, wherein the first further linker and the second further linker each incorporates two elements_1 of formula Chem. 3.
12. The derivative of any of embodiments 1-11, wherein the first further linker and the second further linker each incorporates three elements_1 of formula Chem. 3.
13. The derivative of any of embodiments 1-12, wherein the first further linker and the second further linker each incorporates four elements_1 of formula Chem. 3.
14. The derivative of any of embodiments 1-13, wherein the first further linker and the second further linker each incorporates five elements_1 of formula Chem. 3.
15. The derivative of any of embodiments 1-14, wherein the first further linker and the second further linker each incorporates six elements_1 of formula Chem. 3.
16. The derivative of any of embodiments 1-15, wherein n is 1 or 2.
17. The derivative of any of embodiments 1-16, wherein k is 1, 3, 5, 11, or 15.
18. The derivative of any of embodiments 1-17, wherein k=1 and n=1.
19. The derivative of any of embodiments 1-18, wherein Chem. 3 represents OEG.
20. The derivative of any of embodiments 1-19, wherein the first further linker and the second further linker each incorporates 2×OEG, 3×OEG, 4×OEG, 5×OEG, or 6×OEG.
21. The derivative of any of embodiments 1-20, wherein n=2 and k=3.
22. The derivative of any of embodiments 1-21, wherein Chem. 3 represents dPEG4.
23. The derivative of any of embodiments 1-22, wherein the first further linker and the second further linker each incorporates 3×dPEG4.
24. The derivative of any of embodiments 1-23, wherein n=2 and k=5.
25. The derivative of any of embodiments 1-24, wherein Chem. 3 represents dPEG6.
26. The derivative of any of embodiments 1-25, wherein the first further linker and the second further linker each incorporates 2×dPEG6.
27. The derivative of any of embodiments 1-26, wherein n=2 and k=11.
28. The derivative of any of embodiments 1-27, wherein Chem. 3 represents dPEG12.
29. The derivative of any of embodiments 1-28, wherein the first further linker and the second further linker each incorporates 1×dPEG12.
30. The derivative of any of embodiments 1-29, wherein n=2 and k=15.
31. The derivative of any of embodiments 1-30, wherein Chem. 3 represents dPEG16.
32. The derivative of any of embodiments 1-31, wherein the first further linker and the second further linker each incorporates 1×dPEG16.
33. The derivative of any of embodiments 1-32, wherein the first further linker and the second further linker each incorporates an *—NH or *—N group, and a *—CO group.

34. The derivative of any of embodiments 1-33, wherein
an amide bond connects the *—CO end of the first protracting moiety to the *—NH or *—N end of the first further linker, and an amide bond connects the *—CO end of the first further linker to the first *—NH end of the branched linker; and
an amide bond connects the *—CO end of the second protracting moiety to the *—NH or *—N end of the second further linker, and an amide bond connects the *—CO end of the second further linker to the second *—NH end of the branched linker.

35. The derivative of any of embodiments 1-34, wherein the first further linker and the second further linker each comprises an element_2 of formula Chem. 4:

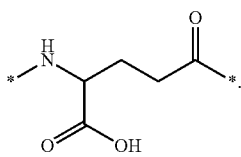

Chem. 4

36. The derivative of any of embodiments 1-35, wherein the first further linker and the second further linker each incorporates one element_2 of formula Chem. 4:

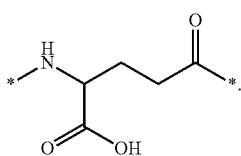

Chem. 4

37. The derivative of any of embodiments 1-36, wherein Chem. 4 represents gGlu.
38. The derivative of any of embodiments 1-37, wherein Chem. 4 represents the L-form of gGlu.
39. The derivative of any of embodiments 1-38, wherein the first further linker and the second further linker each comprises an element_3 of formula Chem. 5:

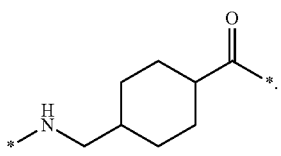

Chem. 5

40. The derivative of any of embodiments 1-39, wherein the first further linker and the second further linker each incorporates one element_3 of formula Chem. 5:

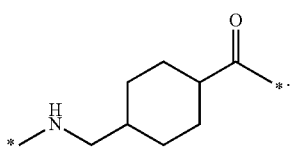

Chem. 5

41. The derivative of any of embodiments 1-40, wherein Chem. 5 represents Trx.
42. The derivative of any of embodiments 1-41, wherein the first further linker and the second further linker each comprises an element_4 of formula Chem. 6:

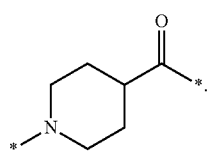

Chem. 6

43. The derivative of any of embodiments 1-42, wherein the first further linker and the second further linker each incorporates one element_4 of formula Chem. 6:

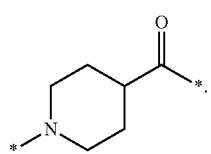

Chem. 6

44. The derivative of any of embodiments 1-43, wherein Chem. 6 represents Inp.
45. The derivative of any of embodiments 1-44, wherein the first further linker and the second further linker each consists of one element_2 of formula Chem. 4, and two elements_1 of formula Chem. 3 wherein k=1 and n=1, interconnected via amide bonds and in the sequence indicated.
46. The derivative of any of embodiments 1-45, wherein the first further linker and the second further linker each consists of one element_4 of formula Chem. 6, one element_2 of formula Chem. 4, and two elements_1 of formula Chem. 3 wherein k=1 and n=1, interconnected via amide bonds and in the sequence indicated.
47. The derivative of any of embodiments 1-46, wherein the first further linker and the second further linker each consists of one element_3 of formula Chem. 5, one element_2 of formula Chem. 4, and two elements_1 of formula Chem. 3 wherein k=1 and n=1, interconnected via amide bonds and in the sequence indicated.
48. The derivative of any of embodiments 1-47, wherein the first further linker and the second further linker each consists of one element 3 of formula Chem. 5, one element_2 of formula Chem. 4, and three elements_1 of formula Chem. 3 wherein k=1 and n=1, interconnected via amide bonds and in the sequence indicated.
49. The derivative of any of embodiments 1-48, wherein the first further linker and the second further linker each consists of one element_3 of formula Chem. 5, one element_2 of formula Chem. 4, and four elements_1 of formula Chem. 3 wherein k=1 and n=1, interconnected via amide bonds and in the sequence indicated.
50. The derivative of any of embodiments 1-49, wherein the first further linker and the second further linker each consists of one element_3 of formula Chem. 5, one element_2 of formula Chem. 4, and five elements_1 of formula Chem. 3 wherein k=1 and n=1, interconnected via amide bonds and in the sequence indicated.

51. The derivative of any of embodiments 1-50, wherein the first further linker and the second further linker each consists of one element_3 of formula Chem. 5, one element_2 of formula Chem. 4, and six elements_1 of formula Chem. 3 wherein k=1 and n=1, interconnected via amide bonds and in the sequence indicated.

52. The derivative of any of embodiments 1-51, wherein the first further linker and the second further linker each consists of one element_3 of formula Chem. 5, one element_2 of formula Chem. 4, and three elements_1 of formula Chem. 3 wherein k=3 and n=2, interconnected via amide bonds and in the sequence indicated.

53. The derivative of any of embodiments 1-52, wherein the first further linker and the second further linker each consists of one element 3 of formula Chem. 5, one element_2 of formula Chem. 4, and two elements_1 of formula Chem. 3 wherein k=5 and n=2, interconnected via amide bonds and in the sequence indicated.

54. The derivative of any of embodiments 1-53, wherein the first further linker and the second further linker each consists of one element_3 of formula Chem. 5, one element_2 of formula Chem. 4, and one element_1 of formula Chem. 3 wherein k=11 and n=2, interconnected via amide bonds and in the sequence indicated.

55. The derivative of any of embodiments 1-54, wherein the first further linker and the second further linker each consists of one element_3 of formula Chem. 5, one element_2 of formula Chem. 4, and one element_1 of formula Chem. 3 wherein k=15 and n=2, interconnected via amide bonds and in the sequence indicated.

56. The derivative of any of embodiments 1-55 which comprises a Lys residue at a position corresponding to position 27 of GLP-1(7-37) (SEQ ID NO: 1).

57. The derivative of any of embodiments 1-56 which comprises a Lys residue at a position corresponding to position 37 of GLP-1(7-37) (SEQ ID NO: 1).

58. The derivative of any of embodiments 1-57 which comprises a Lys residue at a position corresponding to position 38 of GLP-1(7-37) (SEQ ID NO: 1).

59. The derivative of any of embodiments 1-58 which comprises a Lys residue at a position corresponding to position 39 of GLP-1(7-37) (SEQ ID NO: 1).

60. The derivative of any of embodiments 1-59 which comprises a Lys residue at a position corresponding to position 40 of GLP-1(7-37) (SEQ ID NO: 1).

61. The derivative of any of embodiments 1-60 which comprises a Lys residue at a position corresponding to position 41 of GLP-1(7-37) (SEQ ID NO: 1).

62. The derivative of any of embodiments 1-61 which comprises a Lys residue at a position corresponding to position 42 of GLP-1(7-37) (SEQ ID NO: 1).

63. The derivative of any of embodiments 1-62 which comprises a Lys residue at a position corresponding to position 43 of GLP-1(7-37) (SEQ ID NO: 1).

64. The derivative of any of embodiments 1-63 wherein each of the first and the second protracting moiety is Chem. 1.

65. The derivative of any of embodiments 1-64 wherein each of the first and the second protracting moiety is Chem. 1a.

66. The derivative of any of embodiments 1-65, wherein in Formula I:
(i) $Xaa_7$ is L-histidine, (S)-2-Hydroxy-3-(1H-imidazol-4-yl)-propionic acid, D-histidine, desamino-histidine, $N^\alpha$-acetyl-histidine, $N^\alpha$-formyl-histidine, or α-methyl-histidine; $Xaa_8$ is Ala, Gly, Ser, Aib, (1-aminocyclopropyl) carboxylic acid, or (1-aminocyclobutyl) carboxylic acid; $Xaa_{12}$ is Phe; $Xaa_{16}$ is Val or Leu; $Xaa_{18}$ is Ser, Lys, or Arg; $Xaa_{19}$ is Tyr or Gln; $Xaa_{20}$ is Leu or Met; $Xaa_{22}$ is Gly or Glu; $Xaa_{23}$ is Gln, Glu, or Arg; $Xaa_{25}$ is Ala or Val; $Xaa_{26}$ is Arg or Lys; $Xaa_{27}$ is Glu, Lys, or Leu; $Xaa_{30}$ is Ala or Glu; $Xaa_{31}$ is Trp or His; $Xaa_{33}$ is Val, Lys, or Arg; $Xaa_{34}$ is Arg, Lys, or Asn; $Xaa_{35}$ is Gly; $Xaa_{36}$ is Arg or Gly; $Xaa_{37}$ is Gly, Pro, or Lys; $Xaa_{38}$ is Ser, Gly, Ala, Glu, Pro, Lys, or absent; $Xaa_{39}$ is Ser, Gly, Ala, Glu, Pro, Lys, or absent; $Xaa_{40}$ is Ser, Gly, Ala, Glu, Pro, Lys, or absent; $Xaa_{41}$ is Ser, Gly, Ala, Glu, Pro, Lys, or absent; $Xaa_{42}$ is Gly, Ala, Glu, Pro, Lys, or absent; and $Xaa_{43}$ is Lys or absent; or, preferably, (ii) $Xaa_7$ is L-histidine or desamino-histidine; $Xaa_8$ is Aib; $Xaa_{12}$ is Phe; $Xaa_{16}$ is Val; $Xaa_{18}$ is Ser; $Xaa_{19}$ is Tyr; $Xaa_{20}$ is Leu; $Xaa_{22}$ is Gly; $Xaa_{23}$ is Gln; $Xaa_{25}$ is Ala; $Xaa_{26}$ is Arg; $Xaa_{27}$ is Glu or Lys; $Xaa_{30}$ is Ala; $Xaa_{31}$ is Trp; $Xaa_{33}$ is Val; $Xaa_{34}$ is Arg; $Xaa_{35}$ is Gly; $Xaa_{36}$ is Arg; $Xaa_{37}$ is Gly, Pro, or Lys; $Xaa_{38}$ is Ser, Gly, Ala, Glu, Pro, Lys, or absent; $Xaa_{39}$ is Ser, Gly, Ala, Glu, Pro, Lys, or absent; $Xaa_{40}$ is Ser, Gly, Ala, Glu, Pro, Lys, or absent; $Xaa_{41}$ is Ser, Gly, Ala, Glu, Pro, Lys, or absent; $Xaa_{42}$ is Gly, Ala, Glu, Pro, Lys, or absent; and $Xaa_{43}$ is Lys or absent.

67. The derivative of any of embodiments 1-66, wherein
i) if $Xaa_{42}$ is absent, then $Xaa_{43}$ is also absent; and/or
ii) if $Xaa_{41}$ is absent, then $Xaa_{42}$ and $Xaa_{43}$ is also absent.

68. The derivative of any of embodiments 1-67, wherein if $Xaa_{40}$ is absent, then $Xaa_{41}$, $Xaa_{42}$, and $Xaa_{43}$ are also absent.

69. The derivative of any of embodiments 1-68, wherein if $Xaa_{39}$ is absent, then $Xaa_{40}$, $Xaa_{41}$, $Xaa_{42}$, and $Xaa_{43}$ are also absent.

70. The derivative of any of embodiments 1-69, wherein if $Xaa_{38}$ is absent, then $Xaa_{39}$, $Xaa_{40}$, $Xaa_{41}$, $Xaa_{42}$, and $Xaa_{43}$ are also absent.

71. The derivative of any of embodiments 1-70, wherein $Xaa_7$ is His.

72. The derivative of any of embodiments 1-71, wherein $Xaa_7$ is desamino-histidine.

73. The derivative of any of embodiments 1-72, wherein $Xaa_8$ is Aib.

74. The derivative of any of embodiments 1-73, wherein $Xaa_{12}$ is Phe.

75. The derivative of any of embodiments 1-74, wherein $Xaa_{16}$ is Val.

76. The derivative of any of embodiments 1-75, wherein $Xaa_{18}$ is Ser.

77. The derivative of any of embodiments 1-76, wherein $Xaa_{19}$ is Tyr.

78. The derivative of any of embodiments 1-77, wherein $Xaa_{20}$ is Leu.

79. The derivative of any of embodiments 1-78, wherein $Xaa_{22}$ is Gly.

80. The derivative of any of embodiments 1-79, wherein $Xaa_{22}$ is Glu.

81. The derivative of any of embodiments 1-80, wherein $Xaa_{23}$ is Gln.

82. The derivative of any of embodiments 1-81, wherein $Xaa_{25}$ is Ala.

83. The derivative of any of embodiments 1-82, wherein $Xaa_{26}$ is Arg.

84. The derivative of any of embodiments 1-83, wherein $Xaa_{27}$ is Glu.

85. The derivative of any of embodiments 1-84, wherein $Xaa_{27}$ is Lys.

86. The derivative of any of embodiments 1-85, wherein $Xaa_{30}$ is Ala.

87. The derivative of any of embodiments 1-86, wherein $Xaa_{31}$ is Trp.

88. The derivative of any of embodiments 1-87, wherein $Xaa_{33}$ is Val.
89. The derivative of any of embodiments 1-88, wherein $Xaa_{34}$ is Arg.
90. The derivative of any of embodiments 1-89, wherein $Xaa_{35}$ is Gly.
91. The derivative of any of embodiments 1-90, wherein $Xaa_{36}$ is Arg.
92. The derivative of any of embodiments 1-91, wherein $Xaa_{37}$ is Gly.
93. The derivative of any of embodiments 1-92, wherein $Xaa_{37}$ is Lys.
94. The derivative of any of embodiments 1-93, wherein $Xaa_{37}$ is Pro.
95. The derivative of any of embodiments 1-94, wherein $Xaa_{38}$ is Ser.
96. The derivative of any of embodiments 1-95, wherein $Xaa_{38}$ is Gly.
97. The derivative of any of embodiments 1-96, wherein $Xaa_{38}$ is Lys.
98. The derivative of any of embodiments 1-97, wherein $Xaa_{38}$ is absent.
99. The derivative of any of embodiments 1-98, wherein $Xaa_{38}$ is Ala.
100. The derivative of any of embodiments 1-99, wherein $Xaa_{38}$ is Glu.
101. The derivative of any of embodiments 1-100, wherein $Xaa_{38}$ is Pro.
102. The derivative of any of embodiments 1-101, wherein $Xaa_{39}$ is Ser.
103. The derivative of any of embodiments 1-102, wherein $Xaa_{39}$ is Gly.
104. The derivative of any of embodiments 1-103, wherein $Xaa_{39}$ is Lys.
105. The derivative of any of embodiments 1-104, wherein $Xaa_{39}$ is absent.
106. The derivative of any of embodiments 1-105, wherein $Xaa_{39}$ is Ala.
107. The derivative of any of embodiments 1-106, wherein $Xaa_{39}$ is Glu.
108. The derivative of any of embodiments 1-107, wherein $Xaa_{39}$ is Pro.
109. The derivative of any of embodiments 1-108, wherein $Xaa_{40}$ is Ser.
110. The derivative of any of embodiments 1-109, wherein $Xaa_{40}$ is Gly.
111. The derivative of any of embodiments 1-110, wherein $Xaa_{40}$ is Lys.
112. The derivative of any of embodiments 1-111, wherein $Xaa_{40}$ is absent.
113. The derivative of any of embodiments 1-112, wherein $Xaa_{40}$ is Ala.
114. The derivative of any of embodiments 1-113, wherein $Xaa_{40}$ is Glu.
115. The derivative of any of embodiments 1-114, wherein $Xaa_{40}$ is Pro.
116. The derivative of any of embodiments 1-115, wherein $Xaa_{41}$ is Ser.
117. The derivative of any of embodiments 1-116, wherein $Xaa_{41}$ is Ala.
118. The derivative of any of embodiments 1-117, wherein $Xaa_{41}$ is Lys.
119. The derivative of any of embodiments 1-118, wherein $Xaa_{41}$ is absent.
120. The derivative of any of embodiments 1-119, wherein $Xaa_{41}$ is Gly.
121. The derivative of any of embodiments 1-120, wherein $Xaa_{41}$ is Glu.
122. The derivative of any of embodiments 1-121, wherein $Xaa_{41}$ is Pro.
123. The derivative of any of embodiments 1-122, wherein $Xaa_{42}$ is Pro.
124. The derivative of any of embodiments 1-123, wherein $Xaa_{42}$ is Lys.
125. The derivative of any of embodiments 1-124, wherein $Xaa_{42}$ is absent.
126. The derivative of any of embodiments 1-125, wherein $Xaa_{42}$ is Gly.
127. The derivative of any of embodiments 1-126, wherein $Xaa_{42}$ is Ala.
128. The derivative of any of embodiments 1-127, wherein $Xaa_{42}$ is Glu.
129. The derivative of any of embodiments 1-128, wherein $Xaa_{43}$ is Lys.
130. The derivative of any of embodiments 1-129, wherein $Xaa_{43}$ is absent.
131. The derivative of any of embodiments 1-130, wherein the GLP-1 peptide has a maximum of 12 amino acid changes, when compared with GLP-1(7-37) (SEQ ID NO: 1).
132. The derivative of any of embodiments 1-131, wherein the GLP-1 peptide has a maximum of 11 amino acid changes, when compared with GLP-1(7-37) (SEQ ID NO: 1).
133. The derivative of any of embodiments 1-132, wherein the GLP-1 peptide has a maximum of 10 amino acid changes, when compared with GLP-1(7-37) (SEQ ID NO: 1).
134. The derivative of any of embodiments 1-133, wherein the GLP-1 peptide has a maximum of 9 amino acid changes, when compared with GLP-1(7-37) (SEQ ID NO: 1).
135. The derivative of any of embodiments 1-134, wherein the GLP-1 peptide has a maximum of 8 amino acid changes, when compared with GLP-1(7-37) (SEQ ID NO: 1).
136. The derivative of any of embodiments 1-135, wherein the GLP-1 peptide has a maximum of 7 amino acid changes, when compared with GLP-1(7-37) (SEQ ID NO: 1).
137. The derivative of any of embodiments 1-136 wherein the GLP-1 peptide has a maximum of 6 amino acid changes, when compared with GLP-1(7-37) (SEQ ID NO: 1).
138. The derivative of any of embodiments 1-137, wherein the GLP-1 peptide has a maximum of 5 amino acid changes, when compared with GLP-1(7-37) (SEQ ID NO: 1).
139. The derivative of any of embodiments 1-138, wherein the GLP-1 peptide has a maximum of 4 amino acid changes, when compared with GLP-1(7-37) (SEQ ID NO: 1).
140. The derivative of any of embodiments 1-139, wherein the GLP-1 peptide has a maximum of 3 amino acid changes, when compared with GLP-1(7-37) (SEQ ID NO: 1).
141. The derivative of any of embodiments 1-140, wherein the GLP-1 peptide has a maximum of 2 amino acid changes, when compared with GLP-1(7-37) (SEQ ID NO: 1).

142. The derivative of any of embodiments 1-141, wherein the GLP-1 peptide has a maximum of 1 amino acid changes, when compared with GLP-1(7-37) (SEQ ID NO: 1).
143. The derivative of any of embodiments 1-142, wherein the GLP-1 peptide has a minimum of 1 amino acid change, when compared with GLP-1(7-37) (SEQ ID NO: 1).
144. The derivative of any of embodiments 1-143, wherein the GLP-1 peptide has a minimum of 2 amino acid changes, when compared with GLP-1(7-37) (SEQ ID NO: 1).
145. The derivative of any of embodiments 1-144, wherein the GLP-1 peptide has a minimum of 3 amino acid changes, when compared with GLP-1(7-37) (SEQ ID NO: 1).
146. The derivative of any of embodiments 1-145, wherein the GLP-1 peptide has a minimum of 4 amino acid changes, when compared with GLP-1(7-37) (SEQ ID NO: 1).
147. The derivative of any of embodiments 1-146, wherein the GLP-1 peptide has a minimum of 5 amino acid changes, when compared with GLP-1(7-37) (SEQ ID NO: 1).
148. The derivative of any of embodiments 1-147, wherein the GLP-1 peptide has a minimum of 6 amino acid changes, when compared with GLP-1(7-37) (SEQ ID NO: 1).
149. The derivative of any of embodiments 1-148, wherein the GLP-1 peptide has a minimum of 7 amino acid changes, when compared with GLP-1(7-37) (SEQ ID NO: 1).
150. The derivative of any of embodiments 1-149, wherein the GLP-1 peptide has a minimum of 8 amino acid changes, when compared with GLP-1(7-37) (SEQ ID NO: 1).
151. The derivative of any of embodiments 1-150, wherein the GLP-1 peptide has a minimum of 9 amino acid changes, when compared with GLP-1(7-37) (SEQ ID NO: 1).
152. The derivative of any of embodiments 1-151, wherein the GLP-1 peptide has a minimum of 10 amino acid changes, when compared with GLP-1(7-37) (SEQ ID NO: 1).
153. The derivative of any of embodiments 1-152, wherein the GLP-1 peptide has 4 amino acid changes, when compared with GLP-1(7-37) (SEQ ID NO: 1).
154. The derivative of any of embodiments 1-153, wherein the GLP-1 peptide has 5 amino acid changes, when compared with GLP-1(7-37) (SEQ ID NO: 1).
155. The derivative of any of embodiments 1-154, wherein the GLP-1 peptide has 6 amino acid changes, when compared with GLP-1(7-37) (SEQ ID NO: 1).
156. The derivative of any of embodiments 1-155, wherein the GLP-1 peptide has 7 amino acid changes, when compared with GLP-1(7-37) (SEQ ID NO: 1).
157. The derivative of any of embodiments 1-156, wherein the GLP-1 peptide has 8 amino acid changes, when compared with GLP-1(7-37) (SEQ ID NO: 1).
158. The derivative of any of embodiments 1-157, wherein the GLP-1 peptide has 9 amino acid changes, when compared with GLP-1(7-37) (SEQ ID NO: 1).
159. The derivative of any of embodiments 1-158, wherein the GLP-1 peptide has 10 amino acid changes, when compared with GLP-1(7-37) (SEQ ID NO: 1).
160. The derivative of any of embodiments 1-159, wherein the GLP-1 peptide incorporates only one Lys.
161. The derivative of any of embodiments 1-160, wherein the GLP-1 peptide is selected from the following analogues of GLP-1 (7-37) (SEQ ID NO: 1): i) (8Aib, 22E, 26R, 27K, 34R) (SEQ ID NO: 10), ii) (8Aib, 22E, 26R, 34R, 37K) (SEQ ID NO: 6), iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vi) (8Aib, 22E, 26R, 34R, 38K) (SEQ ID NO: 7), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii) (8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), and xvii) (8Aib, 22E, 26R, 34R, 37P, 38K) (SEQ ID NO: 18).
162. The derivative of any of embodiments 1-161 in the form of a salt; preferably a basic or acid salt such as an acid acetate salt, a basic sodium salt, or a basic potassium salt; more preferably a basic salt such as a sodium or a potassium salt; most preferably a sodium salt.
163. The derivative of any of embodiments 1-162 which is a GLP-1 receptor agonist.
164. The derivative of any of embodiments 1-163, which is a full GLP-1 receptor agonist.
165. The derivative of any of embodiments 1-164, which is biologically active in vitro.
166. The derivative of any of embodiments 1-165, which is potent in vitro.
167. The derivative of any of embodiments 1-166, which is capable of activating the human GLP-1 receptor.
168. The derivative of any of embodiments 1-167 which is capable of activating the human GLP-1 receptor in an assay with whole cells expressing the human GLP-1 receptor, wherein the assay is performed in the absence of HSA (0% HSA), and/or in the presence of HSA (1% HSA), preferably in the absence of HSA.
169. The derivative of any of embodiments 1-168, where the response of the human GLP-1 receptor is measured in a reporter gene assay, such as the assay of Example 35.
170. The derivative of any of embodiments 1-169, wherein the biological activity, or potency, in vitro is determined essentially as described in Example 35.
171. The derivative of any of embodiments 1-170, which has an in vitro potency corresponding to an $EC_{50}$ of 300 pM or below.
172. The derivative of any of embodiments 1-171, which has an in vitro potency corresponding to an $EC_{50}$ of 200 pM or below.
173. The derivative of any of embodiments 1-172, which has an in vitro potency corresponding to an $EC_{50}$ of 100 pM or below.
174. The derivative of any of embodiments 1-173, which has an in vitro potency corresponding to an $EC_{50}$ of 75 pM or below.
175. The derivative of any of embodiments 1-174, which has an in vitro potency corresponding to an $EC_{50}$ of 50 pM or below.

176. The derivative of any of embodiments 1-175, which has an in vitro potency corresponding to an $EC_{50}$ of 25 pM or below.
177. The derivative of any of embodiments 1-176, which has an in vitro potency corresponding to an $EC_{50}$ of 15 pM or below.
178. The derivative of any of embodiments 1-177, which has an in vitro potency corresponding to an $EC_{50}$ of 10 pM or below.
179. The derivative of any of embodiments 1-178, wherein the $EC_{50}$ is determined essentially as described in Example 35.
180. The derivative of any of embodiments 1-179, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
181. The derivative of any of embodiments 1-180, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.
182. The derivative of any of embodiments 1-181, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.
183. The derivative of any of embodiments 1-182, which has an in vitro potency corresponding to an $EC_{50}$ of less than 7.5 times the $EC_{50}$ of semaglutide, wherein the $EC_{50}$ of semaglutide is determined in the same way as the $EC_{50}$ of the derivative.
184. The derivative of any of embodiments 1-183, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.
185. The derivative of any of embodiments 1-184, which has an in vitro potency corresponding to an $EC_{50}$ of less than 2.5 times the $EC_{50}$ of semaglutide, wherein the $EC_{50}$ of semaglutide is determined in the same way as the $EC_{50}$ of the derivative.
186. The derivative of any of embodiments 1-185, which has an in vitro potency corresponding to an $EC_{50}$ of less than 1.5 times the $EC_{50}$ of semaglutide, wherein the $EC_{50}$ of semaglutide is determined in the same way as the $EC_{50}$ of the derivative.
187. The derivative of any of embodiments 1-186, wherein the $EC_{50}$ is determined essentially as described in Example 35.
188. The derivative of any of embodiments 1-187, which is capable of binding to the GLP-1 receptor.
189. The derivative of any of embodiments 1-188, which is capable of binding to the GLP-1 receptor at a low concentration of HSA (max. 0.001% final assay concentration).
190. The derivative of any of embodiments 1-189, which is capable of binding to the GLP-1 receptor at a high concentration of HSA (2.0% final assay concentration).
191. The derivative of any of embodiments 1-190, wherein the binding to the human GLP-1 receptor is measured in a competitive binding assay, such as the assay of Example 36.
192. The derivative of any of embodiments 1-191, wherein the binding to the human GLP-1 receptor in vitro is determined essentially as described in Example 36.
193. The derivative of any of embodiments 1-192, which at a low concentration of HSA is capable of binding to the human GLP-1 receptor with an $IC_{50}$ of 5.0 nM or below.
194. The derivative of any of embodiments 1-193, which at a low concentration of HSA is capable of binding to the human GLP-1 receptor with an $IC_{50}$ of 3.0 nM or below.
195. The derivative of any of embodiments 1-194, which at a low concentration of HSA is capable of binding to the human GLP-1 receptor with an $IC_{50}$ of 2.0 nM or below.
196. The derivative of any of embodiments 1-195, which at a low concentration of HSA is capable of binding to the human GLP-1 receptor with an $IC_{50}$ of 1.0 nM or below.
197. The derivative of any of embodiments 1-196, which at a low concentration of HSA is capable of binding to the human GLP-1 receptor with an $IC_{50}$ of 0.5 nM or below.
198. The derivative of any of embodiments 1-197, wherein the $IC_{50}$ is determined essentially as described in Example 36, in a reaction with max. 0.001% HSA (final assay concentration).
199. The derivative of any of embodiments 1-198, which at a low concentration of HSA is capable of binding to the human GLP-1 receptor with an $IC_{50}$ of less than 10 times the $IC_{50}$ of semaglutide, wherein the $IC_{50}$ of semaglutide is determined in the same way as the $IC_{50}$ of the derivative.
200. The derivative of any of embodiments 1-199, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.
201. The derivative of any of embodiments 1-200, which at a low concentration of HSA is capable of binding to the human GLP-1 receptor with an $IC_{50}$ of less than 6 times the $IC_{50}$ of semaglutide, wherein the $IC_{50}$ of semaglutide is determined in the same way as the $IC_{50}$ of the derivative.
202. The derivative of any of embodiments 1-201, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.
203. The derivative of any of embodiments 1-202, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.
204. The derivative of any of embodiments 1-203, which at a low concentration of HSA is capable of binding to the human GLP-1 receptor with an $IC_{50}$ of less than 1.5 times the $IC_{50}$ of semaglutide, wherein the $IC_{50}$ of semaglutide is determined in the same way as the $IC_{50}$ of the derivative.
205. The derivative of any of embodiments 1-204, which at a low concentration of HSA is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.
206. The derivative of any of embodiments 1-205, which at a low concentration of HSA is capable of binding to the human GLP-1 receptor with an $IC_{50}$ of less than 0.6 times the $IC_{50}$ of semaglutide, wherein the $IC_{50}$ of semaglutide is determined in the same way as the $IC_{50}$ of the derivative.

207. The derivative of any of embodiments 1-206, wherein the $IC_{50}$ is determined essentially as described in Example 36, in a reaction with max. 0.001% HSA (final assay concentration).
208. The derivative of any of embodiments 1-207, which at 2.0% HSA (final assay concentration) is capable of binding to the human GLP-1 receptor with an $IC_{50}$ of 300 nM or below.
209. The derivative of any of embodiments 1-208, which at 2.0% HSA (final assay concentration) is capable of binding to the human GLP-1 receptor with an $IC_{50}$ of 125 nM or below.
210. The derivative of any of embodiments 1-209, which at 2.0% HSA (final assay concentration) is capable of binding to the human GLP-1 receptor with an $IC_{50}$ of 75 nM or below.
211. The derivative of any of embodiments 1-210, which at 2.0% HSA (final assay concentration) is capable of binding to the human GLP-1 receptor with an $IC_{50}$ of 50 nM or below.
212. The derivative of any of embodiments 1-211, wherein the $IC_{50}$ is determined essentially as described in Example 36, in a reaction with 2.0% HSA (final assay concentration).
213. The derivative of any of embodiments 1-137, which at 2.0% HSA (final assay concentration) is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.
214. The derivative of any of embodiments 1-138, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.
215. The derivative of any of embodiments 1-139, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.
216. The derivative of any of embodiments 1-140, which at 2.0% HSA (final assay concentration) is capable of binding to the human GLP-1 receptor with an $IC_{50}$ of less than 0.17 times the $IC_{50}$ of semaglutide, wherein the $IC_{50}$ of semaglutide is determined in the same way as the $IC_{50}$ of the derivative.
217. The derivative of any of embodiments 1-216, wherein the $IC_{50}$ is determined essentially as described in Example 36, in a reaction with 2.0% HSA (final assay concentration).
218. The derivative of any of embodiments 1-217, which has improved pharmacokinetic properties.
219. The derivative of any of embodiments 1-218, which has an increased half-life and/or a decreased clearance.
220. The derivative of any of embodiments 1-219, which is suitable for once-monthly administration.
221. The derivative of any of embodiments 1-220, for s.c. administration.
222. The derivative of any of embodiments 1-221, wherein the derivative is tested in vivo in pharmacokinetic (PK) studies.
223. The derivative of any of embodiments 1-222, wherein the derivative is tested in any suitable animal model, such as mouse, rat, monkey, dog, or pig.
224. The derivative of any of embodiments 1-223, which is compared with semaglutide.
225. The derivative of any of embodiments 1-224, which has an improved terminal half-life (T½) in vivo in minipigs after i.v. administration as compared to semaglutide.
226. The derivative of any of embodiments 1-225, wherein the terminal half-life is determined in vivo in minipigs after i.v. administration using any suitable study protocol, such as the one described in Example 37.
227. The derivative of any of embodiments 1-226, wherein the terminal half-life is determined in vivo in minipigs after i.v. administration, essentially as described in Example 37.
228. The derivative of any of embodiments 1-227, which has a terminal half-life (T½) in vivo in minipigs after i.v. administration of at least 100 hours.
229. The derivative of any of embodiments 1-228, which has a terminal half-life (T½) in vivo in minipigs after i.v. administration of at least 125 hours.
230. The derivative of any of embodiments 1-229, which has a terminal half-life (T½) in vivo in minipigs after i.v. administration of at least 150 hours.
231. The derivative of any of embodiments 1-230, which has a terminal half-life (T½) in vivo in minipigs after i.v. administration of at least 175 hours.
232. The derivative of any of embodiments 1-231, which has a terminal half-life (T½) in vivo in minipigs after i.v. administration of at least 2.1 times the terminal half-life of semaglutide, determined in the same way.
233. The derivative of any of embodiments 1-232, which has a terminal half-life (T½) in vivo in minipigs after i.v. administration of at least 2.5 times the terminal half-life of semaglutide, determined in the same way.
234. The derivative of any of embodiments 1-233, which has a terminal half-life (T½) in vivo in minipigs after i.v. administration of at least 2.8 times the terminal half-life of semaglutide, determined in the same way.
235. The derivative of any of embodiments 1-234, which has a terminal half-life (T½) in vivo in minipigs after i.v. administration of at least 3.3 times the terminal half-life of semaglutide, determined in the same way.
236. The derivative of any of embodiments 1-235, which is potent in vivo.
237. The derivative of any of embodiments 1-236, which is potent in vivo when determined in any suitable animal model, such as mouse or pig.
238. The derivative of any of embodiments 1-237, wherein the animal model is db/db mouse.
239. The derivative of any of embodiments 1-238, wherein the blood glucose lowering effect is determined.
240. The derivative of any of embodiments 1-239, wherein the body weight lowering effect is determined.
241. The derivative of any of embodiments 1-240, wherein blood glucose lowering effect and/or body weight lowering effect is determined in vivo in db/db mouse using any suitable study protocol and methodology, e.g. as described in Example 38.
242. The derivative of any of embodiments 1-241, wherein the blood glucose lowering effect and/or the body weight lowering effect is determined in vivo in db/db mouse, essentially as described in Example 38.
243. The derivative of any of embodiments 1-242, which has the effect in vivo of reducing blood glucose after 48 hours, determined in a single-dose study in a db/db mouse model.

244. The derivative of any of embodiments 1-243, wherein the blood glucose is reduced by at least 15%, as compared to the blood glucose level before administration of the derivative.
245. The derivative of any of embodiments 1-244, wherein the blood glucose is reduced by at least 30%, as compared to the blood glucose level before administration of the derivative.
246. The derivative of any of embodiments 1-245, wherein the blood glucose is reduced by at least 45%, as compared to the blood glucose level before administration of the derivative.
247. The derivative of any of embodiments 1-246, wherein the blood glucose is reduced by at least 60%, as compared to the blood glucose level before administration of the derivative.
248. The derivative of any of embodiments 1-247, which has the effect in vivo of reducing blood glucose after 72 hours, determined in a single-dose study in a db/db mouse model.
249. The derivative of any of embodiments 1-248, which has the effect in vivo of reducing blood glucose after 96 hours, determined in a single-dose study in a db/db mouse model.
250. The derivative any of embodiments 1-249, wherein the blood glucose is reduced by at least 15%, as compared to the blood glucose level before administration of the derivative.
251. The derivative of any of embodiments 1-250, wherein the blood glucose is reduced by at least 10%, as compared to the blood glucose level before administration of the derivative.
252. The derivative of any of embodiments 1-251, wherein the blood glucose is reduced by at least 15%, as compared to the blood glucose level before administration of the derivative.
253. The derivative of any of embodiments 1-252, wherein the blood glucose is reduced by at least 20%, as compared to the blood glucose level before administration of the derivative.
254. The derivative of any of embodiments 1-253, wherein the blood glucose is reduced by at least 40%, as compared to the blood glucose level before administration of the derivative.
255. The derivative of any of embodiments 1-254, which has the effect in vivo of reducing body weight after 48 hours, determined in a single-dose study in a db/db mouse model.
256. The derivative of any of embodiments 1-255, wherein the body weight is reduced by at least 2%, as compared to the body weight before administration of the derivative.
257. The derivative of any of embodiments 1-256, wherein the body weight is reduced by at least 4%, as compared to the body weight before administration of the derivative.
258. The derivative of any of embodiments 1-257, wherein the body weight is reduced by at least 5%, as compared to the body weight before administration of the derivative.
259. The derivative of any of embodiments 1-258, wherein the body weight is reduced by at least 6%, as compared to the body weight before administration of the derivative.
260. The derivative of any of embodiments 1-259, which has the effect in vivo of reducing body weight after 72 hours, determined in a single-dose study in a db/db mouse model.
261. The derivative of any of embodiments 1-260 which has the effect in vivo of reducing body weight after 96 hours, determined in a single-dose study in a db/db mouse model.
262. The derivative of any of embodiments 1-261, wherein the body weight is reduced by at least 1%, as compared to the body weight before administration of the derivative.
263. The derivative of any of embodiments 1-262, wherein the body weight is reduced by at least 3%, as compared to the body weight before administration of the derivative.
264. The derivative of any of embodiments 1-263, wherein the body weight is reduced by at least 4%, as compared to the body weight before administration of the derivative.
265. The derivative of any of embodiments 1-264, wherein the body weight is reduced by at least 5%, as compared to the body weight before administration of the derivative.
266. The derivative of any of embodiments 1-265, wherein the body weight is reduced by at least 6%, as compared to the body weight before administration of the derivative.
267. The derivative of any of embodiments 1-266, wherein the animal model is pig.
268. The derivative any of embodiments 1-267, wherein the animal model is LYD pig.
269. The derivative of any of embodiments 1-268, wherein the reduction in food intake is determined in an in vivo pharmacodynamic (PD) study.
270. The derivative of any of embodiments 1-269, wherein the reduction in food intake is determined in vivo in pig using any suitable study protocol and methodology, e.g. as described in Example 39.
271. The derivative of any of embodiments 1-270, wherein the reduction in food intake is determined in vivo in pig using any suitable study protocol and methodology, essentially as described in Example 39.
272. The derivative of any of embodiments 1-271, which has the effect in vivo of reducing food intake during a first period of 24 hours (0-24 hours) after administration of a single dose of the derivative, wherein food intake is determined in a single-dose study in a LYD pig model.
273. The derivative of any of embodiments 1-272, which has the effect in vivo of reducing food intake during a second period of 24 hours (24-48 hours) after administration of a single dose of the derivative, wherein food intake is determined in a single-dose study in a LYD pig model.
274. The derivative of any of embodiments 1-273, which has the effect in vivo of reducing food intake during a third period of 24 hours (48-72 hours) after administration of a single dose of the derivative, wherein food intake is determined in a single-dose study in a LYD pig model.
275. The derivative of any of embodiments 1-274, which has the effect in vivo of reducing food intake during a fourth period of 24 hours (72-96 hours) after administration of a single dose of the derivative, wherein food intake is determined in a single-dose study in a LYD pig model.
276. A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, Chem. 40, Chem. 41, Chem. 42, Chem. 43, Chem. 44, Chem. 45, Chem. 46, Chem. 47, Chem. 48, Chem. 49, Chem. 50, Chem. 51, Chem. 52, Chem. 53, and Chem. 54; or a pharmaceutically acceptable salt, amide, or ester thereof.
277. A GLP-1 derivative selected from the chemical structures shown in any of Examples 1-34, preferably 1-20; or a pharmaceutically acceptable salt, amide, or ester thereof.

278. A GLP-1 derivative selected from the GLP-1 derivative names shown in any of Examples 1-34, preferably 1-20; or a pharmaceutically acceptable salt, amide, or ester thereof.

279. The derivative of any of embodiments 276-278, which is a derivative according to any of embodiments 1-275.

280. An intermediate product in the form of a GLP-1 analogue, which comprises the following amino acid changes when compared to GLP-1 (7-37) (SEQ ID NO: 1): iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii) (8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), or xvii) (8Aib, 22E, 26R, 34R, 37P, 38K) (SEQ ID NO: 18).

281. An intermediate product in the form of a GLP-1 analogue, which comprises the following amino acid changes when compared to GLP-1 (7-37) (SEQ ID NO: 1): 40K, 41K, 42K, or 43K.

282. The intermediate product of any of embodiments 280-281, which is a GLP-1 peptide of formula I as defined in embodiment 1.

283. The intermediate product of any of embodiments 280-282, which is a GLP-1 peptide as defined in any of embodiments 66-162.

284. An intermediate product in the form of a GLP-1 analogue, selected from the following analogues of GLP-1 (7-37) (SEQ ID NO: 1): i) (8Aib, 22E, 26R, 27K, 34R) (SEQ ID NO: 10), iii) (8Aib, 22E, 26R, 34R, 38G, 39G, 40G, 41S, 42K) (SEQ ID NO: 2), iv) (8Aib, 22E, 26R, 34R, 38G, 39G, 40S, 41K) (SEQ ID NO: 3), v) (8Aib, 22E, 26R, 34R, 38G, 39S, 40K) (SEQ ID NO: 4), vii) (8Aib, 22E, 26R, 34R, 38S, 39K) (SEQ ID NO: 5), viii) (8Aib, 22E, 26R, 34R, 38S, 39S, 40G, 41A, 42P, 43K) (SEQ ID NO: 9), ix) (8Aib, 26R, 34R, 38K) (SEQ ID NO: 8), x) (8Aib, 22E, 26R, 34R, 38A, 39E, 40A, 41P, 42K) (SEQ ID NO: 11), xi) (8Aib, 22E, 26R, 34R, 38E, 39P, 40P, 41G, 42K) (SEQ ID NO: 12), xii) (8Aib, 22E, 26R, 34R, 38P, 39A, 40E, 41E, 42K) (SEQ ID NO: 13), xiii) (8Aib, 22E, 26R, 34R, 38S, 39S, 40P, 41A, 42A, 43K) (SEQ ID NO: 14), xiv) (8Aib, 22E, 26R, 34R, 38S, 39S, 40A, 41E, 42G, 43K) (SEQ ID NO: 15), xv) (8Aib, 22E, 26R, 34R, 38S, 39S, 40E, 41A, 42E, 43K) (SEQ ID NO: 16), xvi) (7Imp, 8Aib, 22E, 26R, 34R, 38G, 39K) (SEQ ID NO: 17), and xvii) (8Aib, 22E, 26R, 34R, 37P, 38K) (SEQ ID NO: 18).

285. A pharmaceutical composition comprising a derivative according to any of embodiments 1-279, or an analogue according to any of embodiments 280-284, and a pharmaceutically acceptable excipient.

286. A derivative according to any of embodiments 1-279, or an analogue according to any of embodiments 280-284, for use as a medicament.

287. A derivative according to any of embodiments 1-279, or an analogue according to any of embodiments 280-284, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

288. Use of a derivative according to any of embodiments 1-279, or an analogue according to any of embodiments 280-284, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

289. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-279, or an analogue according to any of embodiments 280-284, is administered.

Additional Particular Embodiments

The following are additional particular sets of particular embodiments of the invention:

i). A derivative of a GLP-1 peptide, wherein the GLP-1 peptide is of formula I:

Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$, wherein Xaa$_7$ is L-histidine, (S)-2-Hydroxy-3-(1H-imidazol-4-yl)-propionic acid, D-histidine, desamino-histidine, homohistidine, N$^\alpha$-acetyl-histidine, N$^\alpha$-formyl-histidine, α-methyl-histidine, 3-pyridylalanine, 2-pyridylalanine, or 4-pyridylalanine; Xaa$_8$ is Ala, Gly, Ser, Aib, (1-aminocyclopropyl) carboxylic acid, or (1-aminocyclobutyl) carboxylic acid; Xaa$_{12}$ is Phe or Leu; Xaa$_{16}$ is Val or Leu; Xaa$_{18}$ is Ser, Val, Lys, Arg, or Leu; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg or Lys; Xaa$_{27}$ is Glu, Lys or Leu; Xaa$_{30}$ is Ala, Glu, or Arg; Xaa$_{31}$ is Trp or His; Xaa$_{33}$ is Val, Lys, or Arg; Xaa$_{34}$ is Arg, Lys, His, Asn, or Gln; Xaa$_{35}$ is Gly or Ala; Xaa$_{36}$ is Arg or Gly; Xaa$_{37}$ is Gly, Pro, or Lys; Xaa$_{38}$ is Ser, Gly, Ala, Glu, Pro, Lys, or absent; Xaa$_{39}$ is Ser, Gly, Ala, Glu, Pro, Lys, or absent; Xaa$_{40}$ is Ser, Gly, Ala, Glu, Pro, Lys, or absent; Xaa$_{41}$ is Ser, Gly, Ala, Glu, Pro, Lys, or absent; Xaa$_{42}$ is Ser, Gly, Ala, Glu, Pro, Lys, or absent; and Xaa$_{43}$ is Ser, Gly, Ala, Glu, Pro, Lys, or absent; which GLP-1 peptide comprises a Lys residue at a position corresponding to position 27, 37, 38, 39, 40, 41, 42, or 43 of GLP-1(7-37) (SEQ ID NO: 1); which derivative comprises a first and a second protracting moiety of formula Chem. 1:

HOOC—(CH$_2$)$_{18}$—CO—*;   Chem. 1:

a branched linker of formula Chem. 2:

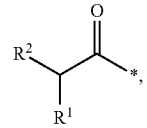

Chem. 2 wherein

R$^1$ is —(CH$_2$)$_q$—NH—*, wherein q is an integer in the range of 0-5,

R$^2$ is —(CH$_2$)$_w$—NH—*, wherein w is an integer in the range of 0-5, with the provisos that when w is 0 q is an integer in the range of 1-5, and when q is 0 w is an integer in the range of 1-5; and a first and a second further linker, each comprising an element_1 of formula Chem. 3:

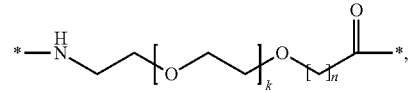

Chem. 3 wherein k is an integer in the range of 1-5, and n is an integer in the range of 1-5;

wherein the first protracting moiety is attached at its *—CO end to a first *—NH end of the branched linker, via the first further linker, the second protracting moiety is attached at its *—CO end to a second *—NH end of the branched linker, via the second further linker; and the branched linker is attached at its *—CO end to the epsilon amino group of the Lys residue of the GLP-1 peptide;

or a pharmaceutically acceptable salt, amide, or ester thereof.

ii). The derivative of embodiment i) 1, wherein q=4 and w=0.

iii). The derivative of any of embodiments i)-ii), wherein the first further linker and the second further linker each comprises an element_2 of formula Chem. 4:

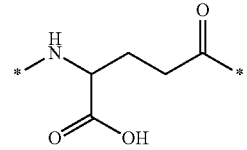

Chem. 4 iv). The derivative of any of embodiments i)-iii), wherein the first further linker and the second further linker each comprises an element_3 of formula Chem. 5:

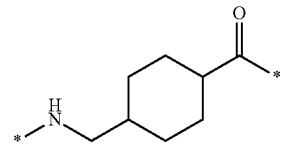

Chem. 5 v). The derivative of any of embodiments i)-iii), wherein the first further linker and the second further linker each comprises an element_4 of formula Chem. 6:

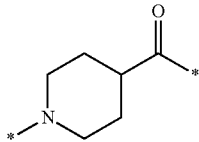

Chem. 6 vi). The derivative of any of embodiments i)-v), which comprises a Lys residue at a position corresponding to position 27 of GLP-1(7-37) (SEQ ID NO: 1).
vii). The derivative of any of embodiments i)-v), which comprises a Lys residue at a position corresponding to position 37 of GLP-1(7-37) (SEQ ID NO: 1).
iix). The derivative of any of embodiments i)-v), which comprises a Lys residue at a position corresponding to position 27 or 37 of GLP-1(7-37) (SEQ ID NO: 1) and which incorporates five elements_1 of formula Chem. 3.
ix). The derivative of any of embodiments i)-v), wherein the GLP-1 peptide is selected from the following analogues of GLP-1 (7-37) (SEQ ID NO: 1): i) (8Aib, 22E, 26R, 27K, 34R), ii) (8Aib, 22E, 26R, 34R, 37K), iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vi) (8Aib, 22E, 26R, 34R, 38K), vii) (8Aib, 22E, 26R, 34R, 38S, 39K), viii) (8Aib, 22E, 26R, 34R, 38S, 39S, 40G, 41A, 42P, 43K), and ix) (8Aib, 26R, 34R, 38K).
x). A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, and Chem. 40; or a pharmaceutically acceptable salt, amide, or ester thereof.
xi). The derivative of any of embodiments i)-x), in the form of a sodium or potassium salt thereof.
xii). An intermediate product in the form of a GLP-1 analogue, which comprises the following amino acid changes when compared to GLP-1 (7-37) (SEQ ID NO: 1): iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vii) (8Aib, 22E, 26R, 34R, 38S, 39K), and viii) (8Aib, 22E, 26R, 34R, 38S, 39S, 40G, 41A, 42P, 43K).
xiii). An intermediate product in the form of a GLP-1 analogue, selected from the following analogues of GLP-1 (7-37) (SEQ ID NO: 1): i) (8Aib, 22E, 26R, 27K, 34R), iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vii) (8Aib, 22E, 26R, 34R, 38S, 39K), and viii) (8Aib, 22E, 26R, 34R, 38S, 39S, 40G, 41A, 42P, 43K).
xiv). A derivative according to any of embodiments i)-xi), or an analogue according to any of embodiments xii)-xiii), for use as a medicament.
xv). A derivative according to any of embodiments i)-xi), or an analogue according to any of embodiments xii)-xiii), for use in
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders and/or neurodegenerative disorders, such as Alzheimer's disease, Parkinson's disease, and/or multiple sclerosis;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(vi) prevention and/or treatment of diabetic complications, such as angiopathy; neuropathy, including peripheral neuropathy; nephropathy; and/or retinopathy;
(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;
(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;
(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;
(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;
(xi) prevention and/or treatment of polycystic ovary syndrome (PCOS);

(xii) prevention and/or treatment of cerebral disease, such as cerebral ischemia, cerebral haemorrhage, and/or traumatic brain injury;
(xiii) prevention and/or treatment of sleep apnoea; and/or
(xiv) prevention and/or treatment of abuse, such as alcohol abuse and/or drug abuse.

1. A derivative of a GLP-1 peptide,
wherein the GLP-1 peptide is of formula I:
Formula I:
   $Xaa_7$-$Xaa_8$-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$,
wherein
   $Xaa_7$ is L-histidine, (S)-2-Hydroxy-3-(1H-imidazol-4-yl)-propionic acid, D-histidine, desamino-histidine, homohistidine, $N^\alpha$-acetyl-histidine, $N^\alpha$-formyl-histidine, α-methyl-histidine, 3-pyridylalanine, 2-pyridylalanine, or 4-pyridylalanine;
   $Xaa_8$ is Ala, Gly, Ser, Aib, (1-aminocyclopropyl) carboxylic acid, or (1-aminocyclobutyl) carboxylic acid;
   $Xaa_{12}$ is Phe or Leu;
   $Xaa_{16}$ is Val or Leu;
   $Xaa_{18}$ is Ser, Val, Lys, Arg, or Leu;
   $Xaa_{19}$ is Tyr or Gln;
   $Xaa_{20}$ is Leu or Met;
   $Xaa_{22}$ is Gly or Glu;
   $Xaa_{23}$ is Gln, Glu, or Arg;
   $Xaa_{25}$ is Ala or Val;
   $Xaa_{26}$ is Arg or Lys;
   $Xaa_{27}$ is Glu, Lys or Leu;
   $Xaa_{30}$ is Ala, Glu, or Arg;
   $Xaa_{31}$ is Trp or His;
   $Xaa_{33}$ is Val, Lys, or Arg;
   $Xaa_{34}$ is Arg, Lys, His, Asn, or Gln;
   $Xaa_{35}$ is Gly or Ala;
   $Xaa_{36}$ is Arg or Gly;
   $Xaa_{37}$ is Gly, Pro, or Lys;
   $Xaa_{38}$ is Ser, Gly, Ala, Glu, Pro, Lys, or absent;
   $Xaa_{39}$ is Ser, Gly, Ala, Glu, Pro, Lys, or absent;
   $Xaa_{40}$ is Ser, Gly, Ala, Glu, Pro, Lys, or absent;
   $Xaa_{41}$ is Ser, Gly, Ala, Glu, Pro, Lys, or absent;
   $Xaa_{42}$ is Ser, Gly, Ala, Glu, Pro, Lys, or absent; and
   $Xaa_{43}$ is Ser, Gly, Ala, Glu, Pro, Lys, or absent;
which GLP-1 peptide comprises a Lys residue at a position corresponding to position 27, 37, 38, 39, 40, 41, 42, or 43 of GLP-1(7-37) (SEQ ID NO: 1);
which derivative comprises
a first and a second protracting moiety of formula Chem. 1:

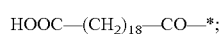
Chem. 1:

a branched linker of formula Chem. 2:

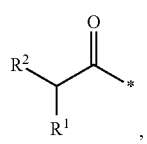
Chem. 2 wherein
$R^1$ is —$(CH_2)_q$—NH—*, wherein q is an integer in the range of 0-5,
$R^2$ is —$(CH_2)_w$—NH—*, wherein w is an integer in the range of 0-5,
with the provisos that when w is 0 q is an integer in the range of 1-5, and when q is 0 w is an integer in the range of 1-5; and
a first and a second further linker, each comprising an element_1 of formula Chem. 3:

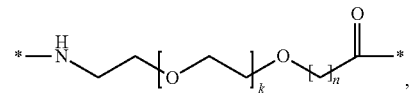
Chem. 3 wherein k is an integer in the range of 1-5, and n is an integer in the range of 1-5;
wherein
   the first protracting moiety is attached at its *—CO end to a first *—NH end of the branched linker, via the first further linker,
   the second protracting moiety is attached at its *—CO end to a second *—NH end of the branched linker, via the second further linker; and
   the branched linker is attached at its *—CO end to the epsilon amino group of the Lys residue of the GLP-1 peptide;
or a pharmaceutically acceptable salt, amide, or ester thereof.

2. The derivative of embodiment 1, wherein q=4 and w=0.
3. The derivative of any of embodiments 1-2, wherein Chem. 2 represents eps-Lys(Bis).
4. The derivative of any of embodiments 1-3, wherein the first further linker and the second further linker each comprises at least one element_1 of formula Chem. 3.
5. The derivative of any of embodiments 1-4, wherein the first further linker and the second further linker each comprises at least two elements_1 of formula Chem. 3.
6. The derivative of any of embodiments 1-5, wherein the first further linker and the second further linker each comprises at least three elements_1 of formula Chem. 3.
7. The derivative of any of embodiments 1-6, wherein the first further linker and the second further linker each comprises at least four elements_1 of formula Chem. 3.
8. The derivative of any of embodiments 1-7, wherein the first further linker and the second further linker each comprises at least five elements_1 of formula Chem. 3.
9. The derivative of any of embodiments 1-5, wherein the first further linker and the second further linker each incorporates two elements_1 of formula Chem. 3.
10. The derivative of any of embodiments 1-6, wherein the first further linker and the second further linker each incorporates three elements_1 of formula Chem. 3.
11. The derivative of any of embodiments 1-7, wherein the first further linker and the second further linker each incorporates four elements_1 of formula Chem. 3.
12. The derivative of any of embodiments 1-8, wherein the first further linker and the second further linker each incorporates five elements_1 of formula Chem. 3.
13. The derivative of any of embodiments 1-12, wherein k=1 and n=1.
14. The derivative of any of embodiments 1-13, wherein Chem. 3 represents OEG.
15. The derivative of any of embodiments 1-14, wherein the first further linker and the second further linker each incorporates an *—NH or *—N group, and a *—CO group.

16. The derivative of any of embodiments 1-15, wherein
an amide bond connects the *—CO end of the first protracting moiety to the *—NH or *—N end of the first further linker, and an amide bond connects the *—CO end of the first further linker to the first *—NH end of the branched linker; and
an amide bond connects the *—CO end of the second protracting moiety to the *—NH or *—N end of the second further linker, and an amide bond connects the *—CO end of the second further linker to the second *—NH end of the branched linker.

17. The derivative of any of embodiments 1-16, wherein the first further linker and the second further linker each comprises an element_2 of formula Chem. 4:

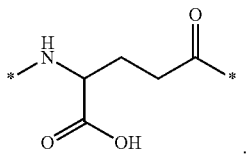

Chem. 4

18. The derivative of embodiment 17, wherein the first further linker and the second further linker each incorporates one element_2 of formula Chem. 4:

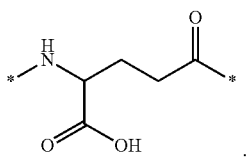

Chem. 4

19. The derivative of any of embodiments 17-18, wherein Chem. 4 represents gGlu.
20. The derivative of any of embodiments 17-19, wherein Chem. 4 represents the L-form of gGlu.
21. The derivative of any of embodiments 1-20, wherein the first further linker and the second further linker each comprises an element_3 of formula Chem. 5:

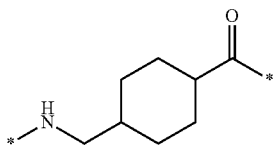

Chem. 5

22. The derivative of any of embodiments 1-21, wherein the first further linker and the second further linker each incorporates one element_3 of formula Chem. 5:

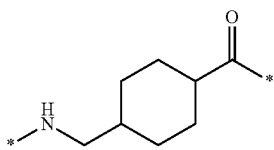

Chem. 5

23. The derivative of any of embodiments 21-22, wherein Chem. 5 represents Trx.
24. The derivative of any of embodiments 1-23, wherein the first further linker and the second further linker each comprises an element_4 of formula Chem. 6:

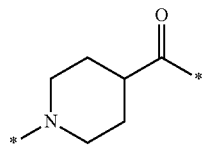

Chem. 6

25. The derivative of any of embodiments 1-24, wherein the first further linker and the second further linker each incorporates one element_4 of formula Chem. 6:

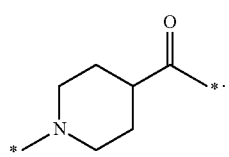

Chem. 6

26. The derivative of any of embodiments 24-25, wherein Chem. 6 represents Inp.
27. The derivative of any of embodiments 1-26, wherein the first further linker and the second further linker each consists of one element_2 of formula Chem. 4, and two elements_1 of formula Chem. 3 wherein k=1 and n=1, interconnected via amide bonds and in the sequence indicated.
28. The derivative of any of embodiments 1-26, wherein the first further linker and the second further linker each consists of one element_4 of formula Chem. 6, one element_2 of formula Chem. 4, and two elements_1 of formula Chem. 3 wherein k=1 and n=1, interconnected via amide bonds and in the sequence indicated.
29. The derivative of any of embodiments 1-26, wherein the first further linker and the second further linker each consists of one element_3 of formula Chem. 5, one element_2 of formula Chem. 4, and two elements_1 of formula Chem. 3 wherein k=1 and n=1, interconnected via amide bonds and in the sequence indicated.
30. The derivative of any of embodiments 1-26, wherein the first further linker and the second further linker each consists of one element_3 of formula Chem. 5, one element_2 of formula Chem. 4, and three elements_1 of formula Chem. 3 wherein k=1 and n=1, interconnected via amide bonds and in the sequence indicated.
31. The derivative of any of embodiments 1-26, wherein the first further linker and the second further linker each consists of one element 3 of formula Chem. 5, one element_2 of formula Chem. 4, and four elements_1 of formula Chem. 3 wherein k=1 and n=1, interconnected via amide bonds and in the sequence indicated.
32. The derivative of any of embodiments 1-26, wherein the first further linker and the second further linker each consists of one element_3 of formula Chem. 5, one element_2 of formula Chem. 4, and five elements_1 of formula Chem. 3 wherein k=1 and n=1, interconnected via amide bonds and in the sequence indicated.

33. The derivative of any of embodiments 1-32 which comprises a Lys residue at a position corresponding to position 27 of GLP-1(7-37) (SEQ ID NO: 1).
34. The derivative of any of embodiments 1-32 which comprises a Lys residue at a position corresponding to position 37 of GLP-1(7-37) (SEQ ID NO: 1).
35. The derivative of any of embodiments 1-32 which comprises a Lys residue at a position corresponding to position 38 of GLP-1(7-37) (SEQ ID NO: 1).
36. The derivative of any of embodiments 1-32 which comprises a Lys residue at a position corresponding to position 39 of GLP-1(7-37) (SEQ ID NO: 1).
37. The derivative of any of embodiments 1-32 which comprises a Lys residue at a position corresponding to position 40 of GLP-1(7-37) (SEQ ID NO: 1).
38. The derivative of any of embodiments 1-32 which comprises a Lys residue at a position corresponding to position 41 of GLP-1(7-37) (SEQ ID NO: 1).
39. The derivative of any of embodiments 1-32 which comprises a Lys residue at a position corresponding to position 42 of GLP-1(7-37) (SEQ ID NO: 1).
40. The derivative of any of embodiments 1-32 which comprises a Lys residue at a position corresponding to position 43 of GLP-1(7-37) (SEQ ID NO: 1).
41. The derivative of any of embodiments 1-32 which comprises a Lys residue at a position corresponding to position 27 or 37 of GLP-1(7-37) (SEQ ID NO: 1) and which incorporates five elements_1 of formula Chem. 3.
42. The derivative of embodiment 41 which further incorporates one element_2 of formula Chem. 4.
43. The derivative of any of embodiments 41 or 42 which further incorporates one element_3 of formula Chem. 5.
44. The derivative of any of embodiments 1-32 which comprises a Lys residue at a position corresponding to position 38, 39, 40, 41, 42, or 43 of GLP-1(7-37) (SEQ ID NO: 1) and which incorporates two to four elements_1 of formula Chem. 3.
45. The derivative of embodiment 44 which further incorporates one element_2 of formula Chem. 4.
46. The derivative of any of embodiments 44 or 45 which further incorporates one element_3 of formula Chem. 5, or one element_4 of formula Chem. 6.
47. The derivative of any of embodiments 1-46, wherein if $Xaa_{42}$ is absent, then $Xaa_{43}$ is also absent.
48. The derivative of any of embodiments 1-47, wherein if $Xaa_{41}$ is absent, then $Xaa_{42}$ and $Xaa_{43}$ is also absent.
49. The derivative of any of embodiments 1-48, wherein if $Xaa_{40}$ is absent, then $Xaa_{41}$, $Xaa_{42}$, and $Xaa_{43}$ are also absent.
50. The derivative of any of embodiments 1-49, wherein if $Xaa_{39}$ is absent, then $Xaa_{40}$, $Xaa_{41}$, $Xaa_{42}$, and $Xaa_{43}$ are also absent.
51. The derivative of any of embodiments 1-50, wherein if $Xaa_{38}$ is absent, then $Xaa_{39}$, $Xaa_{40}$, $Xaa_{41}$, $Xaa_{42}$, and $Xaa_{43}$ are also absent.
52. The derivative of any of embodiments 1-51, wherein $Xaa_7$ is His.
53. The derivative of any of embodiments 1-52, wherein $Xaa_8$ is Aib.
54. The derivative of any of embodiments 1-53, wherein $Xaa_{12}$ is Phe.
55. The derivative of any of embodiments 1-54, wherein $Xaa_{16}$ is Val.
56. The derivative of any of embodiments 1-55, wherein $Xaa_{18}$ is Ser.
57. The derivative of any of embodiments 1-56, wherein $Xaa_{19}$ is Tyr.
58. The derivative of any of embodiments 1-57, wherein $Xaa_{20}$ is Leu.
59. The derivative of any of embodiments 1-58, wherein $Xaa_{22}$ is Gly.
60. The derivative of any of embodiments 1-58, wherein $Xaa_{22}$ is Glu.
61. The derivative of any of embodiments 1-60, wherein $Xaa_{23}$ is Gln.
62. The derivative of any of embodiments 1-61, wherein $Xaa_{25}$ is Ala.
62a. The derivative of any of embodiments 1-62, wherein $Xaa_{26}$ is Arg.
63. The derivative of any of embodiments 1-62a, wherein $Xaa_{27}$ is Glu.
64. The derivative of any of embodiments 1-62, wherein $Xaa_{27}$ is Lys.
65. The derivative of any of embodiments 1-64, wherein $Xaa_{30}$ is Ala.
66. The derivative of any of embodiments 1-65, wherein $Xaa_{31}$ is Trp.
67. The derivative of any of embodiments 1-66, wherein $Xaa_{33}$ is Val.
68. The derivative of any of embodiments 1-67, wherein $Xaa_{34}$ is Arg.
69. The derivative of any of embodiments 1-68, wherein $Xaa_{35}$ is Gly.
70. The derivative of any of embodiments 1-69, wherein $Xaa_{36}$ is Arg.
71. The derivative of any of embodiments 1-70, wherein $Xaa_{37}$ is Gly.
72. The derivative of any of embodiments 1-70, wherein $Xaa_{37}$ is Lys.
73. The derivative of any of embodiments 1-72, wherein $Xaa_{38}$ is Ser.
74. The derivative of any of embodiments 1-72, wherein $Xaa_{38}$ is Gly.
75. The derivative of any of embodiments 1-72, wherein $Xaa_{38}$ is Lys.
76. The derivative of any of embodiments 1-72, wherein $Xaa_{38}$ is absent.
77. The derivative of any of embodiments 1-76, wherein $Xaa_{39}$ is Ser.
78. The derivative of any of embodiments 1-76, wherein $Xaa_{39}$ is Gly.
79. The derivative of any of embodiments 1-76, wherein $Xaa_{39}$ is Lys.
80. The derivative of any of embodiments 1-76, wherein $Xaa_{39}$ is absent.
81. The derivative of any of embodiments 1-80, wherein $Xaa_{40}$ is Ser.
82. The derivative of any of embodiments 1-80, wherein $Xaa_{40}$ is Gly.
83. The derivative of any of embodiments 1-80, wherein $Xaa_{40}$ is Lys.
84. The derivative of any of embodiments 1-80, wherein $Xaa_{40}$ is absent.
85. The derivative of any of embodiments 1-84, wherein $Xaa_{41}$ is Ser.
86. The derivative of any of embodiments 1-84, wherein $Xaa_{41}$ is Ala.
87. The derivative of any of embodiments 1-84, wherein $Xaa_{41}$ is Lys.
88. The derivative of any of embodiments 1-84, wherein $Xaa_{41}$ is absent.
89. The derivative of any of embodiments 1-88, wherein $Xaa_{42}$ is Pro.

90. The derivative of any of embodiments 1-88, wherein $Xaa_{42}$ is Lys.
91. The derivative of any of embodiments 1-88, wherein $Xaa_{42}$ is absent.
92. The derivative of any of embodiments 1-91, wherein $Xaa_{43}$ is Lys.
93. The derivative of any of embodiments 1-91, wherein $Xaa_{43}$ is absent.
93a. The derivative of any of embodiments 1-93, wherein the GLP-1 peptide has a maximum of 12 amino acid changes, when compared with GLP-1(7-37) (SEQ ID NO: 1).
93b. The derivative of any of embodiments 1-93a, wherein the GLP-1 peptide has a maximum of 11 amino acid changes, when compared with GLP-1(7-37) (SEQ ID NO: 1).
93c. The derivative of any of embodiments 1-93b, wherein the GLP-1 peptide has a maximum of 10 amino acid changes, when compared with GLP-1(7-37) (SEQ ID NO: 1).
93d. The derivative of any of embodiments 1-93c, wherein the GLP-1 peptide has a maximum of 9 amino acid changes, when compared with GLP-1(7-37) (SEQ ID NO: 1).
93e. The derivative of any of embodiments 1-93d, wherein the GLP-1 peptide has a maximum of 8 amino acid changes, when compared with GLP-1(7-37) (SEQ ID NO: 1).
93f. The derivative of any of embodiments 1-93e, wherein the GLP-1 peptide has a maximum of 7 amino acid changes, when compared with GLP-1(7-37) (SEQ ID NO: 1).
93g. The derivative of any of embodiments 1-93f, wherein the GLP-1 peptide has a maximum of 6 amino acid changes, when compared with GLP-1(7-37) (SEQ ID NO: 1).
93h. The derivative of any of embodiments 1-93g, wherein the GLP-1 peptide has a maximum of 5 amino acid changes, when compared with GLP-1(7-37) (SEQ ID NO: 1).
93i. The derivative of any of embodiments 1-93h, wherein the GLP-1 peptide has a maximum of 4 amino acid changes, when compared with GLP-1(7-37) (SEQ ID NO: 1).
93j. The derivative of any of embodiments 1-93i, wherein the GLP-1 peptide has a maximum of 3 amino acid changes, when compared with GLP-1(7-37) (SEQ ID NO: 1).
93k. The derivative of any of embodiments 1-93j, wherein the GLP-1 peptide has a maximum of 2 amino acid changes, when compared with GLP-1(7-37) (SEQ ID NO: 1).
93l. The derivative of any of embodiments 1-93k, wherein the GLP-1 peptide has a maximum of 1 amino acid changes, when compared with GLP-1(7-37) (SEQ ID NO: 1).
93m. The derivative of any of embodiments 1-93l, wherein the GLP-1 peptide has a minimum of 1 amino acid change, when compared with GLP-1(7-37) (SEQ ID NO: 1).
93n. The derivative of any of embodiments 1-93m, wherein the GLP-1 peptide has a minimum of 2 amino acid changes, when compared with GLP-1(7-37) (SEQ ID NO: 1).
93o. The derivative of any of embodiments 1-93n, wherein the GLP-1 peptide has a minimum of 3 amino acid changes, when compared with GLP-1(7-37) (SEQ ID NO: 1).
93p. The derivative of any of embodiments 1-93o, wherein the GLP-1 peptide has a minimum of 4 amino acid changes, when compared with GLP-1(7-37) (SEQ ID NO: 1).
93q. The derivative of any of embodiments 1-93p, wherein the GLP-1 peptide has a minimum of 5 amino acid changes, when compared with GLP-1(7-37) (SEQ ID NO: 1).
93r. The derivative of any of embodiments 1-93q, wherein the GLP-1 peptide has a minimum of 6 amino acid changes, when compared with GLP-1(7-37) (SEQ ID NO: 1).
93s. The derivative of any of embodiments 1-93r, wherein the GLP-1 peptide has a minimum of 7 amino acid changes, when compared with GLP-1(7-37) (SEQ ID NO: 1).
93t. The derivative of any of embodiments 1-93s, wherein the GLP-1 peptide has a minimum of 8 amino acid changes, when compared with GLP-1(7-37) (SEQ ID NO: 1).
93u. The derivative of any of embodiments 1-93t, wherein the GLP-1 peptide has a minimum of 9 amino acid changes, when compared with GLP-1(7-37) (SEQ ID NO: 1).
93v. The derivative of any of embodiments 1-93u, wherein the GLP-1 peptide has a minimum of 10 amino acid changes, when compared with GLP-1(7-37) (SEQ ID NO: 1).
93w. The derivative of any of embodiments 1-93v, wherein the GLP-1 peptide has 4 amino acid changes, when compared with GLP-1(7-37) (SEQ ID NO: 1).
93x. The derivative of any of embodiments 1-93w, wherein the GLP-1 peptide has 5 amino acid changes, when compared with GLP-1(7-37) (SEQ ID NO: 1).
93y. The derivative of any of embodiments 1-93x, wherein the GLP-1 peptide has 6 amino acid changes, when compared with GLP-1(7-37) (SEQ ID NO: 1).
93z. The derivative of any of embodiments 1-93y, wherein the GLP-1 peptide has 7 amino acid changes, when compared with GLP-1(7-37) (SEQ ID NO: 1).
93æ. The derivative of any of embodiments 1-93z, wherein the GLP-1 peptide has 8 amino acid changes, when compared with GLP-1(7-37) (SEQ ID NO: 1).
93ø. The derivative of any of embodiments 1-93æ, wherein the GLP-1 peptide has 9 amino acid changes, when compared with GLP-1(7-37) (SEQ ID NO: 1).
93å. The derivative of any of embodiments 1-93ø, wherein the GLP-1 peptide has 10 amino acid changes, when compared with GLP-1(7-37) (SEQ ID NO: 1).
94. The derivative of any of embodiments 1-93å, wherein the GLP-1 peptide incorporates only one Lys.
95. The derivative of any of embodiments 1-94, wherein the GLP-1 peptide is selected from the following analogues of GLP-1 (7-37) (SEQ ID NO: 1): i) (8Aib, 22E, 26R, 27K, 34R), ii) (8Aib, 22E, 26R, 34R, 37K), iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vi) (8Aib, 22E, 26R, 34R, 38K), vii) (8Aib, 22E, 26R, 34R, 38S, 39K), viii) (8Aib, 22E, 26R, 34R, 38S, 39S, 40G, 41A, 42P, 43K), and ix) (8Aib, 26R, 34R, 38K).
96. The derivative of any of embodiments 1-95, in the form of a sodium or potassium salt thereof.

96. The derivative of any of embodiments 1-95 which is a GLP-1 receptor agonist.
97. The derivative of embodiment 96, which is a full GLP-1 receptor agonist.
98. The derivative of any of embodiments 1-97, which is biologically active in vitro.
99. The derivative of any of embodiments 1-98, which is potent in vitro.
100. The derivative of any of embodiments 1-99, which is capable of activating the human GLP-1 receptor.
101. The derivative of any of embodiments 1-100 which is capable of activating the human GLP-1 receptor in an assay with whole cells expressing the human GLP-1 receptor, wherein the assay is performed in the absence of HSA (0% HSA), and/or in the presence of HSA (1% HSA).
102. The derivative of embodiment 101, where the response of the human GLP-1 receptor is measured in a reporter gene assay, such as the assay of Example 35.
103. The derivative of any of embodiments 98-102, wherein the biological activity, or potency, in vitro is determined essentially as described in Example 35.
104. The derivative of any of embodiments 1-103, which has an in vitro potency corresponding to an $EC_{50}$ of 300 pM or below.
105. The derivative of any of embodiments 1-104, which has an in vitro potency corresponding to an $EC_{50}$ of 200 pM or below.
106. The derivative of any of embodiments 1-105, which has an in vitro potency corresponding to an $EC_{50}$ of 100 pM or below.
107. The derivative of any of embodiments 1-106, which has an in vitro potency corresponding to an $EC_{50}$ of 75 pM or below.
108. The derivative of any of embodiments 1-107, which has an in vitro potency corresponding to an $EC_{50}$ of 50 pM or below.
109. The derivative of any of embodiments 1-108, which has an in vitro potency corresponding to an $EC_{50}$ of 25 pM or below.
110. The derivative of any of embodiments 104-109, wherein the $EC_{50}$ is determined essentially as described in Example 35.
111. The derivative of any of embodiments 1-110, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.
112. The derivative of any of embodiments 1-111, which has an in vitro potency corresponding to an $EC_{50}$ of less than 20 times the $EC_{50}$ of semaglutide, wherein the $EC_{50}$ of semaglutide is determined in the same way as the $EC_{50}$ of the derivative.
113. The derivative of any of embodiments 1-112, which has an in vitro potency corresponding to an $EC_{50}$ of less than 10 times the $EC_{50}$ of semaglutide, wherein the $EC_{50}$ of semaglutide is determined in the same way as the $EC_{50}$ of the derivative.
114. The derivative of any of embodiments 1-113, which has an in vitro potency corresponding to an $EC_{50}$ of less than 7.5 times the $EC_{50}$ of semaglutide, wherein the $EC_{50}$ of semaglutide is determined in the same way as the $EC_{50}$ of the derivative.
115. The derivative of any of embodiments 1-114, which has an in vitro potency corresponding to an $EC_{50}$ of less than 5 times the $EC_{50}$ of semaglutide, wherein the $EC_{50}$ of semaglutide is determined in the same way as the $EC_{50}$ of the derivative.
116. The derivative of any of embodiments 1-115, which has an in vitro potency corresponding to an $EC_{50}$ of less than 2.5 times the $EC_{50}$ of semaglutide, wherein the $EC_{50}$ of semaglutide is determined in the same way as the $EC_{50}$ of the derivative.
117. The derivative of any of embodiments 111-116, wherein the $EC_{50}$ is determined essentially as described in Example 35.
118. The derivative of any of embodiments 1-117, which is capable of binding to the GLP-1 receptor.
119. The derivative of any of embodiments 1-118, which is capable of binding to the GLP-1 receptor at a low concentration of HSA (max. 0.001% final assay concentration).
120. The derivative of any of embodiments 1-119, which is capable of binding to the GLP-1 receptor at a high concentration of HSA (2.0% final assay concentration).
121. The derivative of any of embodiments 118-120, wherein the binding to the human GLP-1 receptor is measured in a competitive binding assay, such as the assay of Example 36.
122. The derivative of any of embodiments 118-121, wherein the binding to the human GLP-1 receptor in vitro is determined essentially as described in Example 362.
123. The derivative of any of embodiments 1-122, which at a very low concentration of HSA is capable of binding to the human GLP-1 receptor with an $IC_{50}$ of 3.0 nM or below.
124. The derivative of any of embodiments 1-123, which at a very low concentration of HSA is capable of binding to the human GLP-1 receptor with an $IC_{50}$ of 2.0 nM or below.
125. The derivative of any of embodiments 1-124, which at a very low concentration of HSA is capable of binding to the human GLP-1 receptor with an $IC_{50}$ of 1.0 nM or below.
126. The derivative of any of embodiments 1-125, which at a very low concentration of HSA is capable of binding to the human GLP-1 receptor with an $IC_{50}$ of 0.5 nM or below.
127. The derivative of any of embodiments 123-126, wherein the $IC_{50}$ is determined essentially as described in Example 36, in a reaction with max. 0.001% HSA (final assay concentration).
128. The derivative of any of embodiments 1-127, which at a very low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.
129. The derivative of any of embodiments 1-128, which at a very low concentration of HSA is capable of binding to the human GLP-1 receptor with an $IC_{50}$ of less than 1.5 times the $IC_{50}$ of semaglutide, wherein the $IC_{50}$ of semaglutide is determined in the same way as the $IC_{50}$ of the derivative.
130. The derivative of any of embodiments 1-129, which at a very low concentration of HSA is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.
131. The derivative of any of embodiments 1-130, which at a very low concentration of HSA is capable of binding to the human GLP-1 receptor with an $IC_{50}$ of less than 0.6 times the $IC_{50}$ of semaglutide, wherein the $IC_{50}$ of semaglutide is determined in the same way as the $IC_{50}$ of the derivative.

132. The derivative of any of embodiments 123-131, wherein the $IC_{50}$ is determined essentially as described in Example 36, in a reaction with max. 0.001% HSA (final assay concentration).

133. The derivative of any of embodiments 1-132, which at 2.0% HSA (final assay concentration) is capable of binding to the human GLP-1 receptor with an $IC_{50}$ of 300 nM or below.

134. The derivative of any of embodiments 1-133, which at 2.0% HSA (final assay concentration) is capable of binding to the human GLP-1 receptor with an $IC_{50}$ of 125 nM or below.

135. The derivative of any of embodiments 1-134, which at 2.0% HSA (final assay concentration) is capable of binding to the human GLP-1 receptor with an $IC_{50}$ of 75 nM or below.

136. The derivative of any of embodiments 1-135, which at 2.0% HSA (final assay concentration) is capable of binding to the human GLP-1 receptor with an $IC_{50}$ of 50 nM or below.

137. The derivative of any of embodiments 133-136, wherein the $IC_{50}$ is determined essentially as described in Example 36, in a reaction with 2.0% HSA (final assay concentration).

138. The derivative of any of embodiments 1-137, which at 2.0% HSA (final assay concentration) is capable of binding to the human GLP-1 receptor with an $IC_{50}$ of less than 1 time the $IC_{50}$ of semaglutide, wherein the $IC_{50}$ of semaglutide is determined in the same way as the $IC_{50}$ of the derivative.

139. The derivative of any of embodiments 1-138, which at 2.0% HSA (final assay concentration) is capable of binding to the human GLP-1 receptor with an $IC_{50}$ of less than 0.5 times the $IC_{50}$ of semaglutide, wherein the $IC_{50}$ of semaglutide is determined in the same way as the $IC_{50}$ of the derivative.

140. The derivative of any of embodiments 1-139, which at 2.0% HSA (final assay concentration) is capable of binding to the human GLP-1 receptor with an $IC_{50}$ of less than 0.25 times the $IC_{50}$ of semaglutide, wherein the $IC_{50}$ of semaglutide is determined in the same way as the $IC_{50}$ of the derivative.

141. The derivative of any of embodiments 1-140, which at 2.0% HSA (final assay concentration) is capable of binding to the human GLP-1 receptor with an $IC_{50}$ of less than 0.17 times the $IC_{50}$ of semaglutide, wherein the $IC_{50}$ of semaglutide is determined in the same way as the $IC_{50}$ of the derivative.

142. The derivative of any of embodiments 138-141, wherein the $IC_{50}$ is determined essentially as described in Example 36, in a reaction with 2.0% HSA (final assay concentration).

143. The derivative of any of embodiments 1-142, which has improved pharmacokinetic properties.

144. The derivative of any of embodiments 1-143, which has an increased half-life and/or a decreased clearance.

145. The derivative of any of embodiments 1-144, which is suitable for once-monthly administration.

146. The derivative of embodiment 145, for s.c. administration.

147. The derivative of any of embodiments 143-146, wherein the derivative is tested in vivo in pharmacokinetic (PK) studies.

148. The derivative of embodiment 147, wherein the derivative is tested in any suitable animal model, such as mouse, rat, monkey, dog, or pig.

149. The derivative of any of embodiments 143-148, which is compared with semaglutide.

150. The derivative of any of embodiments 1-149, which has an improved terminal half-life (T½) in vivo in minipigs after i.v. administration as compared to semaglutide.

151. The derivative of any of embodiments 143-150, wherein the terminal half-life is determined in vivo in minipigs after i.v. administration using any suitable study protocol, such as the one described in Example 37.

152. The derivative of any of embodiments 143-151, wherein the terminal half-life is determined in vivo in minipigs after i.v. administration, essentially as described in Example 37.

153. The derivative of any of embodiments 1-152, which has a terminal half-life (T½) in vivo in minipigs after i.v. administration of at least 100 hours.

154. The derivative of any of embodiments 1-153, which has a terminal half-life (T½) in vivo in minipigs after i.v. administration of at least 125 hours.

155. The derivative of any of embodiments 1-154, which has a terminal half-life (T½) in vivo in minipigs after i.v. administration of at least 150 hours.

156. The derivative of any of embodiments 1-155, which has a terminal half-life (T½) in vivo in minipigs after i.v. administration of at least 175 hours.

157. The derivative of any of embodiments 1-156, which has a terminal half-life (T½) in vivo in minipigs after i.v. administration of at least 2.1 times the terminal half-life of semaglutide, determined in the same way.

158. The derivative of any of embodiments 1-157, which has a terminal half-life (T½) in vivo in minipigs after i.v. administration of at least 2.5 times the terminal half-life of semaglutide, determined in the same way.

159. The derivative of any of embodiments 1-158, which has a terminal half-life (T½) in vivo in minipigs after i.v. administration of at least 2.8 times the terminal half-life of semaglutide, determined in the same way.

160. The derivative of any of embodiments 1-159, which has a terminal half-life (T½) in vivo in minipigs after i.v. administration of at least 3.3 times the terminal half-life of semaglutide, determined in the same way.

161. The derivative of any of embodiments 1-160, which is potent in vivo.

162. The derivative of any of embodiments 1-161, which is potent in vivo when determined in any suitable animal model, such as mouse or pig.

163. The derivative of embodiment 162, wherein the animal model is db/db mouse.

164. The derivative of any of embodiments 161-163, wherein the blood glucose lowering effect is determined.

165. The derivative of any of embodiments 161-164, wherein the body weight lowering effect is determined.

166. The derivative of any of embodiments 1-165, wherein blood glucose lowering effect and/or body weight lowering effect is determined in vivo in db/db mouse using any suitable study protocol and methodology, e.g. as described in Example 38.

167. The derivative of any of embodiments 1-166, wherein the blood glucose lowering effect and/or the body weight lowering effect is determined in vivo in db/db mouse, essentially as described in Example 38.

168. The derivative of any of embodiments 1-167, which has the effect in vivo of decreasing blood glucose after 48 hours, determined in a single-dose study in a db/db mouse model.
169. The derivative of embodiment 168, wherein the blood glucose is decreased by at least 15%, as compared to the blood glucose level before administration of the derivative.
170. The derivative of any of embodiments 168-169, wherein the blood glucose is decreased by at least 30%, as compared to the blood glucose level before administration of the derivative.
171. The derivative of any of embodiments 168-170, wherein the blood glucose is decreased by at least 37%, as compared to the blood glucose level before administration of the derivative.
172. The derivative of any of embodiments 168-171, wherein the blood glucose is decreased by at least 47%, as compared to the blood glucose level before administration of the derivative.
173. The derivative of any of embodiments 1-172, which has the effect in vivo of decreasing blood glucose after 72 hours, determined in a single-dose study in a db/db mouse model.
174. The derivative of any of embodiments 1-173, which has the effect in vivo of decreasing blood glucose after 96 hours, determined in a single-dose study in a db/db mouse model.
175. The derivative of embodiment 174, wherein the blood glucose is decreased by at least 5%, as compared to the blood glucose level before administration of the derivative.
176. The derivative of any of embodiments 174-175, wherein the blood glucose is decreased by at least 10%, as compared to the blood glucose level before administration of the derivative.
177. The derivative of any of embodiments 174-176, wherein the blood glucose is decreased by at least 15%, as compared to the blood glucose level before administration of the derivative.
178. The derivative of any of embodiments 174-177, wherein the blood glucose is decreased by at least 20%, as compared to the blood glucose level before administration of the derivative.
179. The derivative of any of embodiments 174-178, wherein the blood glucose is decreased by at least 25%, as compared to the blood glucose level before administration of the derivative.
180. The derivative of any of embodiments 1-179, which has the effect in vivo of decreasing body weight after 48 hours, determined in a single-dose study in a db/db mouse model.
181. The derivative of embodiment 180, wherein the body weight is decreased by at least 3%, as compared to the body weight before administration of the derivative.
182. The derivative of any of embodiments 180-181, wherein the body weight is decreased by at least 4%, as compared to the body weight before administration of the derivative.
183. The derivative of any of embodiments 180-182, wherein the body weight is decreased by at least 5%, as compared to the body weight before administration of the derivative.
184. The derivative of any of embodiments 180-183, wherein the body weight is decreased by at least 6%, as compared to the body weight before administration of the derivative.
185. The derivative of any of embodiments 1-184, which has the effect in vivo of decreasing body weight after 72 hours, determined in a single-dose study in a db/db mouse model.
186. The derivative of any of embodiments 1-185 which has the effect in vivo of decreasing body weight after 96 hours, determined in a single-dose study in a db/db mouse model.
187. The derivative of embodiment 186, wherein the body weight is decreased by at least 2%, as compared to the body weight before administration of the derivative.
188. The derivative of any of embodiments 186-187, wherein the body weight is decreased by at least 3%, as compared to the body weight before administration of the derivative.
189. The derivative of any of embodiments 186-188, wherein the body weight is decreased by at least 4%, as compared to the body weight before administration of the derivative.
190. The derivative of any of embodiments 186-189, wherein the body weight is decreased by at least 5%, as compared to the body weight before administration of the derivative.
191. The derivative of any of embodiments 186-190, wherein the body weight is decreased by at least 6%, as compared to the body weight before administration of the derivative.
192. The derivative of embodiment 162, wherein the animal model is pig.
193. The derivative of embodiment 192, wherein the animal model is LYD pig.
194. The derivative of any of embodiments 192-193, wherein the reduction in food intake is determined in an in vivo pharmacodynamic (PD) study.
195. The derivative of any of embodiments 192-194, wherein the reduction in food intake is determined in vivo in pig using any suitable study protocol and methodology, e.g. as described in Example 39.
196. The derivative of any of embodiments 192-195, wherein the reduction in food intake is determined in vivo in pig using any suitable study protocol and methodology, essentially as described in Example 39.
197. The derivative of any of embodiments 1-196, which has the effect in vivo of reducing food intake during a first period of 24 hours (0-24 hours) after administration of a single dose of the derivative, wherein food intake is determined in a single-dose study in a LYD pig model.
198. The derivative of any of embodiments 1-197, which has the effect in vivo of reducing food intake during a second period of 24 hours (24-48 hours) after administration of a single dose of the derivative, wherein food intake is determined in a single-dose study in a LYD pig model.
199. The derivative of any of embodiments 1-198, which has the effect in vivo of reducing food intake during a third period of 24 hours (48-72 hours) after administration of a single dose of the derivative, wherein food intake is determined in a single-dose study in a LYD pig model.
200. The derivative of any of embodiments 1-199, which has the effect in vivo of reducing food intake during a fourth period of 24 hours (72-96 hours) after administration of a single dose of the derivative, wherein food intake is determined in a single-dose study in a LYD pig model.
201. A GLP-1 derivative selected from the following: Chem. 21, Chem. 22, Chem. 23, Chem. 24, Chem. 25, Chem. 26, Chem. 27, Chem. 28, Chem. 29, Chem. 30, Chem. 31, Chem. 32, Chem. 33, Chem. 34, Chem. 35, Chem. 36, Chem. 37, Chem. 38, Chem. 39, and Chem. 40; or a pharmaceutically acceptable salt, amide, or ester thereof.

202. A GLP-1 derivative selected from the chemical structures shown in any of Examples 1-34, preferably 1-20; or a pharmaceutically acceptable salt, amide, or ester thereof.

203. A GLP-1 derivative selected from the GLP-1 derivative names shown in any of Examples 1-34, preferably 1-20; or a pharmaceutically acceptable salt, amide, or ester thereof.

204. The derivative of any of embodiments 201-203, which is a derivative according to any of embodiments 1-200.

205. An intermediate product in the form of a GLP-1 analogue, which comprises the following amino acid changes when compared to GLP-1 (7-37) (SEQ ID NO: 1): iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vii) (8Aib, 22E, 26R, 34R, 38S, 39K), or viii) (8Aib, 22E, 26R, 34R, 38S, 39S, 40G, 41A, 42P, 43K).

205a. An intermediate product in the form of a GLP-1 analogue, which comprises the following amino acid changes when compared to GLP-1 (7-37) (SEQ ID NO: 1): 40K, 41K, 42K, or 43K.

205b. The intermediate product of embodiment 205a, which is a GLP-1 peptide of formula I as defined in embodiment 1.

205c. The intermediate product of any of embodiments 205a-205b, which is a GLP-1 peptide as defined in any of embodiments 33-40, 205d. The intermediate product of any of embodiments 205a-205c, which is a GLP-1 peptide as defined in any of embodiments 47-95, 206. An intermediate product in the form of a GLP-1 analogue, selected from the following analogues of GLP-1 (7-37) (SEQ ID NO: 1): i) (8Aib, 22E, 26R, 27K, 34R), iii) (8Aib, 22E, 26R, 34R, 38G, 39G, 40G, 41S, 42K), iv) (8Aib, 22E, 26R, 34R, 38G, 39G, 40S, 41K), v) (8Aib, 22E, 26R, 34R, 38G, 39S, 40K), vii) (8Aib, 22E, 26R, 34R, 38S, 39K), and viii) (8Aib, 22E, 26R, 34R, 38S, 39S, 40G, 41A, 42P, 43K).

207. A pharmaceutical composition comprising a derivative according to any of embodiments 1-204, or an analogue according to any of embodiments 205-206 including 205a-205d, and a pharmaceutically acceptable excipient.

208. A derivative according to any of embodiments 1-204, or an analogue according to any of embodiments 205-206 including 205a-205d, for use as a medicament.

209. A derivative according to any of embodiments 1-204, or an analogue according to any of embodiments 205-206 including 205a-205d, for use in
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;
(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;
(iii) improving β-cell function, such as decreasing β-cell apoptosis, increasing β-cell function and/or β-cell mass, and/or for restoring glucose sensitivity to β-cells;
(iv) prevention and/or treatment of cognitive disorders and/or neurodegenerative disorders, such as Alzheimer's disease, Parkinson's disease, and/or multiple sclerosis;
(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;
(vi) prevention and/or treatment of diabetic complications, such as angiopathy; neuropathy, including peripheral neuropathy; nephropathy; and/or retinopathy;
(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;
(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;
(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;
(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;
(xi) prevention and/or treatment of polycystic ovary syndrome (PCOS);
(xii) prevention and/or treatment of cerebral disease, such as cerebral ischemia, cerebral haemorrhage, and/or traumatic brain injury;
(xiii) prevention and/or treatment of sleep apnoea; and/or
(xiv) prevention and/or treatment of abuse, such as alcohol abuse and/or drug abuse.

210. Use of a derivative according to any of embodiments 1-204, or an analogue according to any of embodiments 205-206 including 205a-205d, in the manufacture of a medicament for
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

211. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative according to any of embodiments 1-204, or an analogue according to any of embodiments 205-206 including 205a-205d, is administered.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

List of Abbreviations

Aib: α-aminoisobutyric acid (2-Aminoisobutyric acid)
AcOH: acetic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DesH: des-amino histidine (imidazopropionic acid or 3-(Imidazol-5-yl)propanoic acid), Imp
DIC: diisopropylcarbodiimide
DIPEA: diisopropylethylamine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (O-(7-azabenzotriazol-1-yl)-1,1,3,3-tetramethyluronium hexafluorophosphate)
HBTU: (2-(1H-benzotriazol-1-yl)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid or (3-(Imidazol-5-yl)propanoic acid) (also referred to as des-amino histidine, DesH)
Inp: isonipecotic acid
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OBz: benzoyl ester
OEG: 8-amino-3,6-dioxaoctanoic acid
OPfp: pentafluorophenoxy
OPnp: para-nitrophenoxy
OSu: 0-succinimidyl esters (hydroxysuccinimide esters)
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Penicillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid
UPLC: Ultra Performance Liquid Chromatography Materials and Methods Eicosanedioic acid mono-tert-butyl ester
Docosanedioic acid mono-tert-butyl ester
Fmoc-8-amino-3,6-dioxaoctanoic acid
Fmoc-tranexamic acid
Fmoc-isonipecotic acid
Fmoc-Lys(Fmoc)-OH
Fmoc-Glu-OtBu
Fmoc-21-amino-4,7,10,13,16,19-hexaoxaheneicosanoic acid
Fmoc-15-amino-4,7,10,13-tetraoxapentadecanoic acid
1-(9-Fluorenylmethyloxycarbonyl)amino-3,6,9,12,15,18,21,24,27,30,33,36-dodecaoxanonatriacontan-39-oic acid
alpha-(9-Fluorenylmethyloxycarbonyl)amino-omega-carboxy hexadeca(ethylene glycol)

Chemical Methods

This section is divided in two: Section A relating to general methods (of preparation (A1); and of detection and characterisation (A2)), and section B, in which the preparation and characterisation of a number of specific example compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular side chain or albumin binding moiety attachment using SPPS the following suitably protected building blocks such as but not limited to Fmoc-8-amino-3,6-dioxaoctanoic acid, Fmoc-tranexamic acid, Fmoc-Glu-OtBu, and eicosanedioic acid mono-tert-butyl ester were used. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesizer from Protein Technologies (Tucson, Ariz. 85714 U.S.A.) at 250-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 5% piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

2. Synthesis of Albumin Binder (Side Chain)

Eicosanedioic acid mono-tert-butyl ester can be prepared as known in the art. For a method please refer to WO 2010102886 A1.

Docosanedioic acid mono-tert-butyl ester can be prepared as exemplified below:

1 M solution of borane-tetrahydrofuran complex in tetrahydrofuran (94.1 mL, 94.1 mmol) was added dropwise to a solution of icosanedioic acid mono-tert-butyl ester (25.0 g, 62.7 mmol) in dry tetrahydrofuran (140 mL) at 0 C under argon. The resulting solution was stirred at 0 C for 2 hrs, then the cooling bath was removed and the mixture stirred at room temperature overnight. Saturated aqueous solution of sodium bicarbonate (300 mL) and water (100 mL) were added and the resulting mixture was extracted with dichloromethane (250 mL, 2×100 mL). Combined organic extracts were dried over anhydrous sodium sulfate and evaporated to dryness. The residue was purified by column chromatography on silicagel (eluent: dichloromethane/methanol 99:1). Fractions with pure product were evaporated, residue was chromatographed again (eluent: dichloromethane/methanol 99:1). Products were combined and dried in vacuo yielding 20-hydroxy-icosanoic acid tert-butyl ester as white solid.

Yield: 16.50 g (68%).

$^1$H NMR spectrum (300 MHz, CDCl$_3$, delta$_H$): 3.64 (t, J=6.6 Hz, 2 H), 2.20 (t, J=7.5 Hz, 2 H); 1.65-1.51 (m, 4 H); 1.45 (s, 9 H); 1.36-1.21 (m, 30 H).

The above prepared alcohol (16.5 g, 42.9 mmol) was dissolved in dry dichloromethane (90 mL). Triethylamine (9.00 mL, 64.4 mmol) was added, reaction mixture was cooled to 0 C and mesyl chloride (4.00 mL, 51.5 mmol) was added dropwise. After 1 hr the reaction mixture was allowed to warm to room temperature and has been stirred overnight. Water (1.5 mL) was added and the mixture was stirred 30 minutes. Solvents were evaporated, ethyl acetate was added (200 mL) and the mixture was extracted with 1 M hydrochloric acid (2×100 mL), 5% solution of sodium carbonate (2×100 mL) and water (100 mL). After drying with anhydrous sodium sulfate, filtration and evaporation of solvents 20-methanesulfonyloxy-icosanoic acid tert-butyl ester was obtained as white solid.

Yield: 19.80 g (100%).

$^1$H NMR spectrum (300 MHz, CDCl$_3$, delta$_H$): 4.22 (t, J=6.6 Hz, 2 H); 3.01 (s, 3 H); 2.20 (t, J=7.5 Hz, 2 H); 1.81-1.68 (m, 2 H); 1.63-1.51 (m, 2 H); 1.44 (s, 9 H); 1.34-1.22 (m, 30 H).

The above prepared mesylate (17.8 g, 38.5 mmol) was dissolved in acetone (250 mL) and lithium bromide (6.69 g, 77.0 mmol) was added and the reaction mixture was refluxed overnight. After cooling down solvent was evaporated, ethyl acetate (300 mL) was added and the mixture was extracted with 5% solution of sodium bicarbonate (3×170 mL). Combined organic extracts were dried over anhydrous sodium sulfate and evaporated. Product was dried in vacuo to yield 20-bromo-icosanoic acid tert-butyl ester as white solid.

Yield: 17.10 g (99%).

$^1$H NMR spectrum (300 MHz, CDCl$_3$, delta$_H$): 3.41 (t, J=6.9 Hz, 2 H); 2.20 (t, J=7.4 Hz, 2 H); 1.90-1.77 (m, 2 H); 1.64-1.50 (m, 2 H); 1.43 (s, 9 H); 1.34-1.13 (m, 30 H).

Sodium hydride (60% dispersion in mineral oil, 3.96 g, 99.0 mmol) was dissolved in N,N-dimethylformamide (100 mL) under nitrogen. Dimethyl malonate (22.6 mL, 198 mmol) was added and the reaction mixture was heated briefly at 100 C, then cooled to room temperature and the solution of above prepared 20-bromo-icosanoic acid tert-butyl ester (14.8 g, 33.0 mmol) in N,N-dimethylformamide (150 mL) was added. The reaction mixture was heated at 100 C for 4 hrs. After cooling to room temperature, ethyl acetate (150 mL) was added and the organic solution was washed with saturated aqueous ammonium chloride (3×100 mL) and brine (100 mL), dried over anhydrous sodium sulfate and evaporated to dryness. Residue was purified by column chromatography on silicagel (eluent: hexane/ethyl acetate 96:4 to 93:7) giving 2-methoxycarbonyl-docosanedioic acid 22-tert-butyl ester 1-methyl ester as white solid.

Yield: 16.10 g (97%).

$^1$H NMR spectrum (300 MHz, CDCl$_3$, delta$_H$): 3.74 (s, 6 H); 3.36 (t, J=7.5 Hz, 1 H); 2.20 (t, J=7.5 Hz, 2 H); 1.95-1.84 (m, 2 H); 1.64-1.51 (m, 2 H); 1.44 (s, 9 H); 1.34-1.21 (m, 32 H).

The above prepared 2-methoxycarbonyl-docosanedioic acid 22-tert-butyl ester 1-methyl ester (16.1 g, 32.3 mmol) was dissolved in tetrahydrofuran (85 mL) and solution of lithium hydroxide monohydrate (4.07 g, 96.9 mmol) in water (75 mL) was added. The reaction mixture was stirred at room temperature overnight, then it was acidified with 1 M hydrochloric acid and extracted with ethyl acetate (4×150 mL). Organic extracts were combined, dried over anhydrous sodium sulfate and evaporated. Product was dried in vacuo to yield 2-carboxy-docosanedioic acid 22-tert-butyl ester as white solid.

Yield: 14.50 g (95%).

$^1$H NMR spectrum (300 MHz, CDCl$_3$, delta$_H$): 3.44 (t, J=7.4 Hz, 1 H); 2.22 (t, J=7.5 Hz, 2 H); 2.00-1.89 (m, 2 H); 1.63-1.52 (m, 2 H); 1.45 (s, 9 H); 1.37-1.20 (m, 32 H).

2-Carboxy-docosanedioic acid 22-tert-butyl ester (14.5 g, 30.8 mmol) was dissolved in toluene (170 mL) and refluxed at 110 C for 48 hrs. Solvent was evaporated, residue was purified by column chromatography on silicagel (eluent: dichloromethane/methanol 97:3) giving the titled compound as white solid.

Yield: 5.25 g (40%).

Total yield: 5.25 g (25%)

1H NMR spectrum (300 MHz, CDCl$_3$, delta$_H$): 2.35 (t, J=7.5 Hz, 2 H); 2.21 (t, J=7.5 Hz, 2 H); 1.68-1.53 (m, 4 H); 1.45 (s, 9 H); 1.35-1.22 (m, 32 H).

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% hydrazine in NMP (2×20 ml, each 10 min) followed by NMP washings (4×20 ml). Mtt- or Mmt-deprotection was performed with 2% TFA and 2-3% TIS in DCM (5×20 ml, each 10 min) followed by DCM (2×20 ml), 10% MeOH and 5% DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The protracting moiety and/or linker can be attached to the peptide either by acylation of the resin bound peptide or by acylation in solution of the unprotected peptide. In case of attachment of the protracting moiety and/or linker to the protected peptidyl resin the attachment can be modular using SPPS and suitably protected building blocks.

Method: SC_P

The N-ε-lysine protection group was removed as described above and the chemical modification of the lysine was performed by one or more automated steps on the Prelude peptide synthesiser using suitably protected building blocks as described above. Double couplings were performed as described in SPPS_P with 3 hours per coupling.

Method: SC_L

The N-εlysine protection group was removed as described above and the chemical modification of the lysine was performed by one or more automated steps on the Liberty peptide synthesiser using suitably protected building blocks as described above. Double couplings were performed as described in SPPS_L.

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a C18, 5 μm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using the methods known in the art. As an example approx. 2 g peptide was dissolved in 250 ml acetonitrile/water (50/50) and loaded onto a Waters X-Bridge C8, 5 μM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

Method: CP_M2

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% acetic acid) and purified by standard RP-HPLC on a Kinetex C18, 5 μm column, eluting with a binary mixture of 0.09M diammoniumhydrogenphosphate in water/acetonitrile (90:10, pH 3.0) and acetonitrile/2-propanol/water (60:20:20). The peptide was then further purified by standard RP-HPLC on a C18, 5 μm column, using acetonitrile/water/TFA. The fractions were analysed by a combination of UPLC, MALDI and LCMS methods, and the appropriate fractions were pooled and lyophilised.

If desired the peptide counter ion can be exchanged to sodium using the methods known in the art. As an example approx. 2 g peptide was dissolved in 250 ml acetonitrile/water (50/50) and loaded onto a Waters X-Bridge C8, 5 μM, 50×250 mm column on a preparative RP-HPLC system. Following loading, the column was washed with water for 8 min at a flow rate of 60 ml/min and 0.01 N NaOH pH 11 at a flow rate of 60 ml/min for 2×8 min. The sodium salt of the peptide was eluted using an isocratic flow of water at 60 ml/min for 10 min followed by a linear gradient of 5% to 85% acetonitrile over 30 min.

A2. General Methods for Detection and Characterisation

1. LC-MS methods
Method: LCMS01v1

LCMS01v1 was performed on a setup consisting of Waters Acquity UPLC system and LCT Premier XE mass spectrometer from Micromass. Eluents: A: 0.1% Formic acid in water; B: 0.1% Formic acid in acetonitrile. The analysis was performed at RT by injecting an appropriate volume of the sample (preferably 2-10 μl) onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES. Scan: 100-2000 amu (alternatively 500-2000 amu), step 0.1 amu.

2. UPLC Method
Method: UPLC02v01

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C. The UPLC system was connected to two eluent reservoirs containing: A: 99.95% H$_2$O, 0.05% TFA; B: 99.95% CH$_3$CN, 0.05% TFA. The following linear gradient was used: 95% A, 5% B to 95% A, 5% B over 16 minutes at a flow-rate of 0.40 ml/min.

3. MALDI-MS Method
Method: MALDI01v01

Molecular weights were determined using matrix-assisted laser desorption and ionisation time-of-flight mass spectroscopy, recorded on a Microflex or Autoflex (Bruker). A matrix of alpha-cyano-4-hydroxy cinnamic acid was used.

B. Synthesis of Compounds of the Invention

Example 1

[Aib8,Glu22,Arg26,Arg34]-GLP-1-(7-37)-peptidyl-Gly-Gly-Gly-Ser-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys Chem. 21

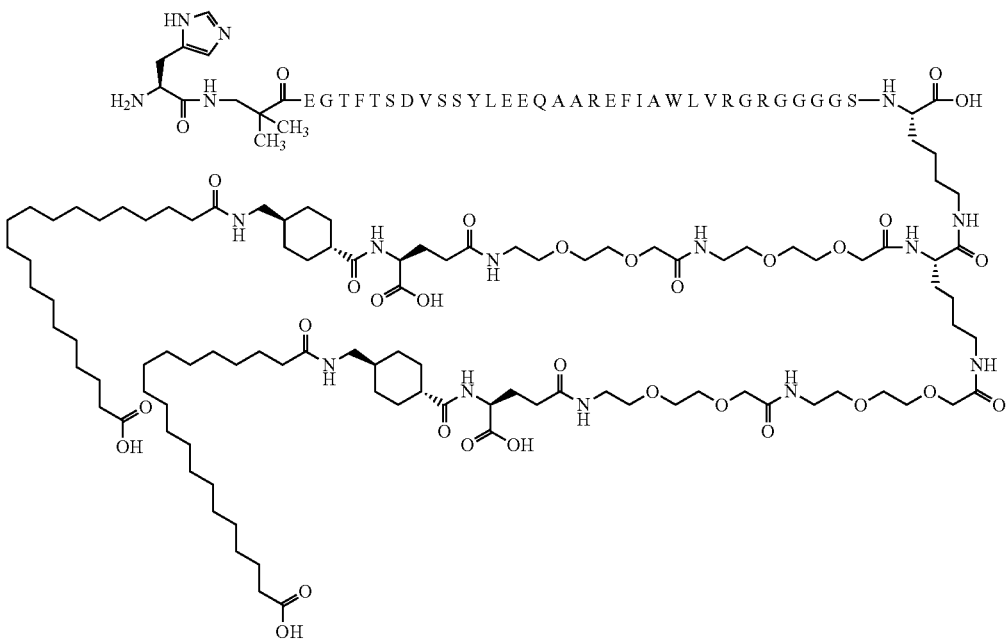

The peptide is SEQ ID NO: 2.
Synthesis method: SPPS_P; SC_P; CP_M1
UPLC02v01: Rt=11.8 min
LCMS01v01: Rt=2.7 min, m/3=1927; m/4=1445; m/5=1156

Example 2

[Aib8,Glu22,Arg26,Arg34]-GLP-1-(7-37)-peptidyl-Gly-Gly-Ser-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys

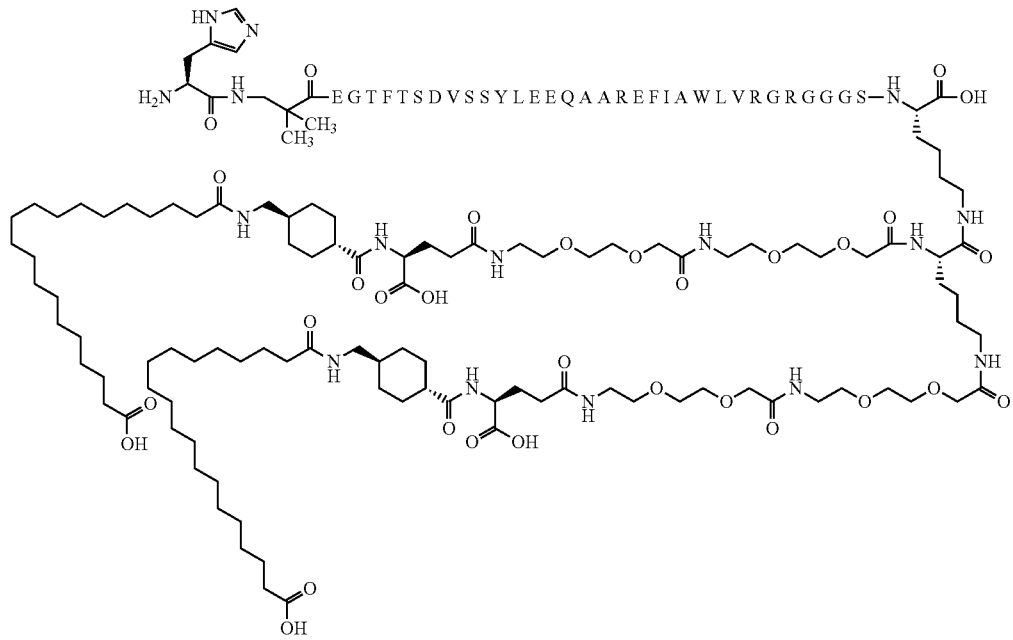

Chem. 22

The peptide is SEQ ID NO: 3.
Synthesis method: SPPS_P; SC_P; CP_M1
UPLC02v01: Rt=11.3 min
LCMS01v01: Rt=2.6 min, m/3=1908; m/4=1431; m/5=1145

Example 3
[Aib8,Glu22,Arg26,Arg34]-GLP-1-(7-37)-peptidyl-Gly-Ser-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys
Chem. 23:
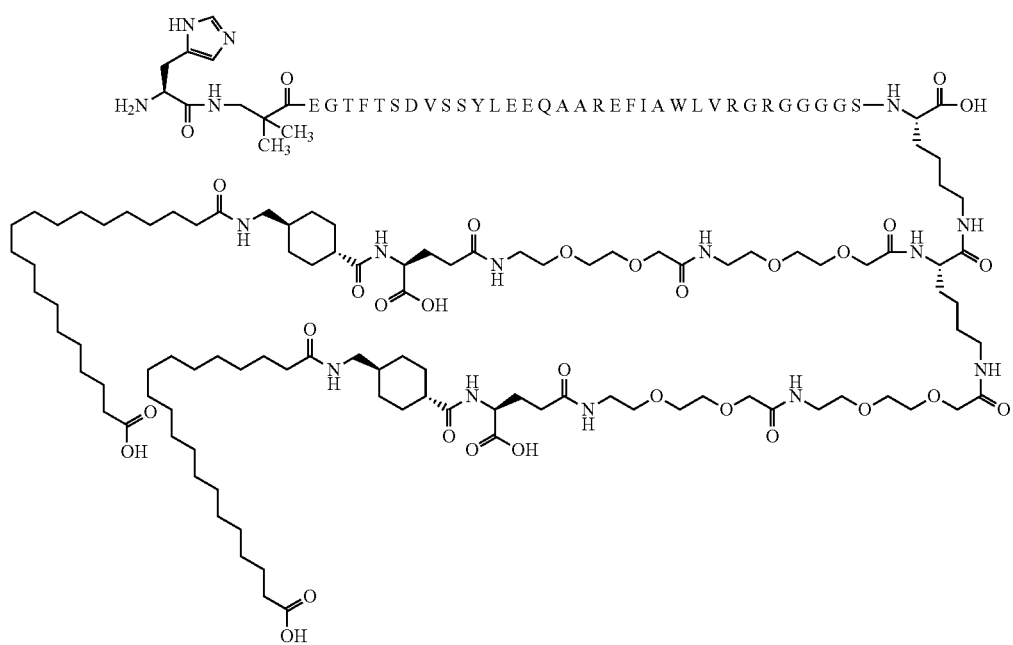
The peptide is SEQ ID NO: 4.
Synthesis method: SPPS_P; SC_P; CP_M1
UPLC02v01: Rt=11.3 min
LCMS01v01: Rt=2.6 min, m/3=1889; m/4=1417; m/5=1134

Example 4

[Aib8,Glu22,Arg26,Arg34]-GLP-1-(7-37)-peptidyl-Ser-N{Epsilon}[(2S)-2,6-bis[[2-[2-[2[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexoyl]Lys

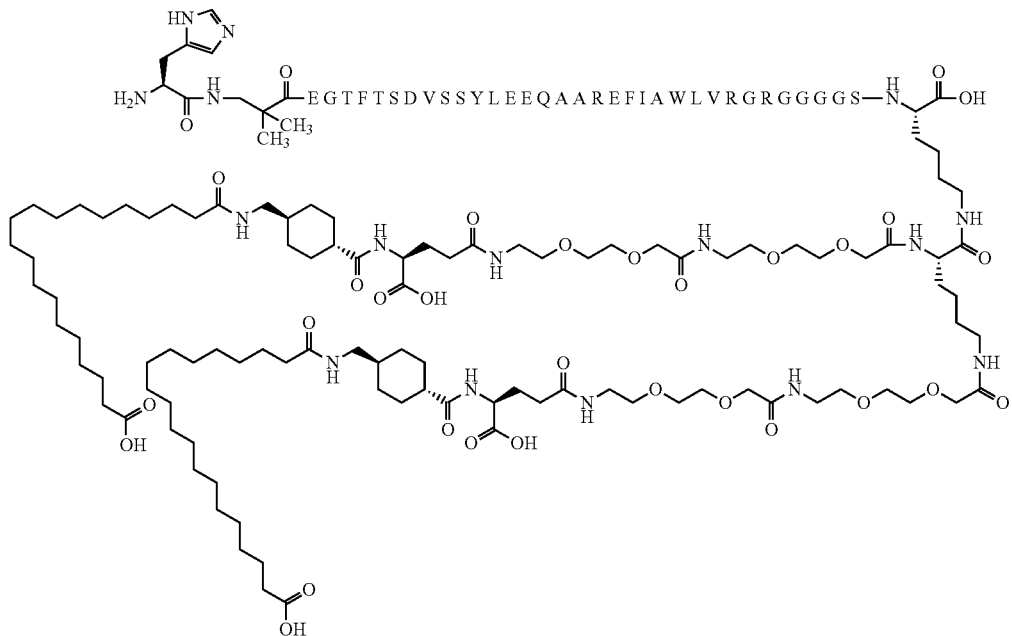

Chem. 24

The peptide is SEQ ID NO: 5.
Synthesis method: SPPS_P; SC_P; CP_M1
UPLC02v01: Rt=11.4 min
LCMS01v01: Rt=2.8 min, m/4=1403; m/5=1122

Example 5

N{Epsilon-37}-[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]-[Aib8,Glu22,Arg26,Arg34,Lys37]-GLP-1-(7-37)-peptide

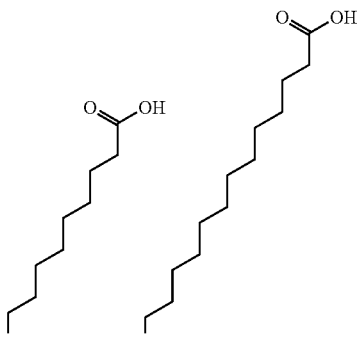

Chem. 25

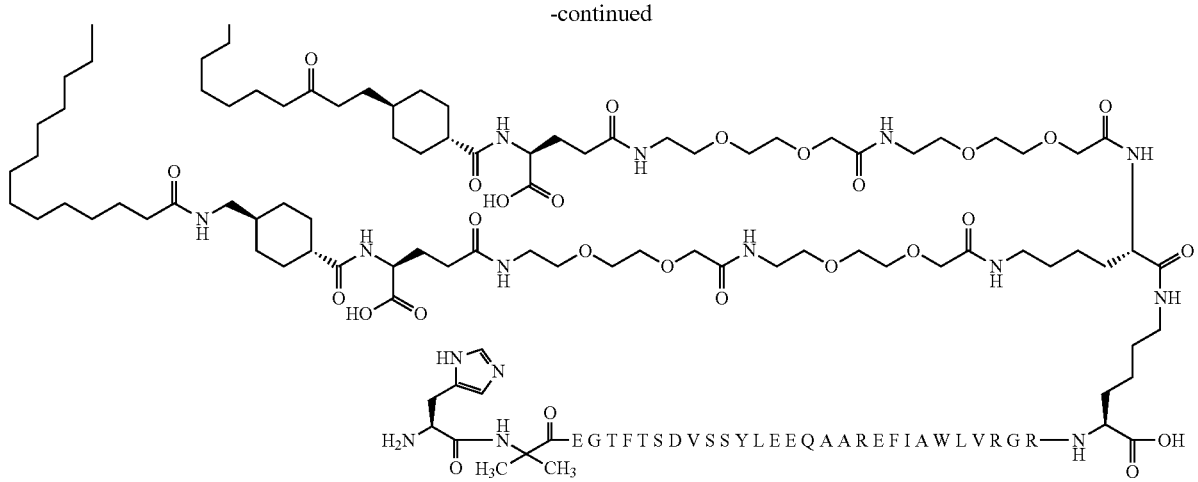
Synthesis method: SPPS_P; SC_L; CP_M1
UPLC02v01: Rt=11.4 min
LCMS01v01: Rt=2.5 min, m/3=1822; m/4=1367; m/5=1094
Example 6
N{Epsilon-37}-[(2S)-2,6-bis[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]hexanoyl]-[Aib8,Glu22,Arg26,Arg34,Lys37]-GLP-1-(7-37)-peptide
Chem. 26
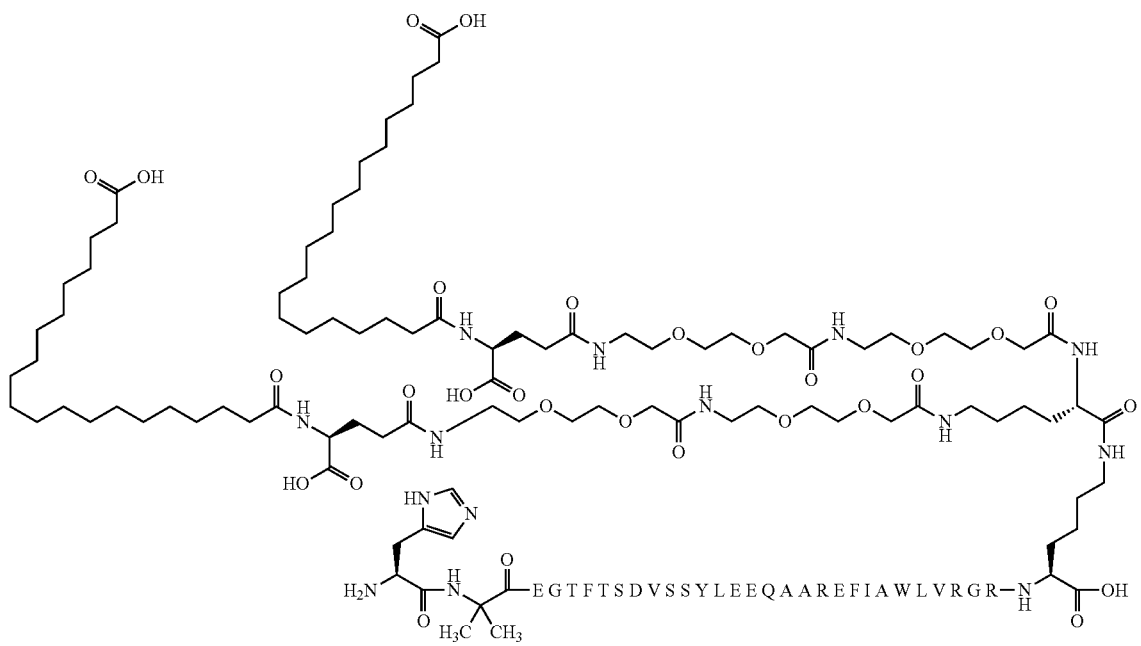
Synthesis method: SPPS_L; SC_L; CP_M1
UPLC02v01: Rt=10.7 min
LCMS01v01: Rt=2.6 min, m/3=1729; m/4=1297; m/5=1038

Example 7
N{Alpha}([Aib8,Glu22,Arg26,Arg34]-GLP-1-(7-37)-peptidyl)-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys
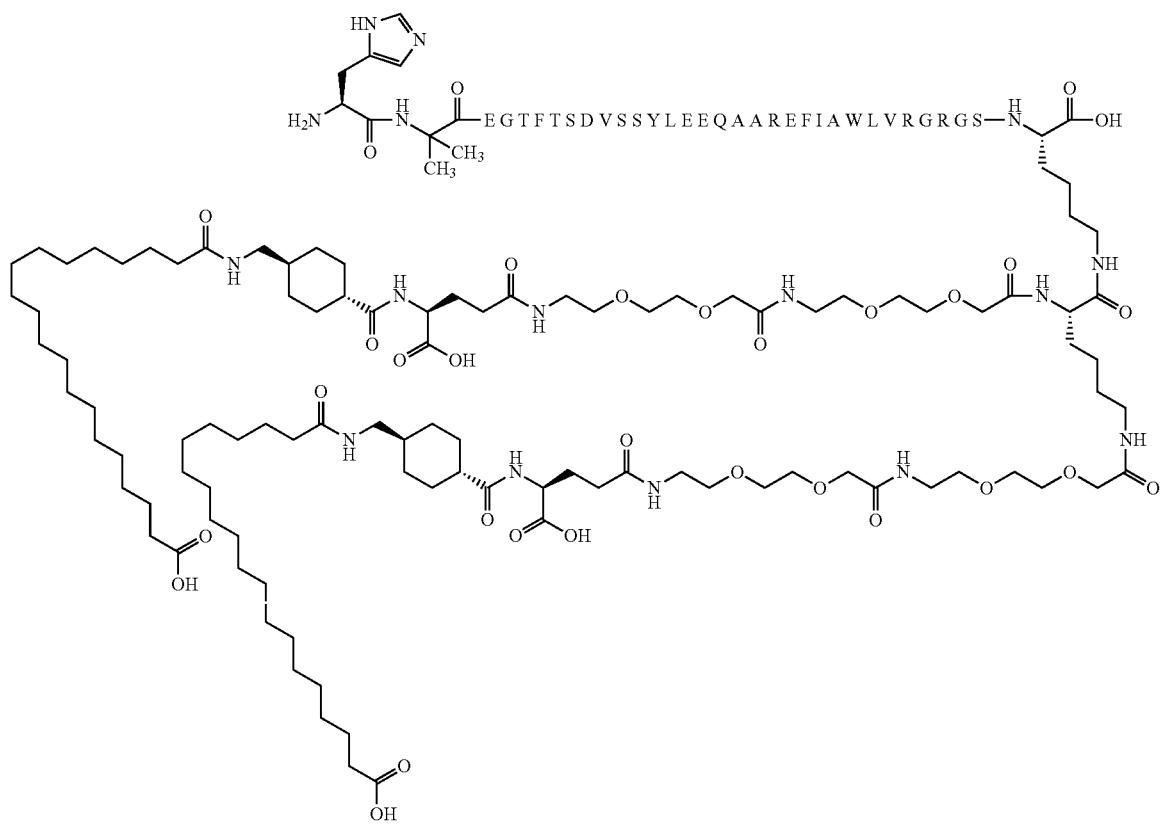
Chem. 27
The peptide is SEQ ID NO: 7.
Synthesis method: SPPS_P; SC_P; CP_M1
UPLC02v01: Rt=11.3 min
LCMS01v01: Rt=2.7 min, m/3=1841; m/4=1381; m/5=1105

Example 8
N{Alpha}([Aib8,Arg26,Arg34]-GLP-1-(7-37)-peptidyl)-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys
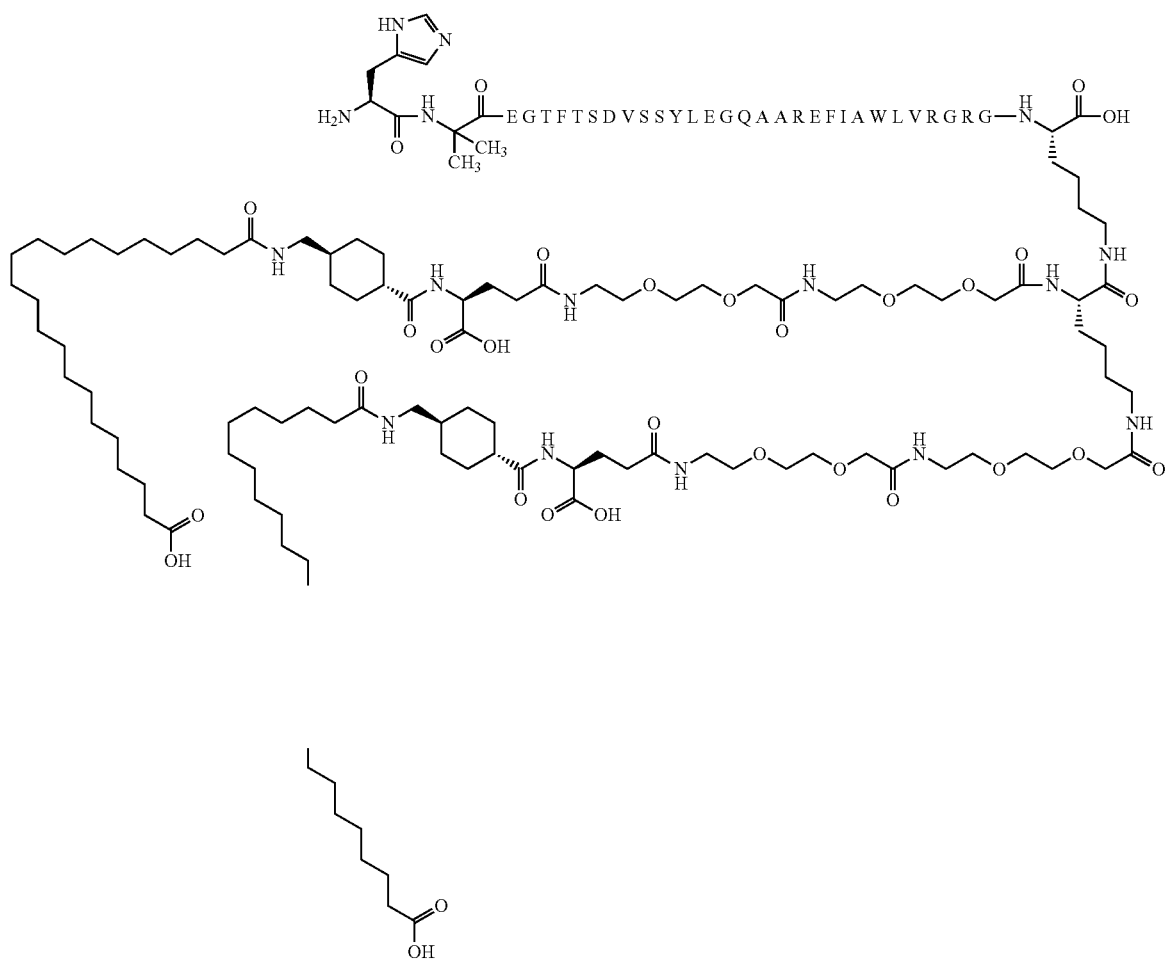
Chem. 28
The peptide is SEQ ID NO: 8.
Synthesis method: SPPS_P; SC_P; CP_M1
UPLC02v01: Rt=11.4 min
LCMS01v01: Rt=2.7 min, m/3=1817; m/4=1363; m/5=1090

Example 9

N{Alpha}([Aib8,Glu22,Arg26,Arg34]-GLP-1-(7-37)-peptidyl)-N{Epsilon}[(2S)-2,6-bis[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]hexanoyl]Lys

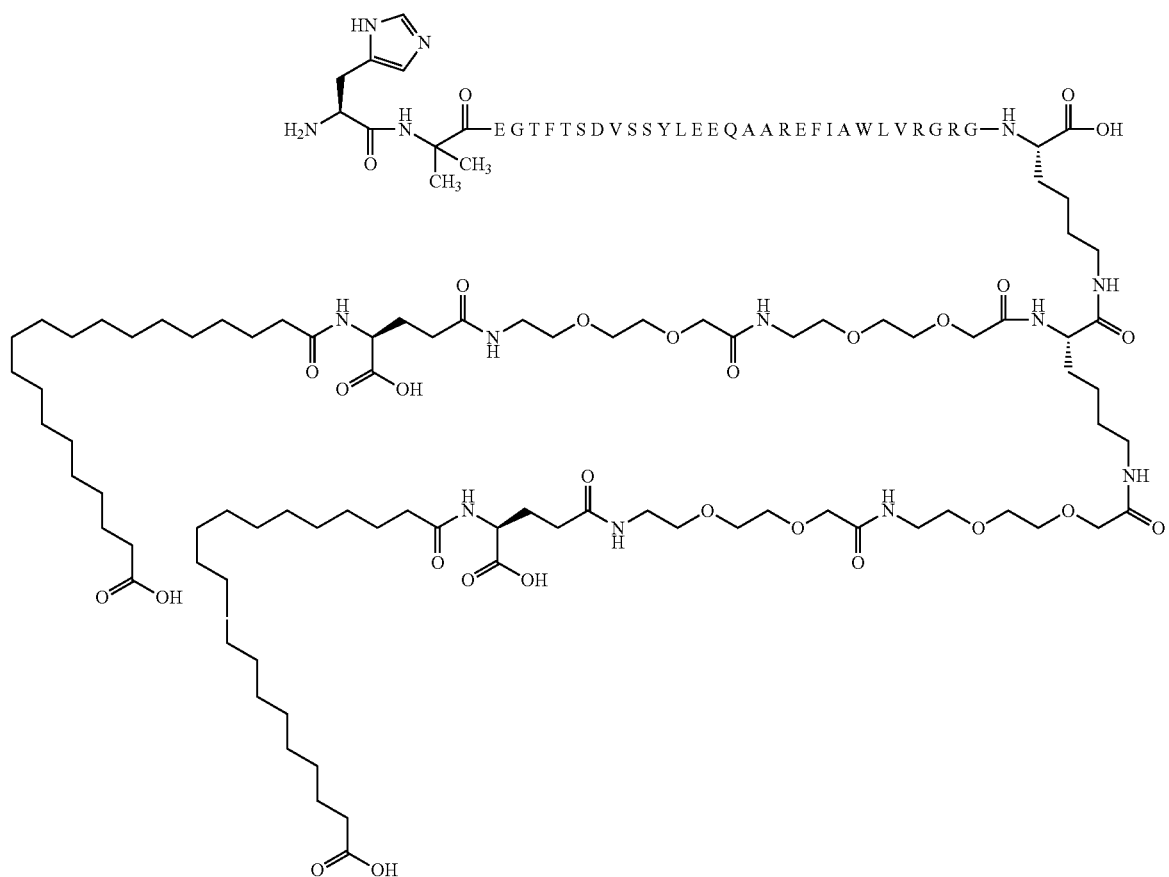

Chem. 29

The peptide is SEQ ID NO: 7.
Synthesis method: SPPS_P; SC_P; CP_M1
UPLC02v01: Rt=10.8 min
LCMS01v01: Rt=2.6 min, m/3=1748; m/4=1311; m/5=1049

Example 10

N{Epsilon-37}-[(2S)-2,6-bis[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Arg34, Lys37]-GLP-1-(7-37)-peptide Chem. 30

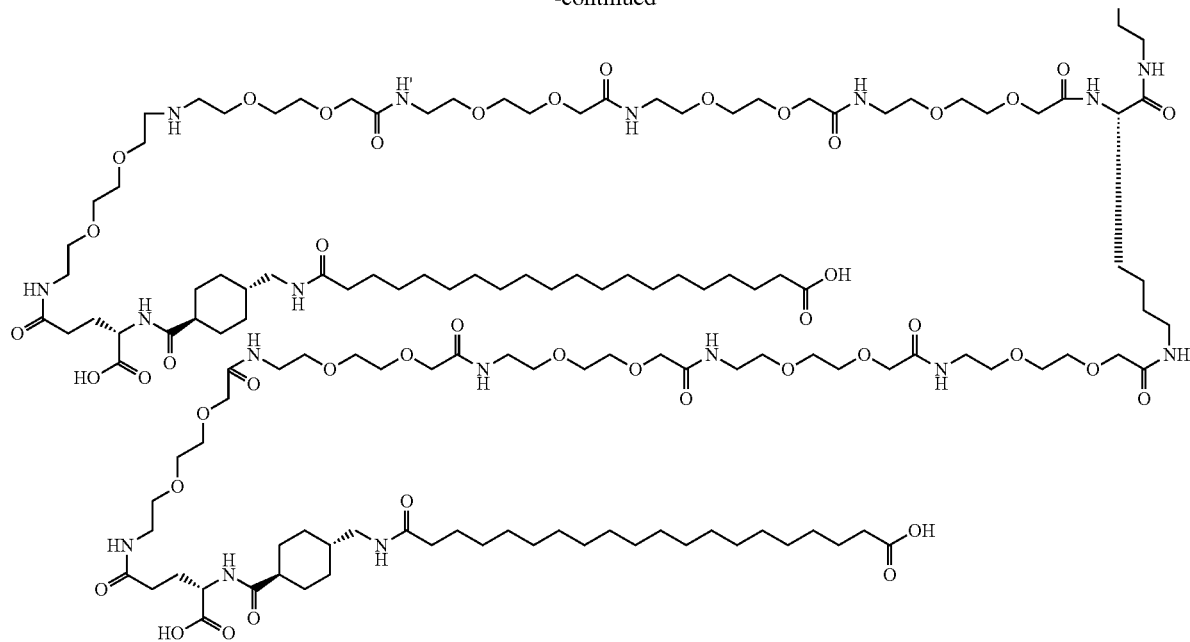
The peptide is SEQ ID NO: 6.
Synthesis method: SPPS_P; SC_P; CP_M1
UPLC02v01: Rt=9.7 min
LCMS01v01: Rt=2.7 min, m/4=1584; m/5=1268; m/6=1056
Example 11
N{Alpha}([Aib8,Arg26,Arg34]-GLP-1-(7-37)-peptidyl)-N{Epsilon}[(2S)-2,6-bis[[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]hexanoyl]Lys
Chem. 31
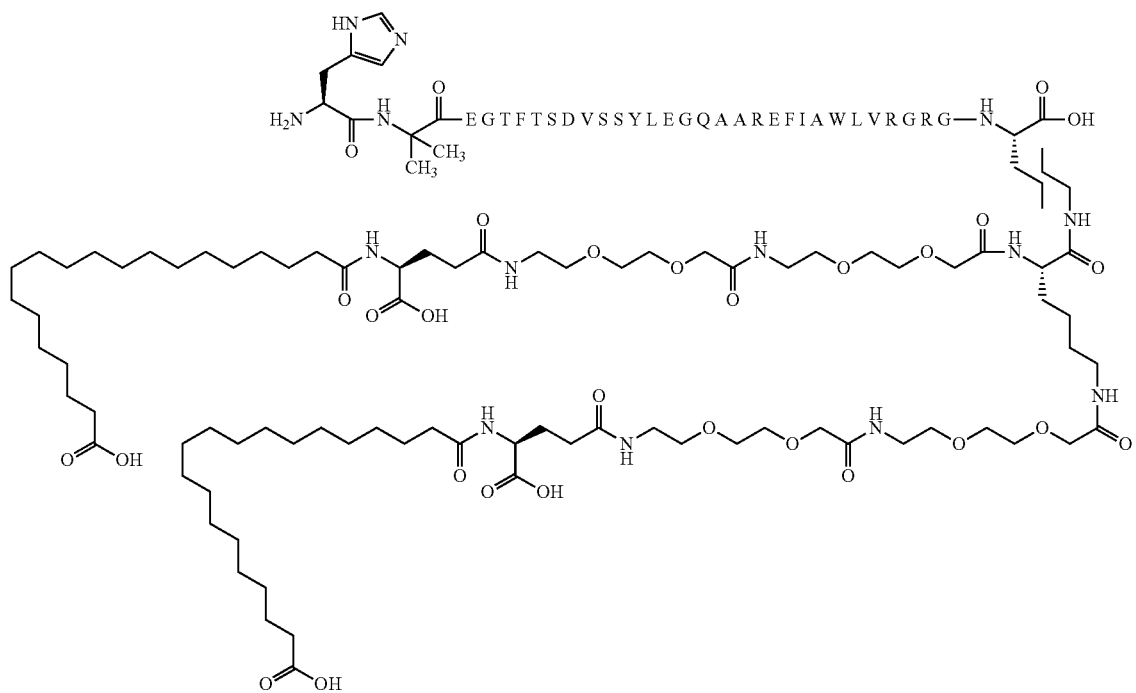

The peptide is SEQ ID NO: 8.
Synthesis method: SPPS_P; SC_P; CP_M1
UPLC02v01: Rt=10.8 min
LCMS01v01: Rt=2.6, m/3=1725; m/4=1294; m/5=1035

Example 12

[Aib8,Glu22,Arg26,Arg34]-GLP-1-(7-37)-peptidyl-Ser-Ser-Gly-Ala-Pro-N{Epsilon}[(2S)-2,6-bis[[2-[2-[2-[[2-[2-[2-[[(4S)-4-carboxy-4-[[4-[(19-carboxynonadecanoyl-amino)methyl]cyclohexanecarbonyl]amino]butanoyl]amino]ethoxy]ethoxy]acetyl]amino]ethoxy]ethoxy]acetyl]amino]hexanoyl]Lys Chem. 32

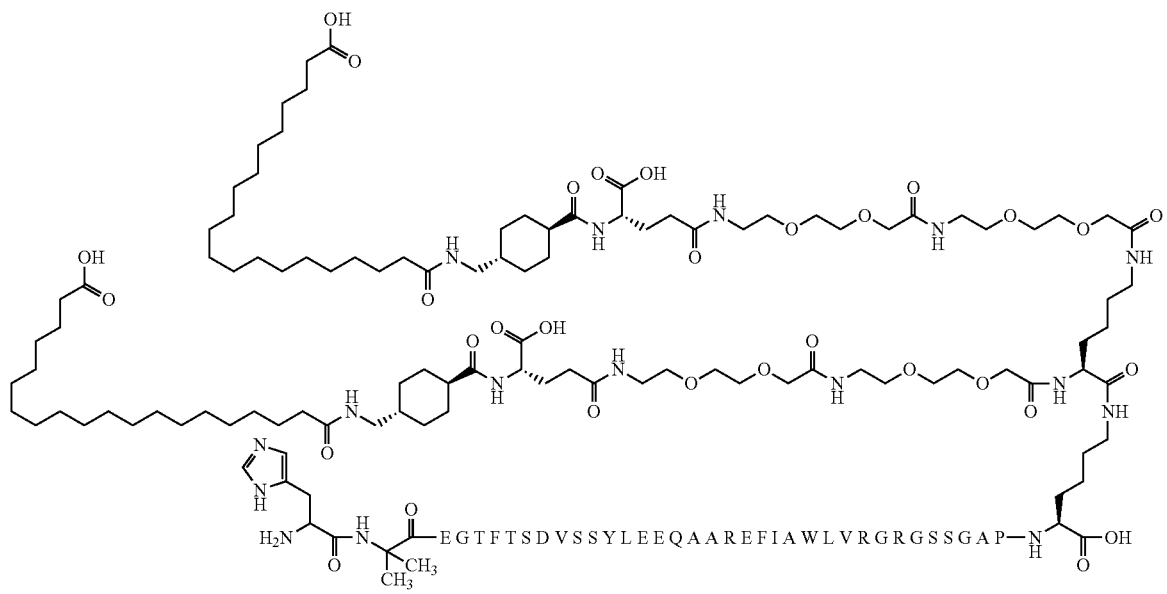

The peptide is SEQ ID NO: 9.
Synthesis method: SPPS_P; SC_P; CP_M1
UPLC02v01: Rt=11.2 min
LCMS01v01: Rt=2.7 min, m/4=1481; m/5=1186; m/6=988

Example 13

N{Epsilon-27}-[(2S)-2,6-bis[[2-[2-[2-[[2-[2-[2-[[2-[2-[2-[[2-[2-[2-[[(4S)-4-carboxy-4-[[4-[(19-carboxynonade-canoylamino)methyl]cyclohexanecarbonyl]amino]bu-tanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Lys27,Arg34]-GLP-1-(7-37)-peptide Chem. 33

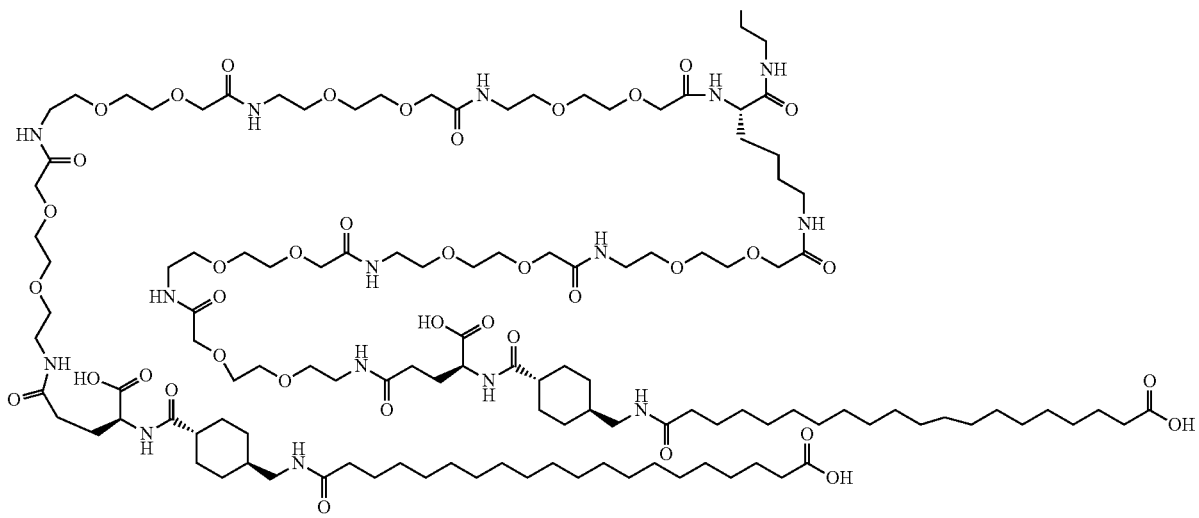
The peptide is SEQ ID NO: 10.
Synthesis method: SPPS_P; SC_P; CP_M1
UPLC02v01: Rt=11.1 min
LCMS01v01: Rt=2.5 min, m/3=1991; m/4=1493; m/5=1195
Example 14
N{Epsilon-27}-[(2S)-2,6-bis[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26, Lys27,Arg34]-GLP-1-(7-37)-peptide
Chem. 34
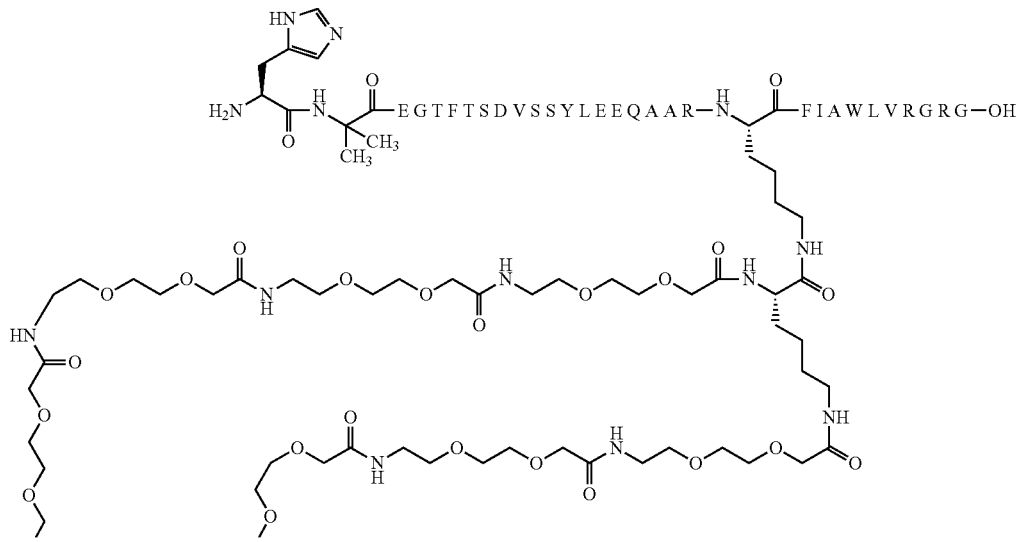

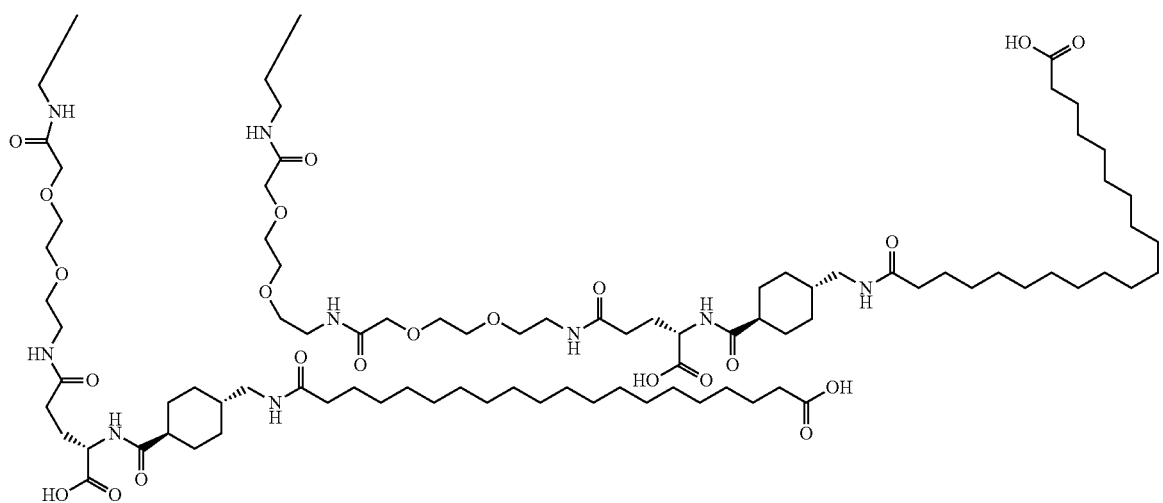
The peptide is SEQ ID NO: 10.
Synthesis method: SPPS_P; SC_P; CP_M1
UPLC02v01: Rt=11.0 min
LCMS01v01: Rt=2.5 min, m/4=1566; m/4=1253; m/5=1045
Example 15
N{Epsilon-37}-[(2S)-2,6-bis[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Arg34,Lys37]-GLP-1-(7-37)-peptide
Chem. 35
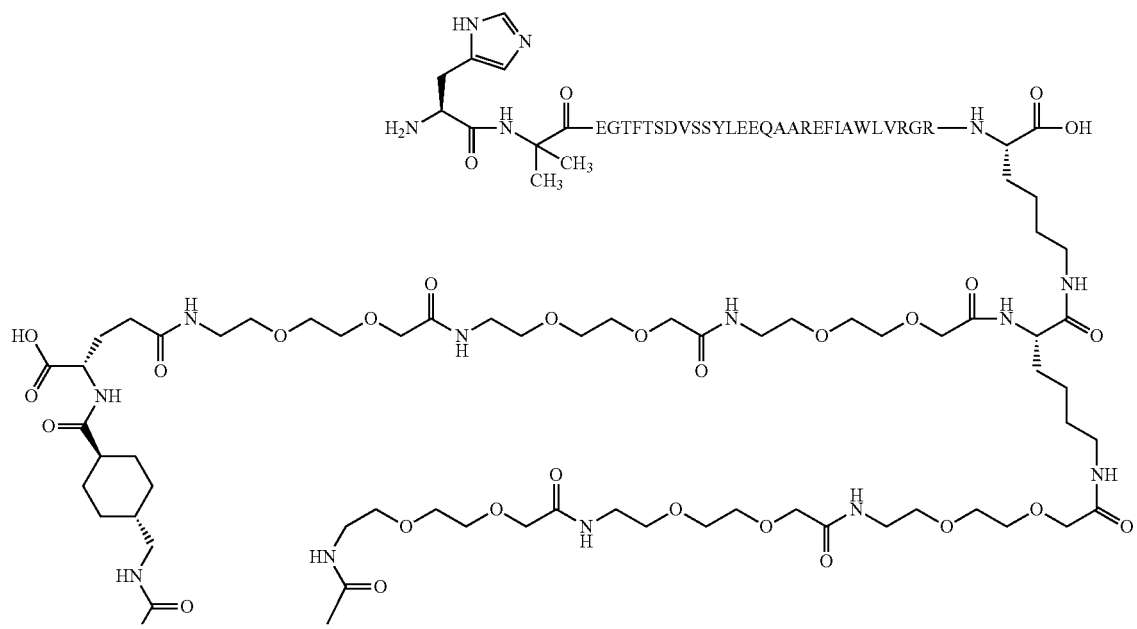

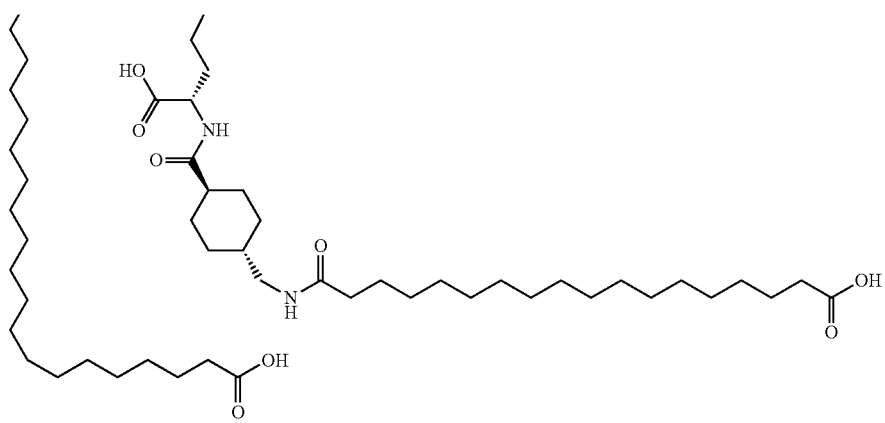
The peptide is SEQ ID NO: 6.
Synthesis method: SPPS_P; SC_P; CP_M1
UPLC02v01: Rt=11.1 min
LCMS01v01: Rt=2.1, m/3=1918; m/4=1439.3; m/5=1151
Example 16
N{Epsilon-37}-[(2S)-2,6-bis[[2-[2-[2-[[2-[2-[2-[[2-[2-[2-[[2-[2-[2-[[(4S)-4-carboxy-4-[[4-[(19-carboxynonade-canoylamino)methyl]cyclohexanecarbonyl]amino]bu-tanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Arg34,Lys37]-GLP-1-(7-37)-peptide
Chem. 36
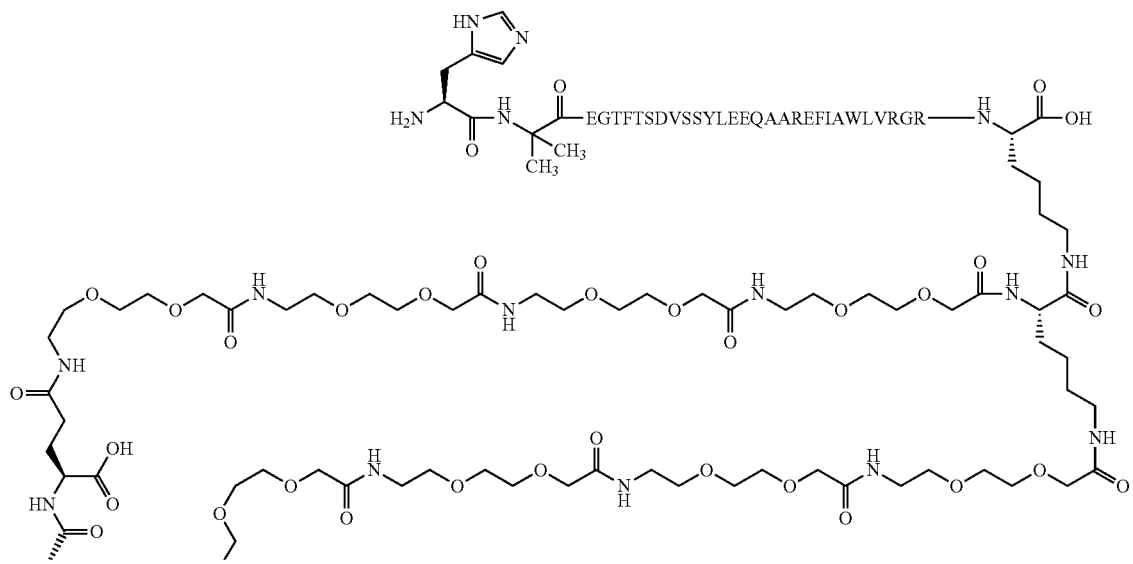

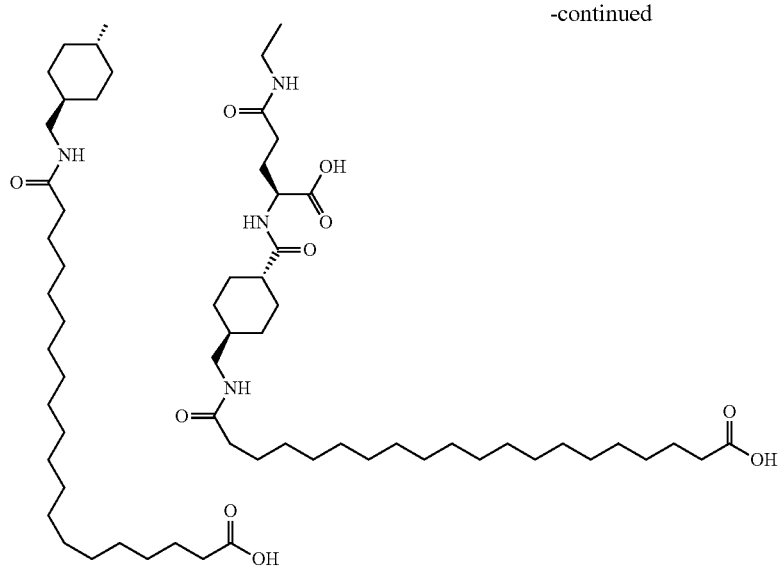
The peptide is SEQ ID NO: 6.
Synthesis method: SPPS_P; SC_P; CP_M1
UPLC02v01: Rt=12.4 min
LCMS01v01: Rt=2.1, m/4=1512; m/5=1210; m/6=1008
Example 17
N{Alpha}([Aib8,Arg26,Arg34]-GLP-1-(7-37)-peptidyl)-N{Epsilon}[(2S)-2,6-bis[[2-[2-[2-[[2-[2-[2-[[(4S)-4-carboxy-4-[[1-(19-carboxynonadecanoyl)piperidine-4-carbonyl]amino]butanoyl]amino]ethoxy]ethoxy]acetyl]amino]ethoxy]ethoxy]acetyl]amino]hexanoyl]Lys
Chem. 37
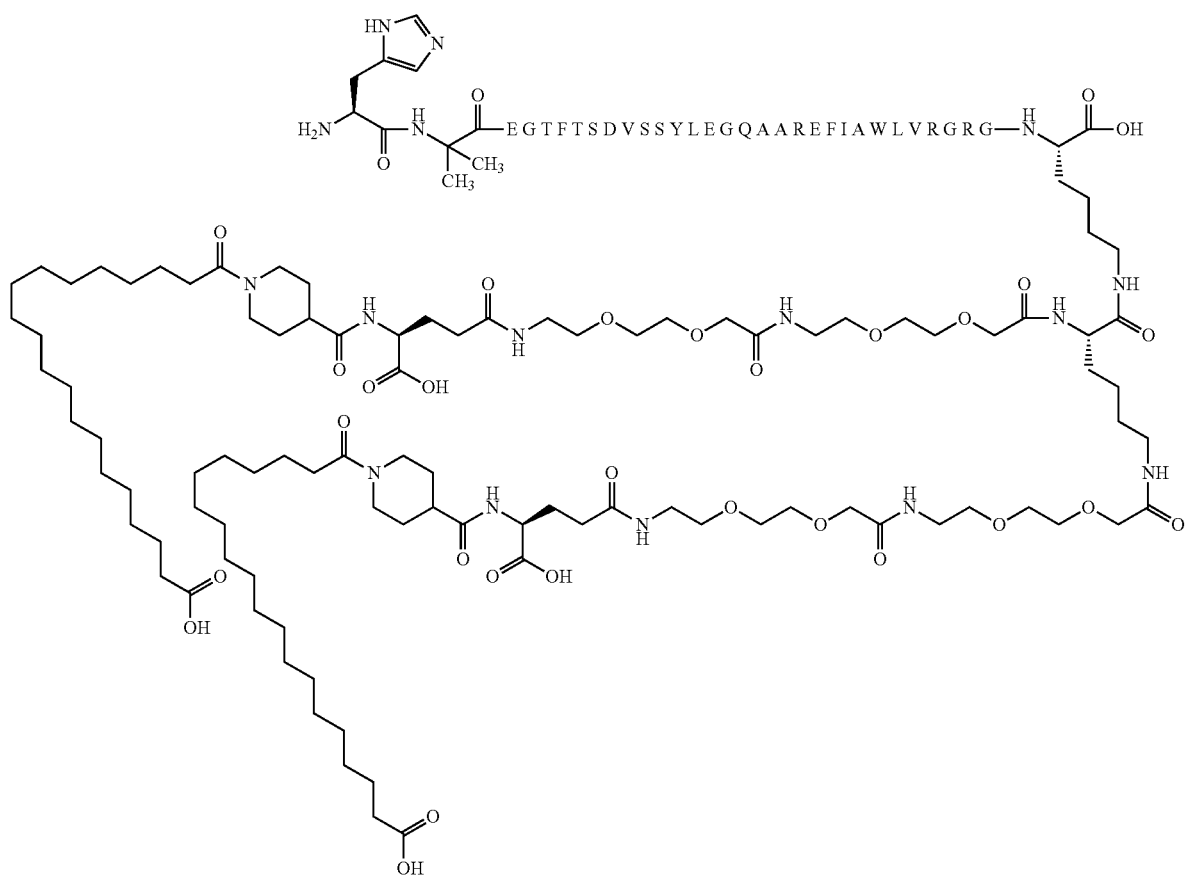

The peptide is SEQ ID NO: 8.
Synthesis method: SPPS_P; SC_P; CP_M1
UPLC02v01: Rt=11.2 min
LCMS01v01: Rt=2.7 min, m/3=1798; m/4=1349; m/5=1079

Example 18

N{Alpha}([Aib8,Glu22,Arg26,Arg34]-GLP-1-(7-37)-peptidyl)-N{Epsilon}[(2S)-2,6-bis[[2-[2-[2-[[2-[2-[2-[[(4S)-4-carboxy-4-[[1-(19-carboxynonadecanoyl)piperidine-4-carbonyl]amino]butanoyl]amino]ethoxy]ethoxy]acetyl]amino]ethoxy]ethoxy]acetyl]amino]hexanoyl]Lys Chem. 38

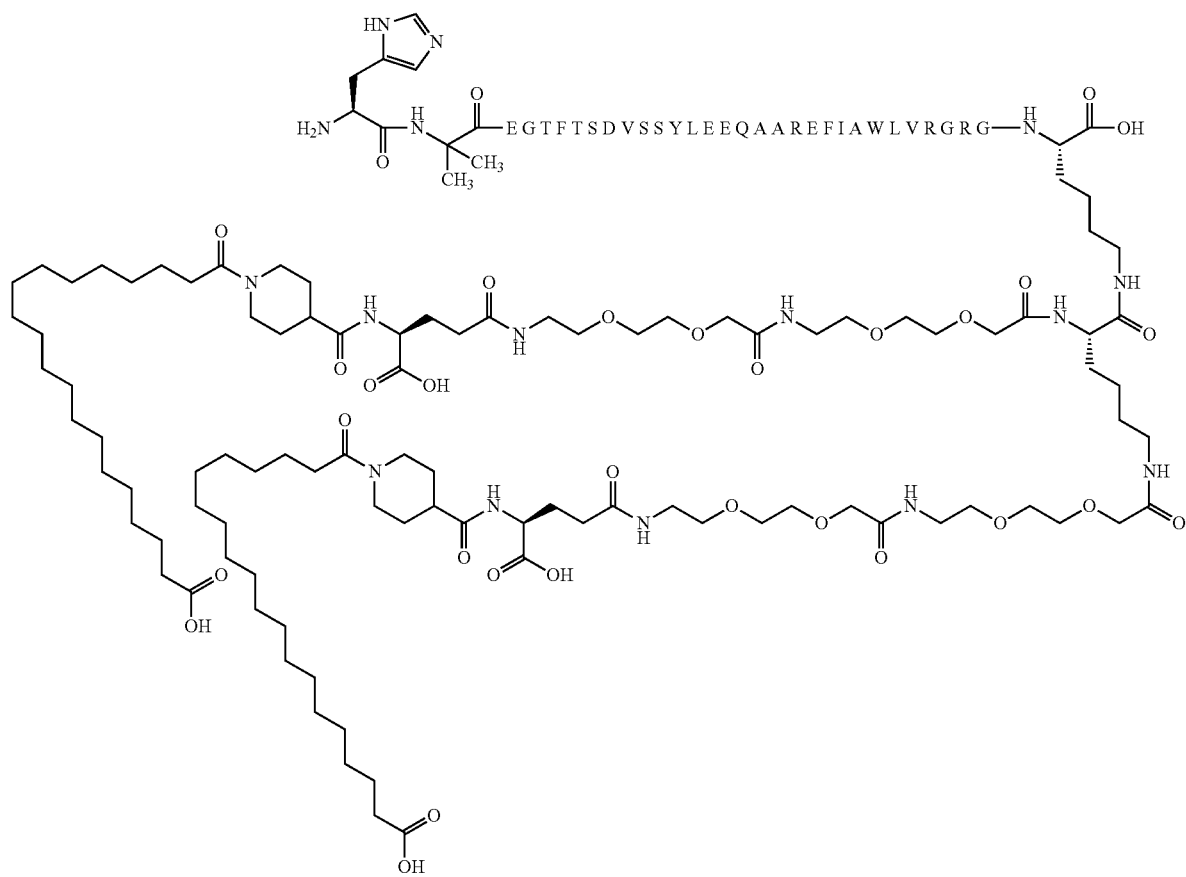

The peptide is SEQ ID NO: 7.
Synthesis method: SPPS_P; SC_P; CP_M1
UPLC02v01: Rt=11.2 min
MALDI01v01: calc. m/z=5464. found m/z=5464.

Example 19
N{Epsilon-27}-[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]-[Aib8,Glu22,Arg26,Lys27,Arg34]-GLP-1-(7-37)-peptide
Chem. 39
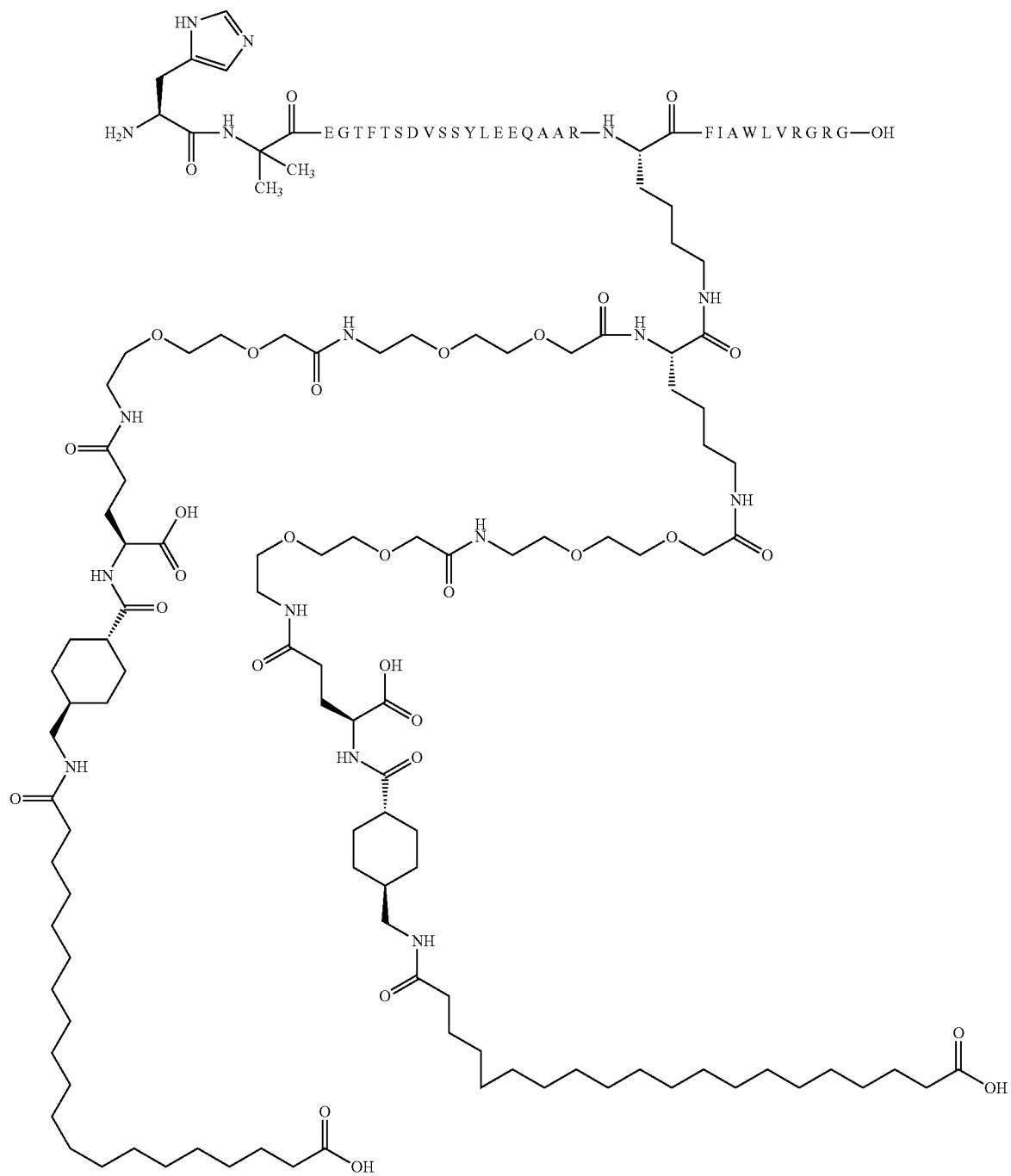
The peptide is SEQ ID NO: 10.
Synthesis method: SPPS_P; SC_P; CP_M1
UPLC02v01: Rt=10.8 min
LCMS01v01: Rt=2.6 min, m/4=1798; m/4=1349; m/5=1079

Example 20
N{Epsilon-27}-[(2S)-2,6-bis[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Lys27,Arg34]-GLP-1-(7-37)-peptide
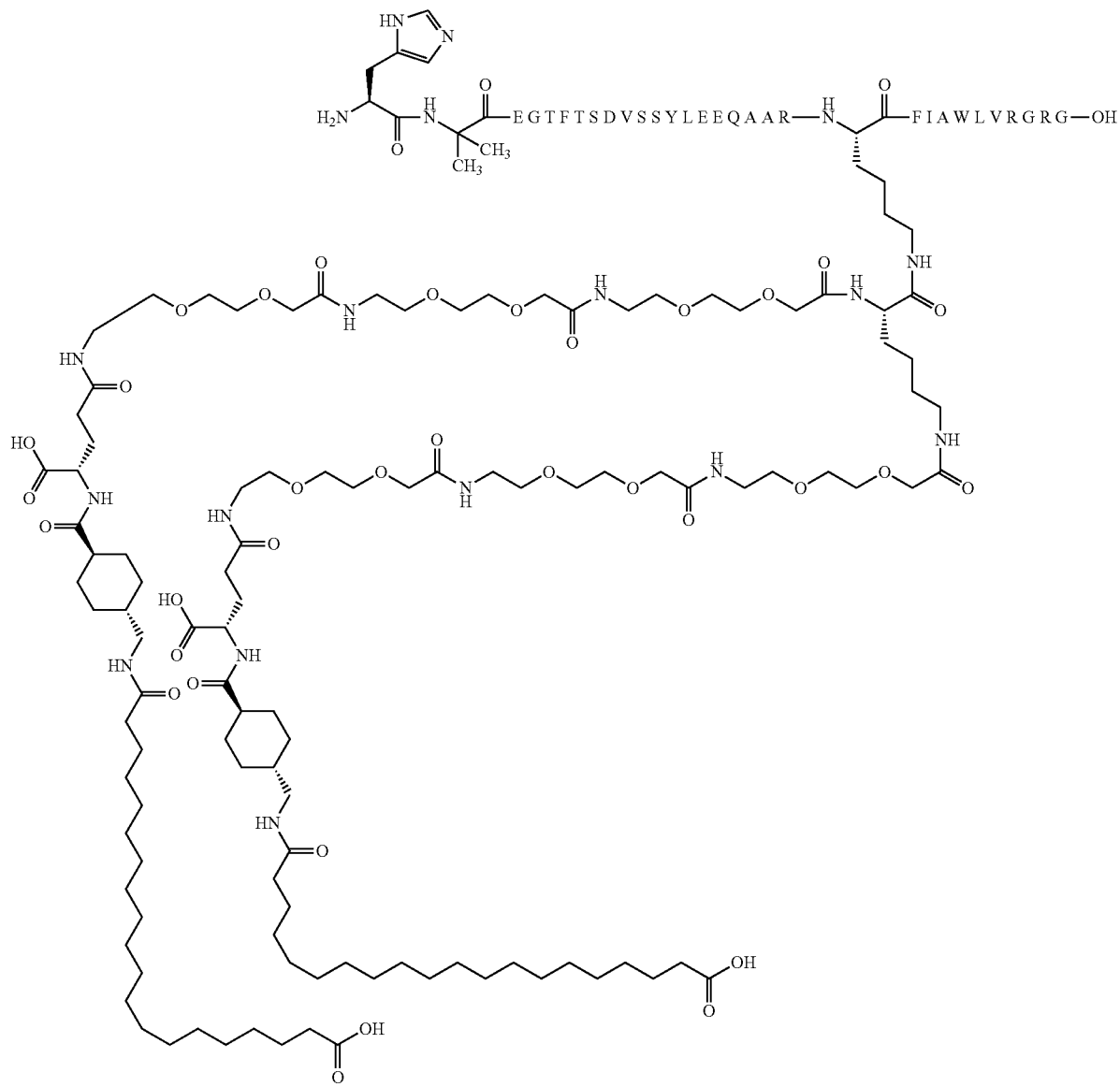
Chem. 40
The peptide is SEQ ID NO: 10.
Synthesis method: SPPS_P; SC_P; CP_M1
UPLC02v01: Rt=10.5 min
LCMS01v01: Rt=2.6 min, m/4=1894; m/4=1421; m/5=1137

Example 21

N{Epsilon-27}-[(2S)-2,6-bis[[2-[2-[2-[[2-[2-[2-[[2-[2-[2-[[2-[2-[2-[[2-[2-[2-[[(4S)-4-carboxy-4-[[4-[(21-carboxy-henicosanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26, Lys27,Arg34]-GLP-1-(7-37)-peptide Chem. 41

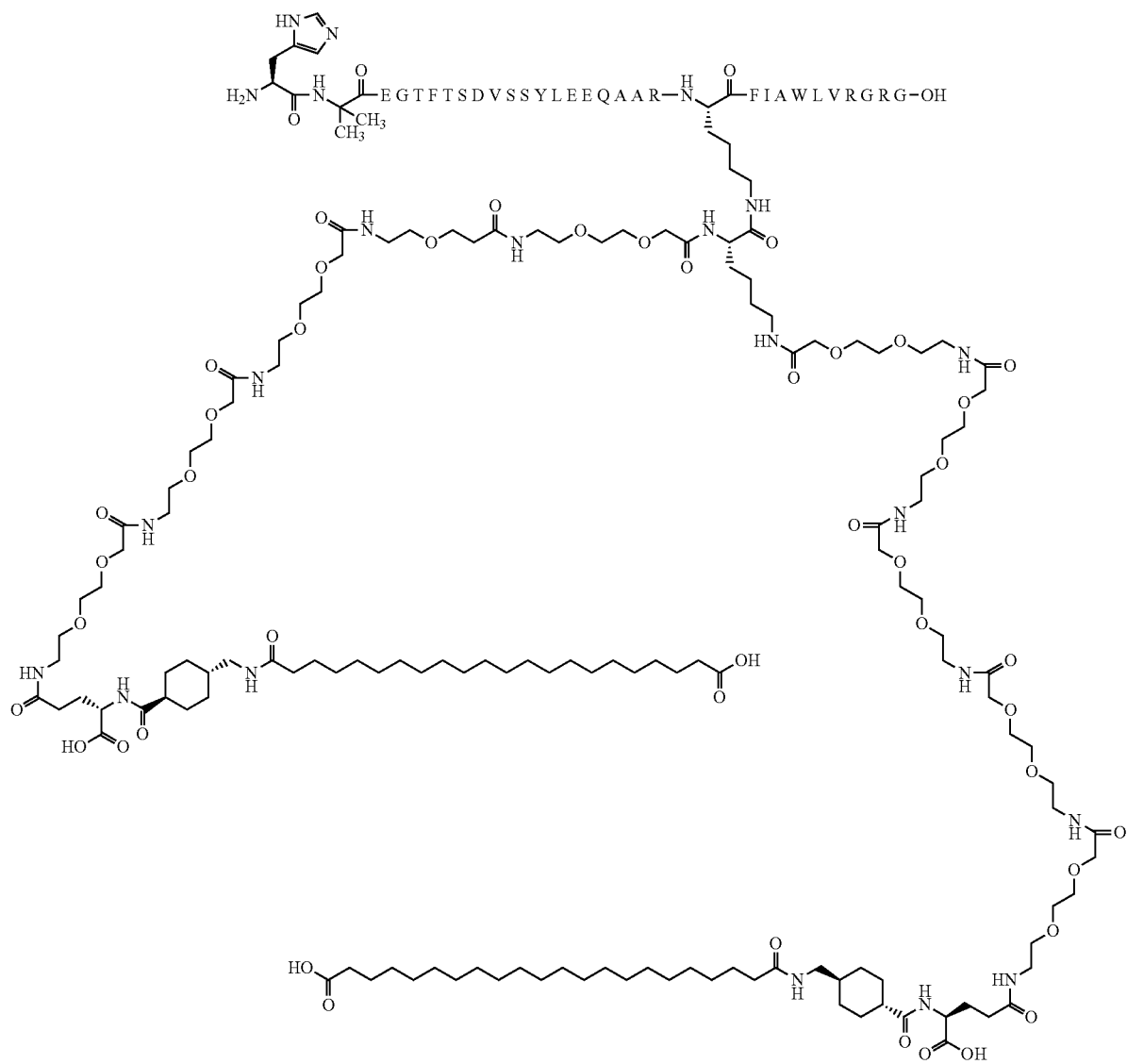

The peptide is SEQ ID NO: 10.
Synthesis method: SPPS_P; SC_P; CP_M1
UPLC02v01: Rt=11.9 min
LCMS01v01: Rt=2.8 min; m/4=1580; m/5=1265

Example 22

N{Epsilon-37}-[(2S)-2,6-bis[3-[2-[2-[2-[2-[3-[2-[2-[2-[2-[3-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethoxy]ethoxy]propanoylamino]ethoxy]ethoxy]ethoxy]ethoxy]propanoylamino]ethoxy]ethoxy]ethoxy]ethoxy]propanoylamino]hexanoyl]-[Aib8,Glu22,Arg26,Arg34,Lys37]-GLP-1-(7-37)-peptide

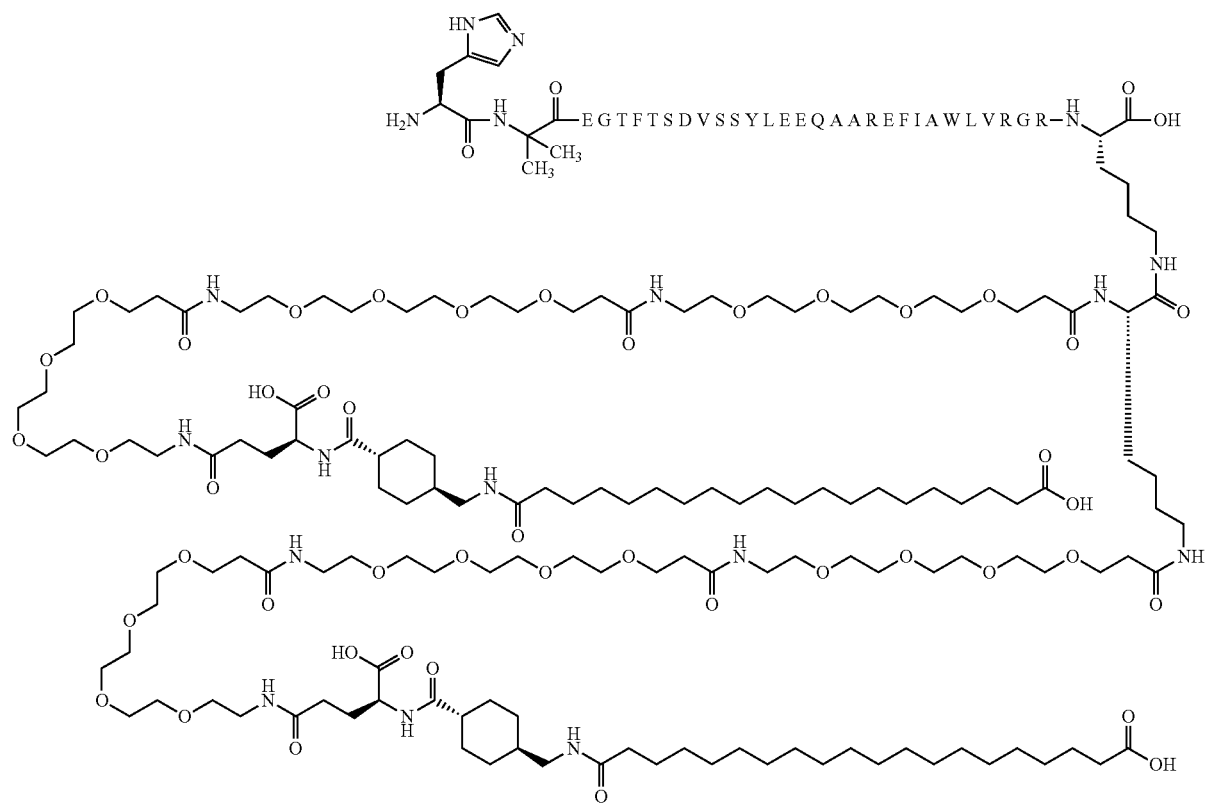

Chem. 42

The peptide is SEQ ID NO: 6.
Synthesis method: SPPS_P; SC_P; CP_M2
UPLC02v01: Rt=11.0 min
LCMS01v01: Rt=2.4; m/4=1593; m/5=1274

Example 23
N{Epsilon-37}-[(2S)-2,6-bis[3-[2-[2-[2-[2-[2-[2-[3-[2-[2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]ethoxy]ethoxy]ethoxy]propanoylamino]ethoxy]ethoxy]ethoxy]ethoxy]ethoxy]ethoxy]propanoylamino]hexanoyl]-[Aib8,Glu22,Arg26,Arg34,Lys37]-GLP-1-(7-37)-peptide
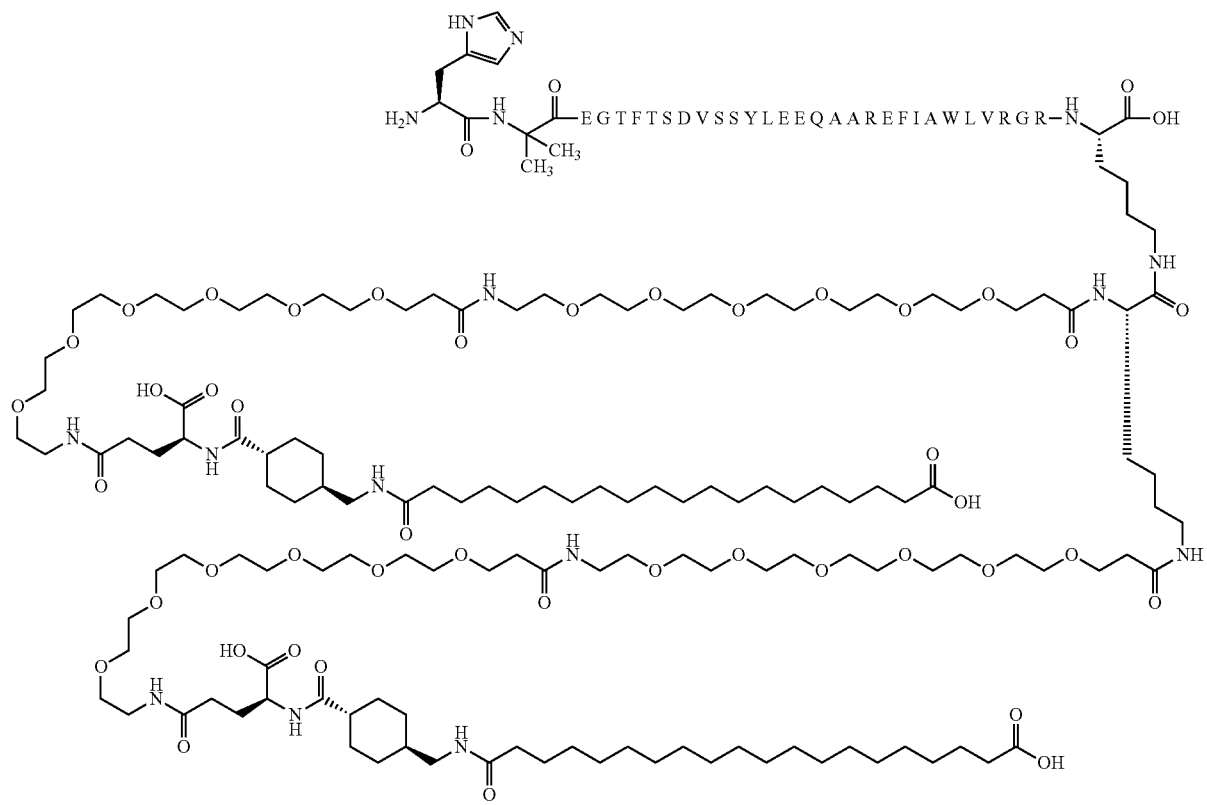
Chem. 43
The peptide id SEQ ID NO: 6.
Synthesis method: SPPS_P; SC_P; CP_M2
UPLC02v01: Rt=11.1 min
LCMS01v01: Rt=2.4; m/4=1556; m/5=1246

Example 24
N{Epsilon-37}-[(2S)-2,6-bis[3-[2-[2-[2-[2-[2-[2-[2-[2-[2-[2-[2-[2-[[(4S)-4- carboxy-4-[[4-[(19-carboxynonadecanoy-lamino)methyl]cyclohexanecarbonyl]amino]butanoyl]amino]ethoxy]ethoxy]ethoxy]ethoxy]ethoxy]ethoxy]ethoxy]ethoxy]ethoxy]ethoxy]ethoxy]propanoylamino]hexanoyl]-[Aib8,Glu22,Arg26,Arg34,Lys37]-GLP-1-(7-37)-peptide
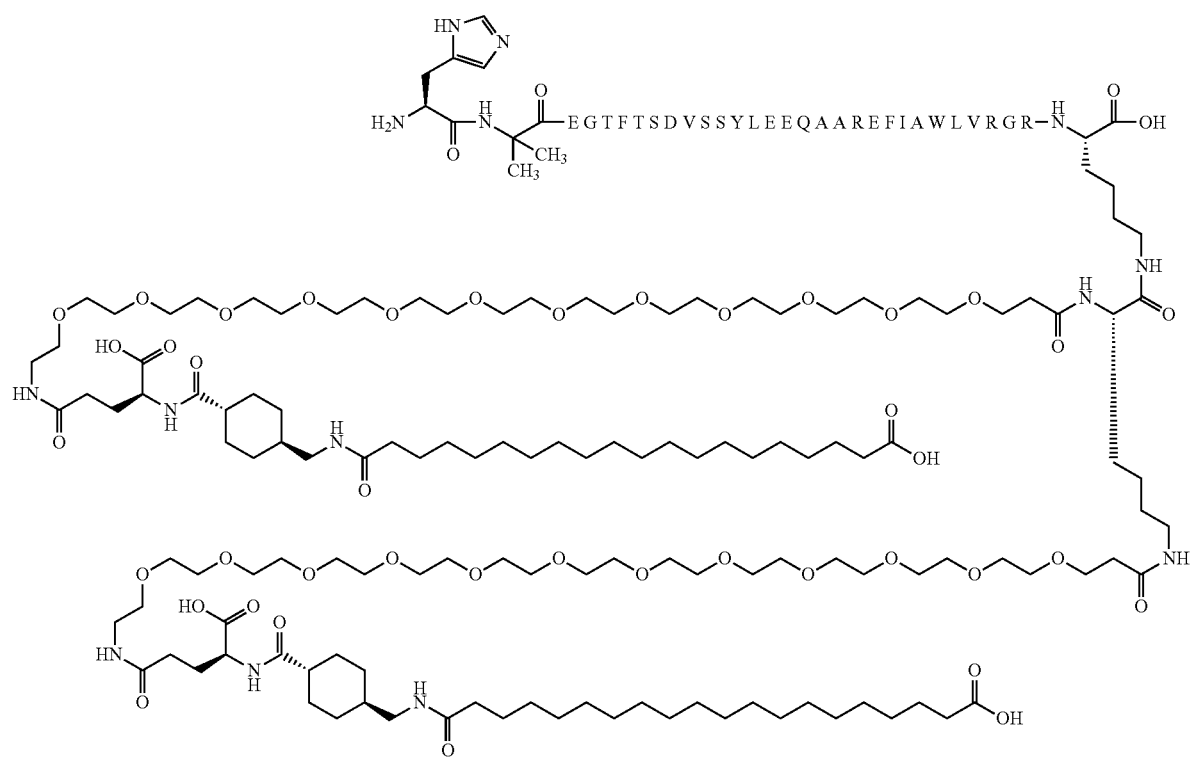
Chem. 44
The peptide is SEQ ID NO: 6.
Synthesis method: SPPS_P; SC_P; CP_M2
UPLC02v01: Rt=11.3 min
LCMS01v01: Rt=2.7; m/4=1521; m/5=1217

Example 25

N{Epsilon-37}-[(2S)-2,6-bis[3-[2-[2-[2-[2-[2-[2-[2-[2-[2-[2-[2-[2-[2-[2-[[(4S)-4carboxy-4-[[4-[(19-carboxynonadecanoylamino)methyl]cyclohexanecarbonyl]amino]butanoyl]amino]ethoxy]ethoxy]ethoxy]ethoxy]ethoxy]ethoxy]ethoxy]ethoxy]ethoxy]ethoxy]ethoxy]ethoxy]ethoxy]ethoxy]propanoylamino]hexanoyl]-[Aib8,Glu22,Arg26,Arg34,Lys37]-GLP-1-(7-37)-peptide Chem. 45

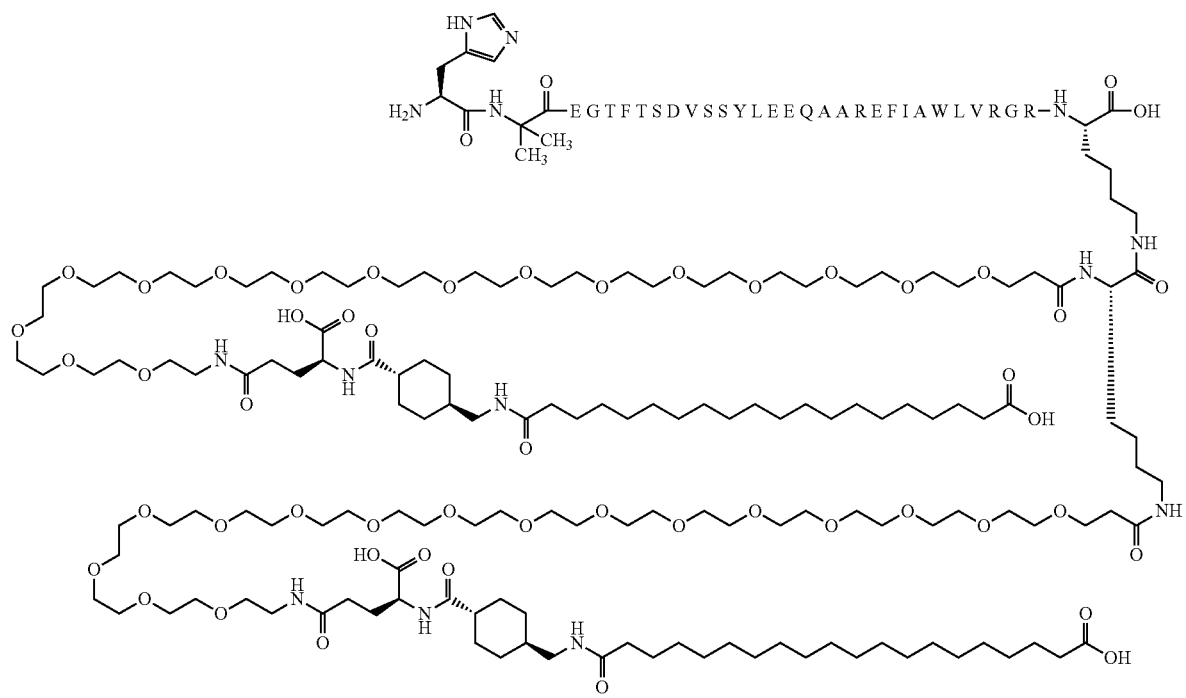

The peptide is SEQ ID NO: 6.
Synthesis method: SPPS_P; SC_P; CP_M1
UPLC02v01: Rt=11.2 min
LCMS01v01: Rt=2.8, m/4=1288, m/5=1609

Example 26

[Aib8,Glu22,Arg26,Arg34]-GLP-1-(7-37)-peptidyl-Ala-Glu-Ala-Pro-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys Chem. 46
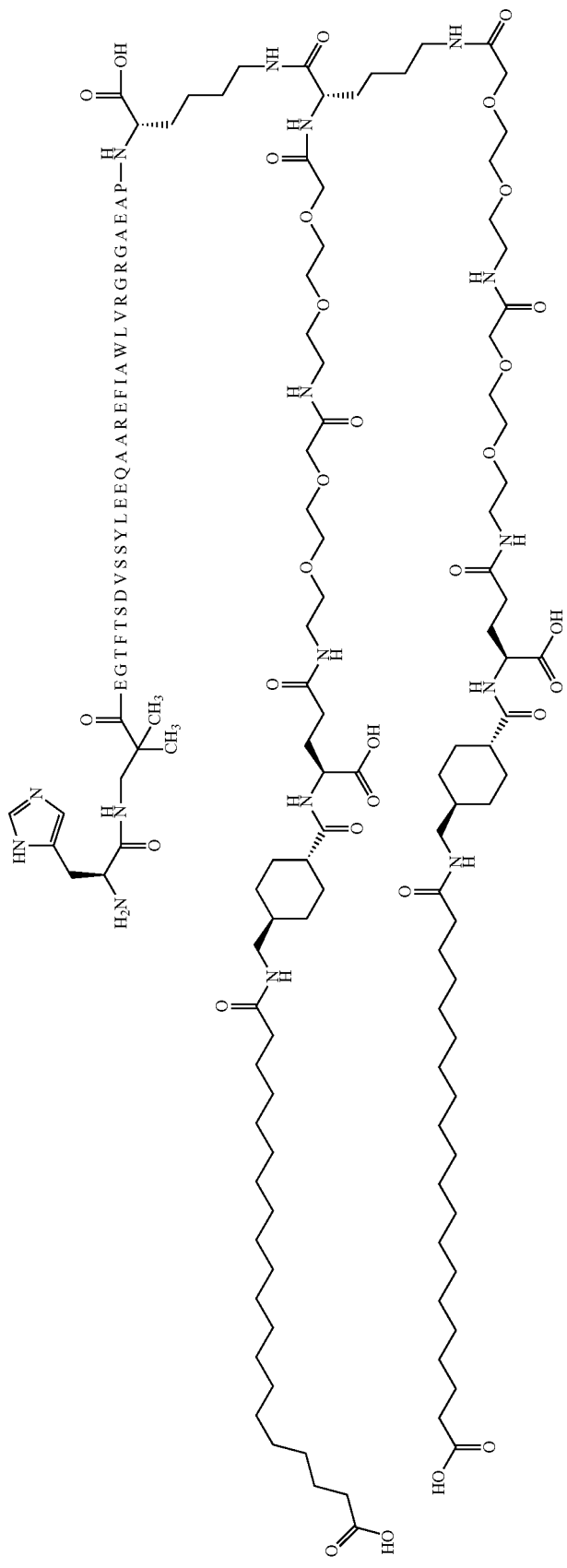

The peptide is SEQ ID NO: 11.
Synthesis method: SPPS_P; SC_P; CP_M1
UPLC02v01: Rt=11.2 min
LCMS01v01: Rt=2.7; m/4=1473; m/5=1179

Example 27

[Aib8,Glu22,Arg26,Arg34]-GLP-1-(7-37)-peptidyl-Glu-Pro-Pro-Gly-N{Epsilon}[(2S)-2,6-bis[[2-[2-[2-[[2-[2-[2-[[(4S)-4-carboxy-4-[[4-[(19-carboxynonadecanoylamino) methyl]cyclohexanecarbonyl]amino]butanoyl]amino] ethoxy]ethoxy]acetyl]amino]ethoxy]ethoxy]acetyl]amino] hexanoyl]Lys Chem. 47
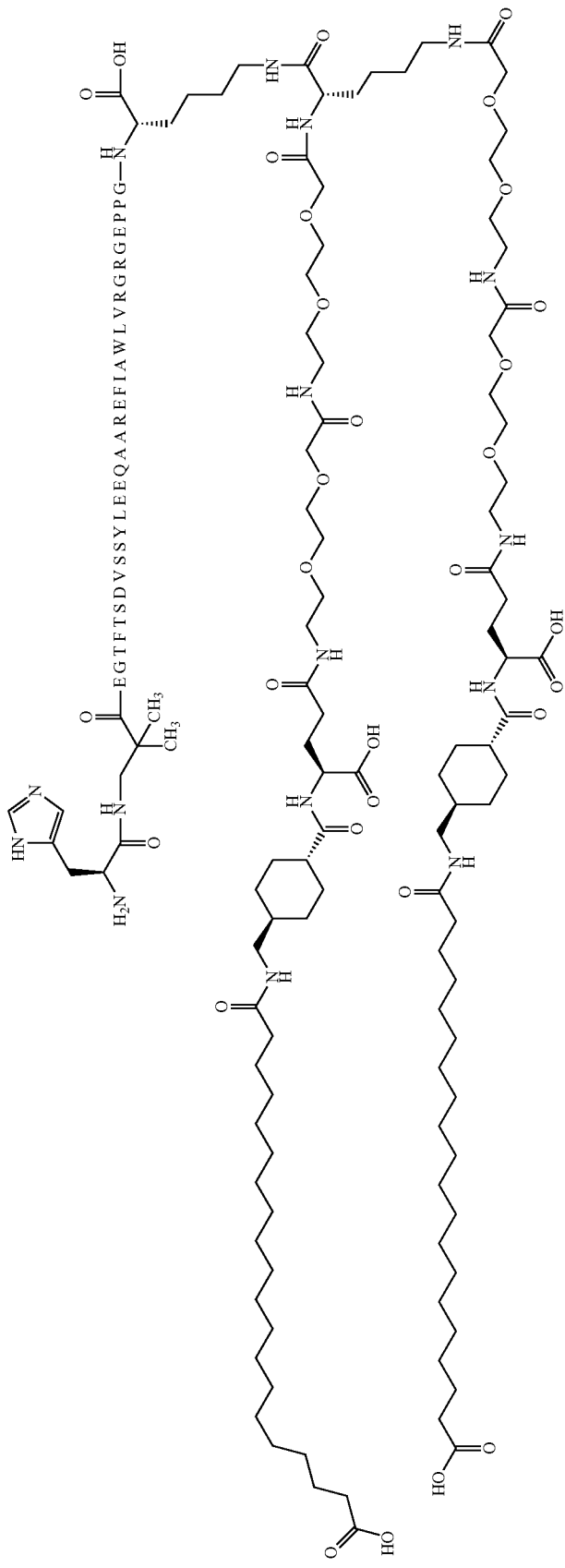

The peptide is SEQ ID NO: 12.
Synthesis method: SPPS_P; SC_P; CP_M1
UPLC02v01: Rt=11.2 min
LCMS01v01: Rt=2.8; m/4=1476; m/5=1181

Example 28

[Aib8,Glu22,Arg26,Arg34]-GLP-1-(7-37)-peptidyl-Pro-Ala-Glu-Glu-N{Epsilon}[(2S)-2,6-bis[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl]Lys

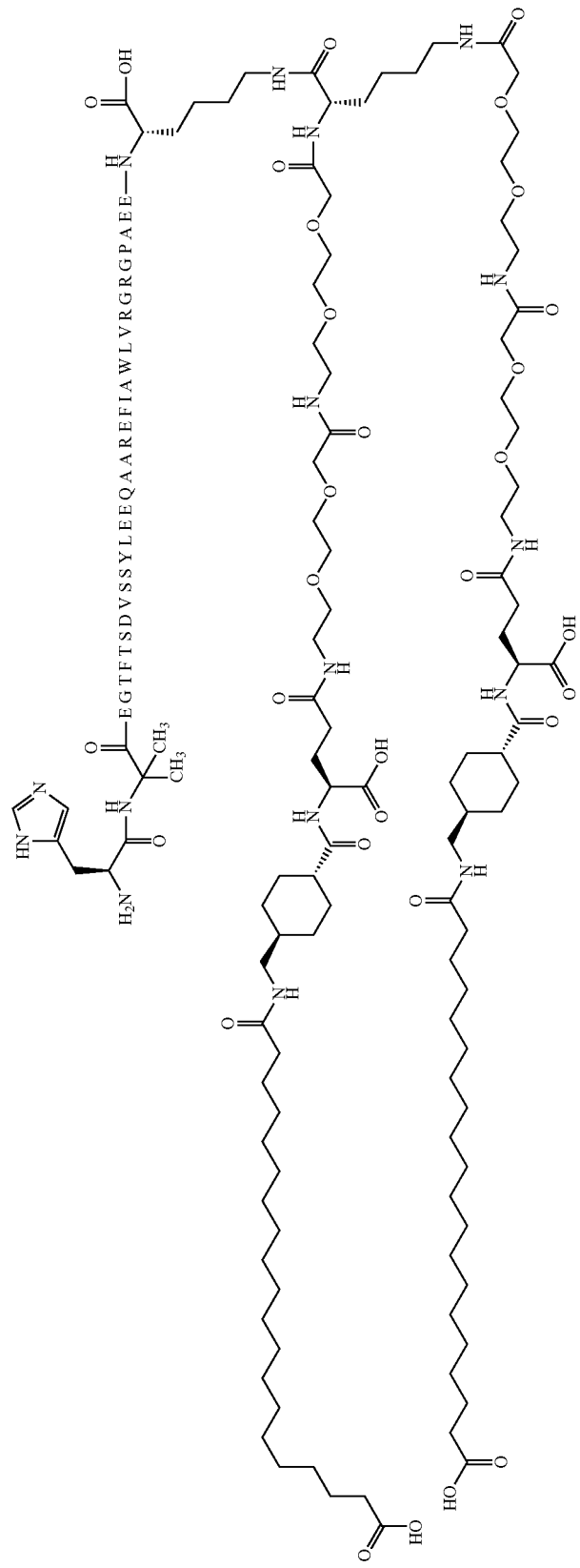
Chem. 48

The peptide is SEQ ID NO: 13.
Synthesis method: SPPS_P; SC_P; CP_M1
UPLC02v01: Rt=11.2 min
LCMS01v01: Rt=2.8; m/4=1488; m/5=1190

Example 29

[Aib8,Glu22,Arg26,Arg34]-GLP-1-(7-37)-peptidyl-Ser-Ser-Pro-Ala-Ala-N{Epsilon}[(2S)-2,6-bis[[2-[2-[2-[[2-[2-[2-[[(4S)-4-carboxy-4-[[4-[(19-carboxynonadecanoy-lamino)methyl]cyclohexanecarbonyl]amino]butanoyl]amino]ethoxy]ethoxy]acetyl]amino]ethoxy]ethoxy]acetyl]amino]hexanoyl]Lys

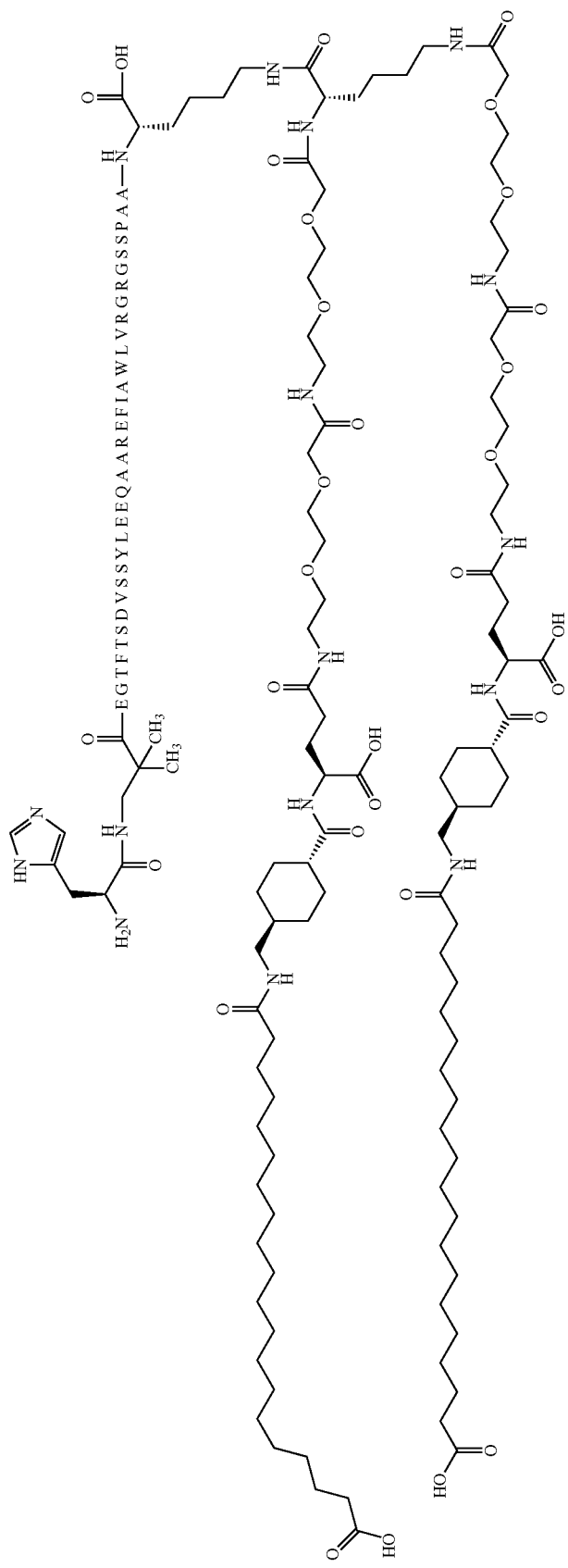
Chem. 49

The peptide is SEQ ID NO: 14.
Synthesis method: SPPS_P; SC_P; CP_M1
UPLC02v01: Rt=11.2 min
LCMS01v01: Rt=2.8; m/4=1484; m/5=1188

Example 30

[Aib8,Glu22,Arg26,Arg34]-GLP-1-(7-37)-peptidyl-Ser-Ser-Ala-Glu-Gly-N{Epsilon}[(2S)-2,6-bis[[2-[2-[2-[[2-[2-[2-[[(4S)-4-carboxy-4-[[4-[(19-carboxynonadecanoy-lamino)methyl]cyclohexanecarbonyl]amino]butanoyl]amino]ethoxy]ethoxy]acetyl]amino]ethoxy]ethoxy]acetyl]amino]hexanoyl]Lys

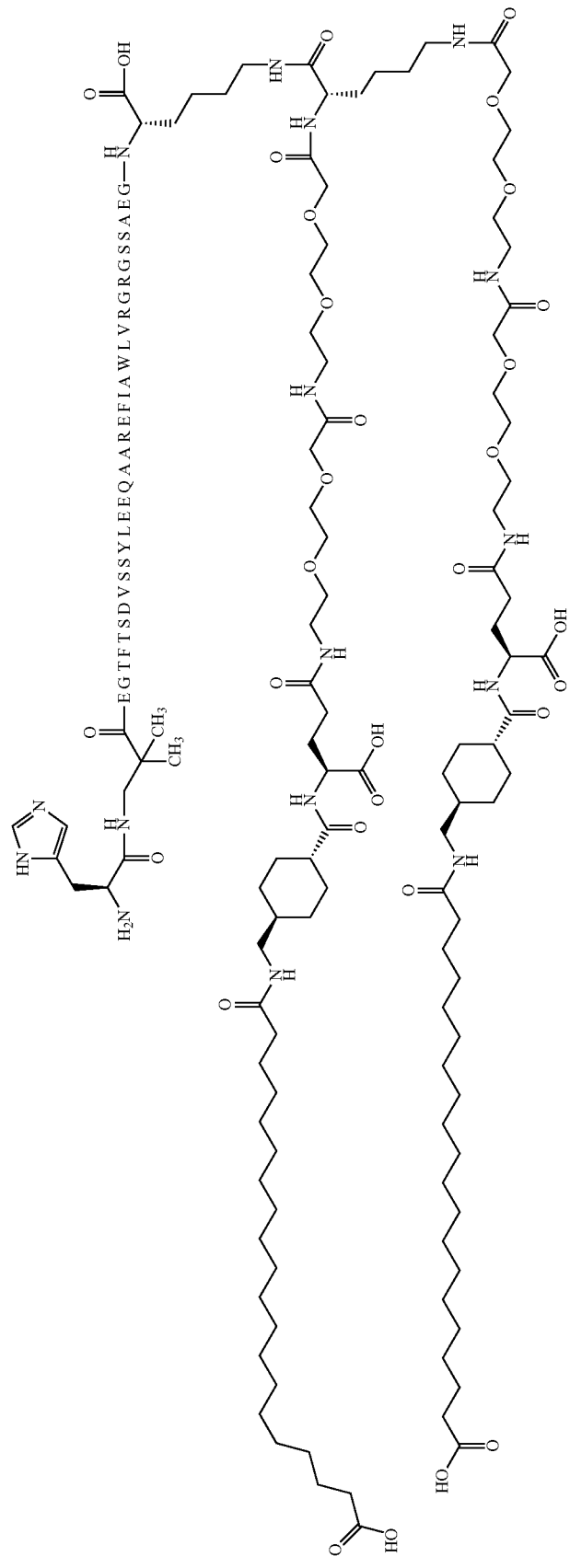
Chem. 50

The peptide is SEQ ID NO: 15.
Synthesis method: SPPS_P; SC_P; CP_M1
UPLC02v01: Rt=11.2 min
LCMS01v01: Rt=2.8; m/4=1489; m/5=1191

Example 31

[Aib8,Glu22,Arg26,Arg34]-GLP-1-(7-37)-peptidyl-Ser-Ser-Glu-Ala-Glu-N{Epsilon}[(2S)-2,6-bis[[2-[2-[2-[[2-[2-[2-[[(4S)-4-carboxy-4-[[4-[(19-carboxynonadecanoy-lamino)methyl]cyclohexanecarbonyl]amino]butanoyl]amino]ethoxy]ethoxy]acetyl]amino]ethoxy]ethoxy]acetyl]amino]hexanoyl]Lys Chem. 51
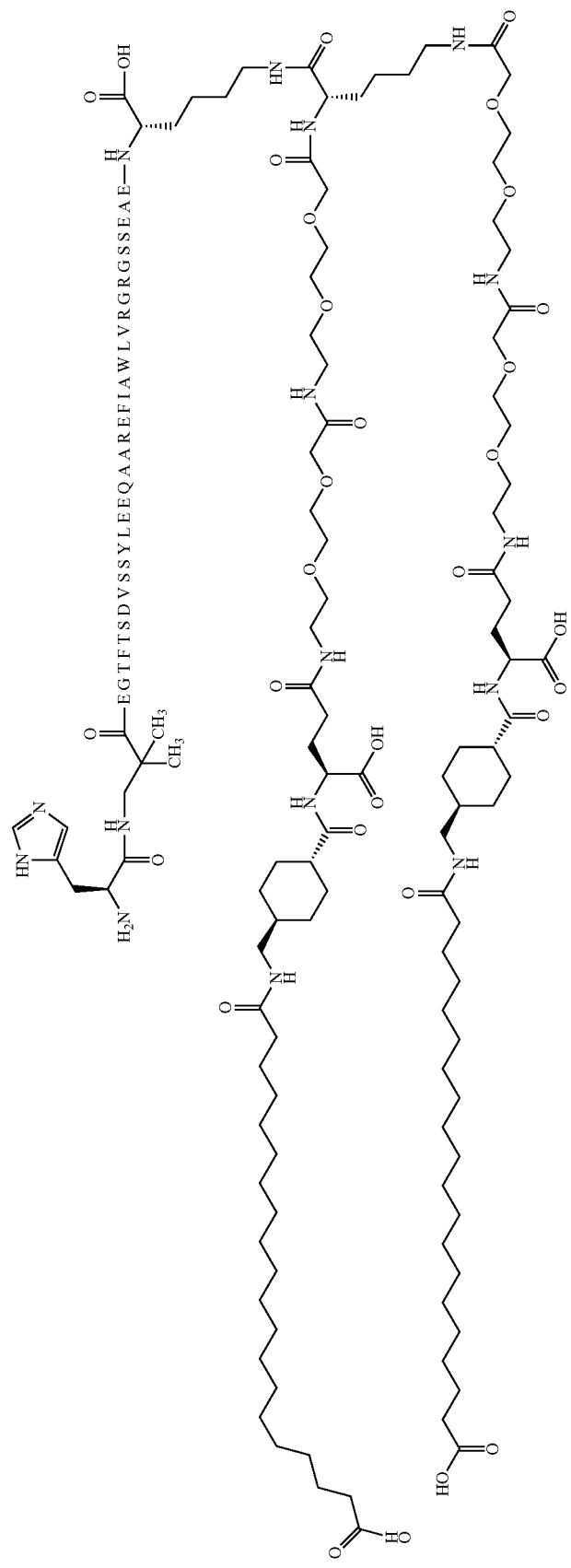

The peptide is SEQ ID NO: 16.
Synthesis method: SPPS_P; SC_P; CP_M1
UPLC02v01: Rt=11.19 min
LCMS01v01: Rt=2.8; m/4=1506; m/5=1205

Example 32

N{Epsilon-37}-[(2S)-2,6-bis[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Aib8,Glu22,Arg26,Arg34,Lys37]-GLP-1-(7-37)-peptide Chem. 52

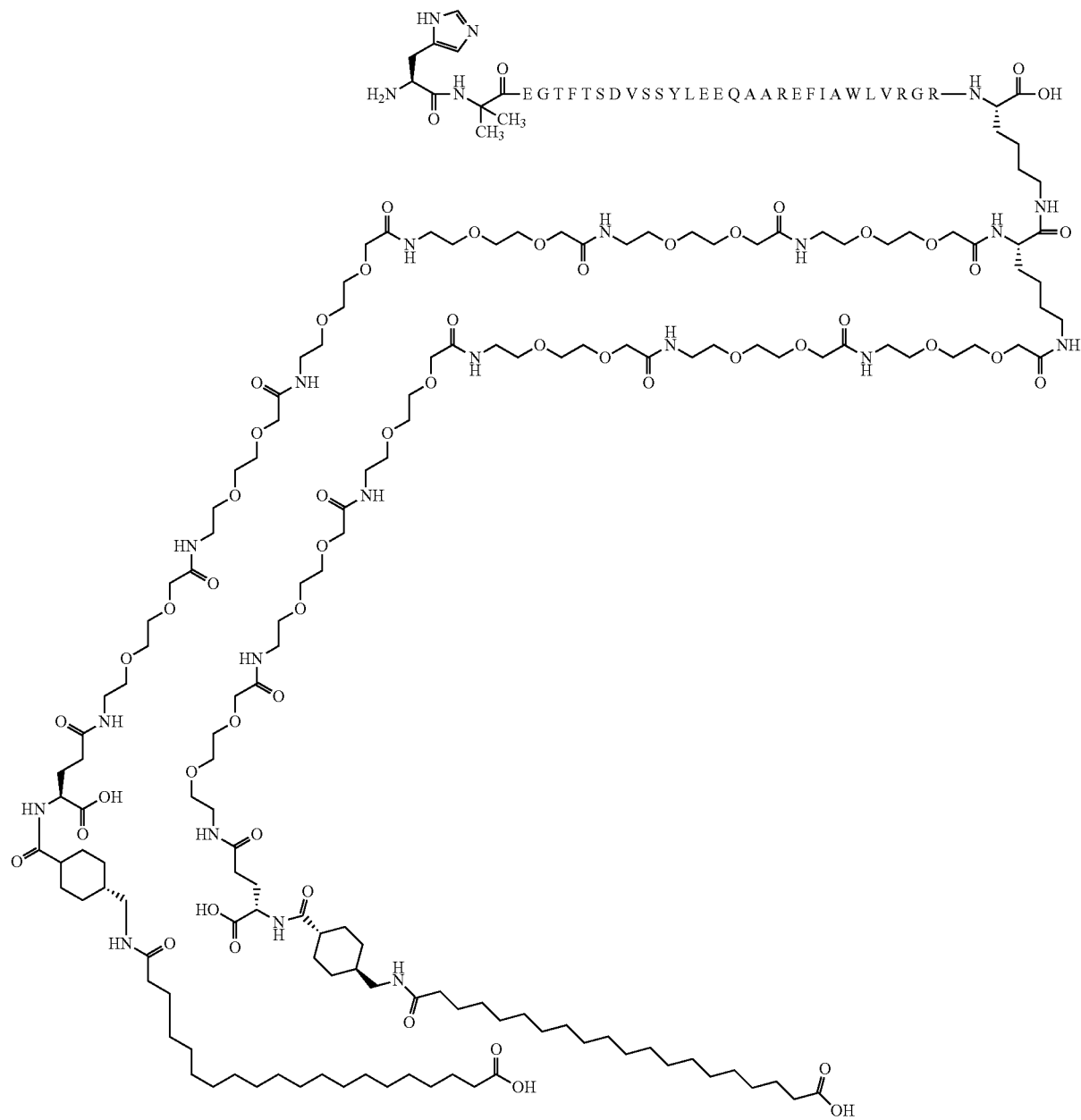

The peptide is SEQ ID NO: 6.
Synthesis method: SPPS_P; SC_P; CP_M1
UPLC02v01: Rt=10.8 min
LCMS01v01: Rt=2.7; m/4=1657; m/5=1326

Example 33

[Imp7,Aib8,Glu22,Arg26,Arg34]-GLP-1-(7-37)-peptidyl-Gly-N{Epsilon}[(2S)-2,6-bis[[2-[2-[2-[[2-[2-[2-[[2-[2-[2-[[2-[2-[2-[[(4S)-4-carboxy-4-[[4-[(19-carboxynonade-canoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]Lys

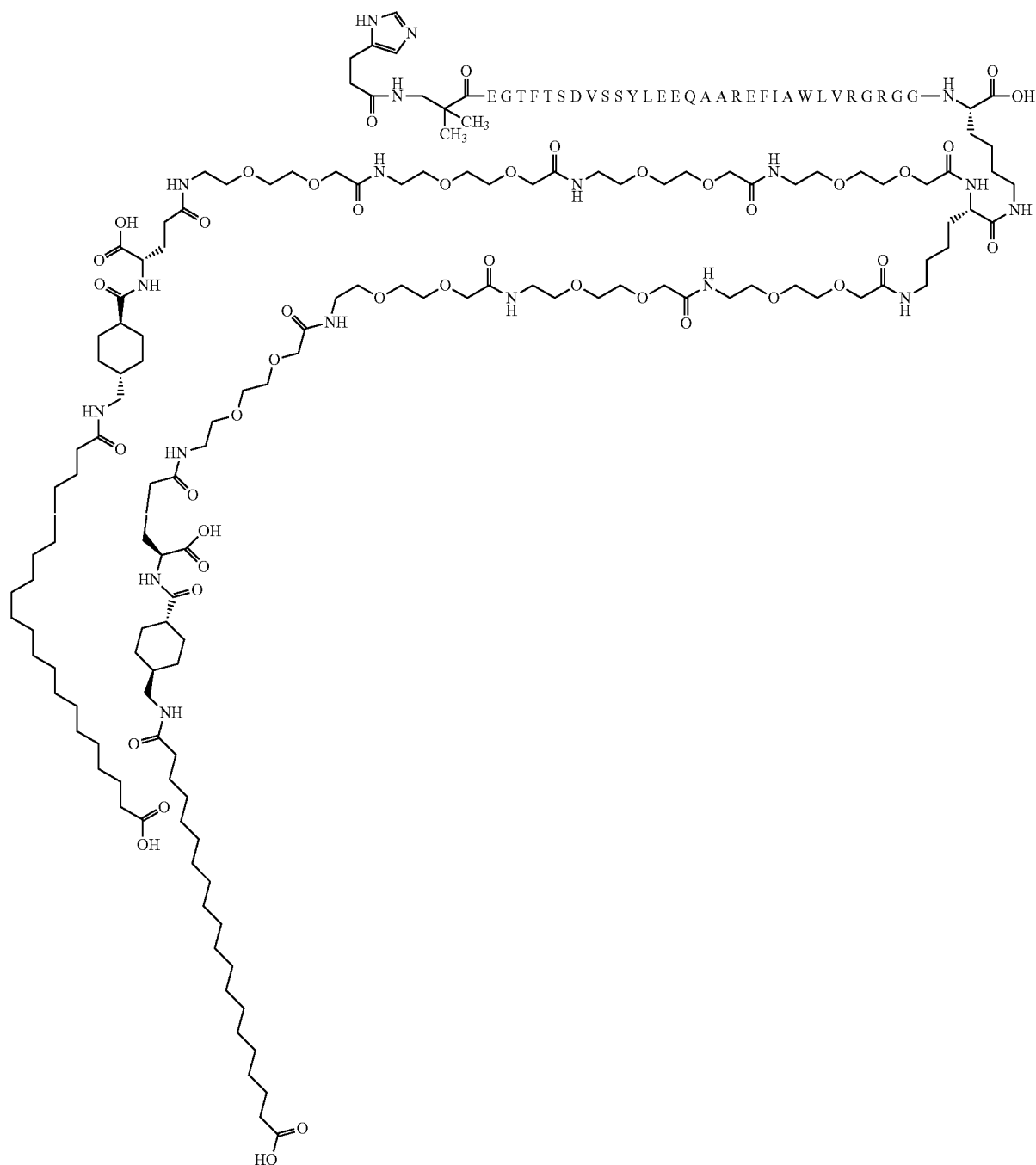

Chem. 53

The peptide is SEQ ID NO: 17.
Synthesis method: SPPS_P; SC_P; CP_M1
UPLC02v01: Rt=10.5 min
LCMS01v01: Rt=2.8; m/4=1537; m/5=1229

Example 34
N{Alpha}([Aib8,Glu22,Arg26,Arg34,Pro37]-GLP-1-(7-37)-peptidyl)-N{Epsilon}[(2S)-2,6-bis[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]Lys
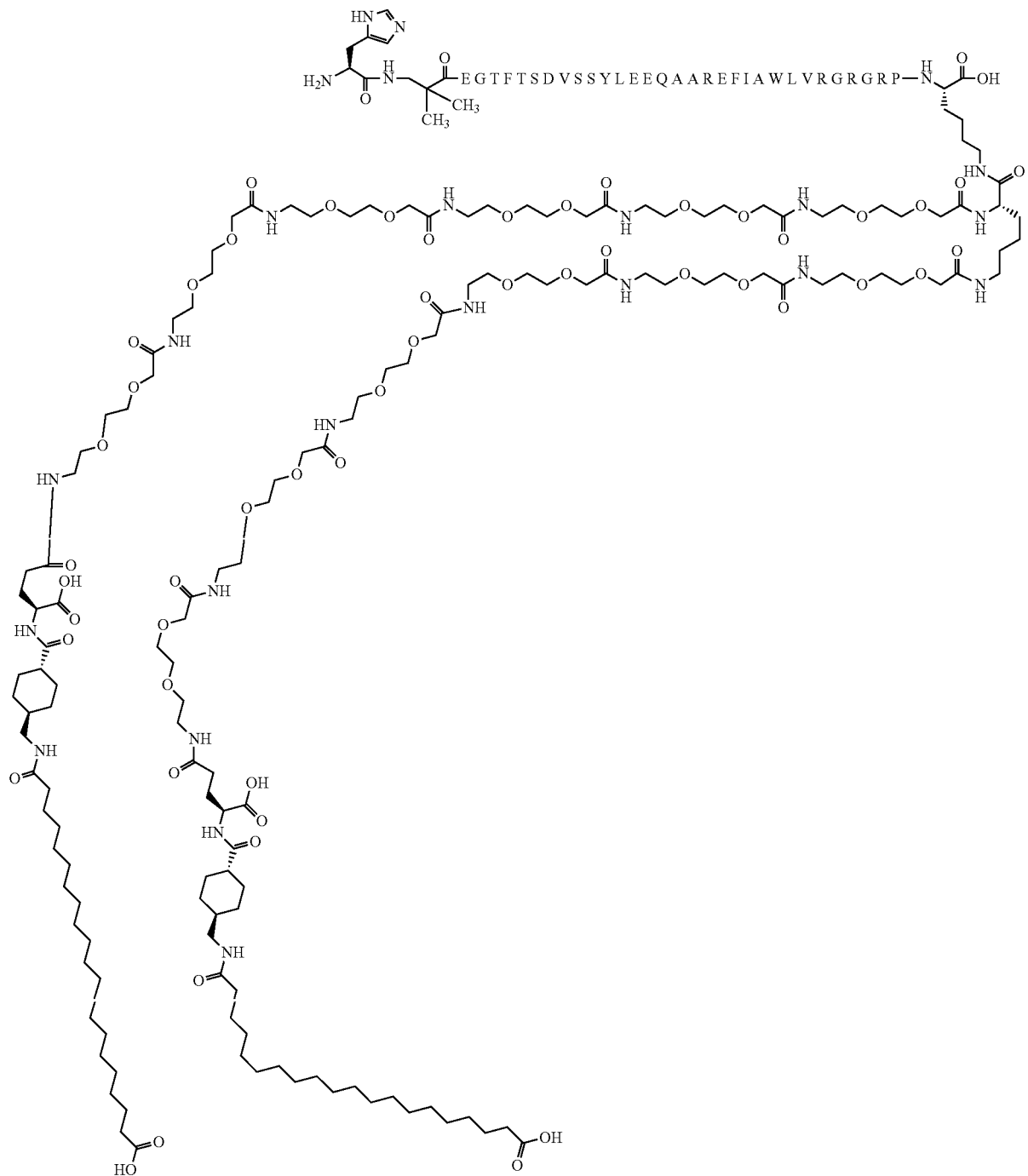
Chem. 54

The peptide is SEQ ID NO: 18.
Synthesis method: SPPS_P; SC_P; CP_M1
UPLC02v01: Rt=10.8 min
LCMS01v01: Rt=2.7; m/4=1682; m/5=1345

Comparative Example 1

N{Epsilon-37}-[2-[2-[2-[[(2S)-2,6-bis[[2-[2-[2-(dodecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide amide

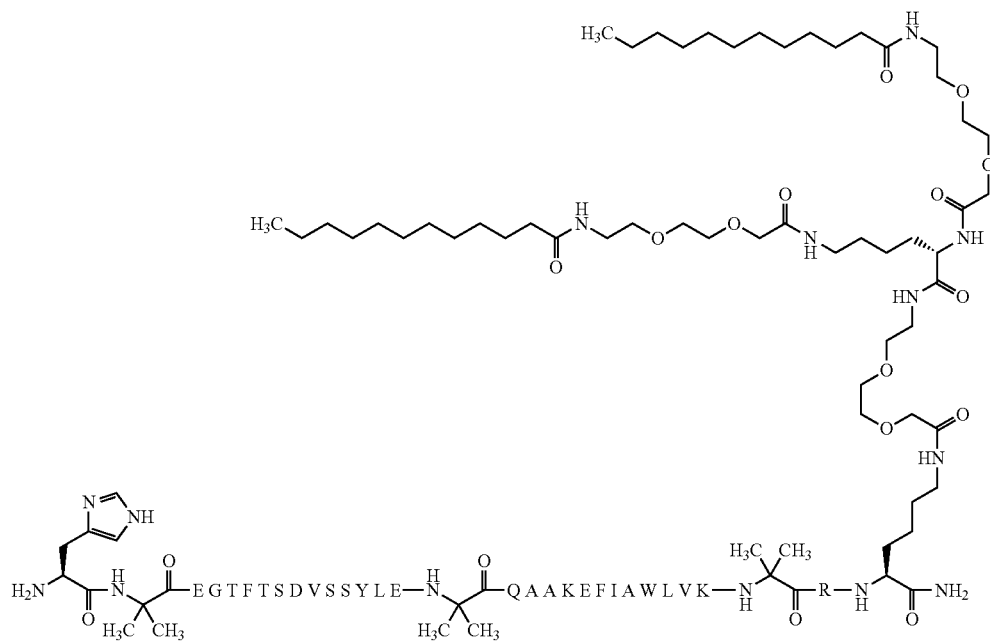

Chem. 55

The peptide is SEQ ID NO: 19.
This is the compound of Example 8 of WO2005/027978 A2.
Synthesis method: SPPS_P; SC_P; CP_M1
UPLC02v01: Rt=11.4 min
LCMS01v01: Rt=2.7; m/4=1107; m/5=886

145

Comparative Example 2

N{Epsilon-37}-[2-[2-[2-[[(2S)-2,6-bis[[2-[2-[2-(tetradecanoylamino)ethoxy]ethoxy]acetyl]amino]hexanoyl]amino]ethoxy]ethoxy]acetyl]-[Aib8,Aib22,Aib35,Lys37]-GLP-1-(7-37)-peptide amide

146

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE)

Chem. 56

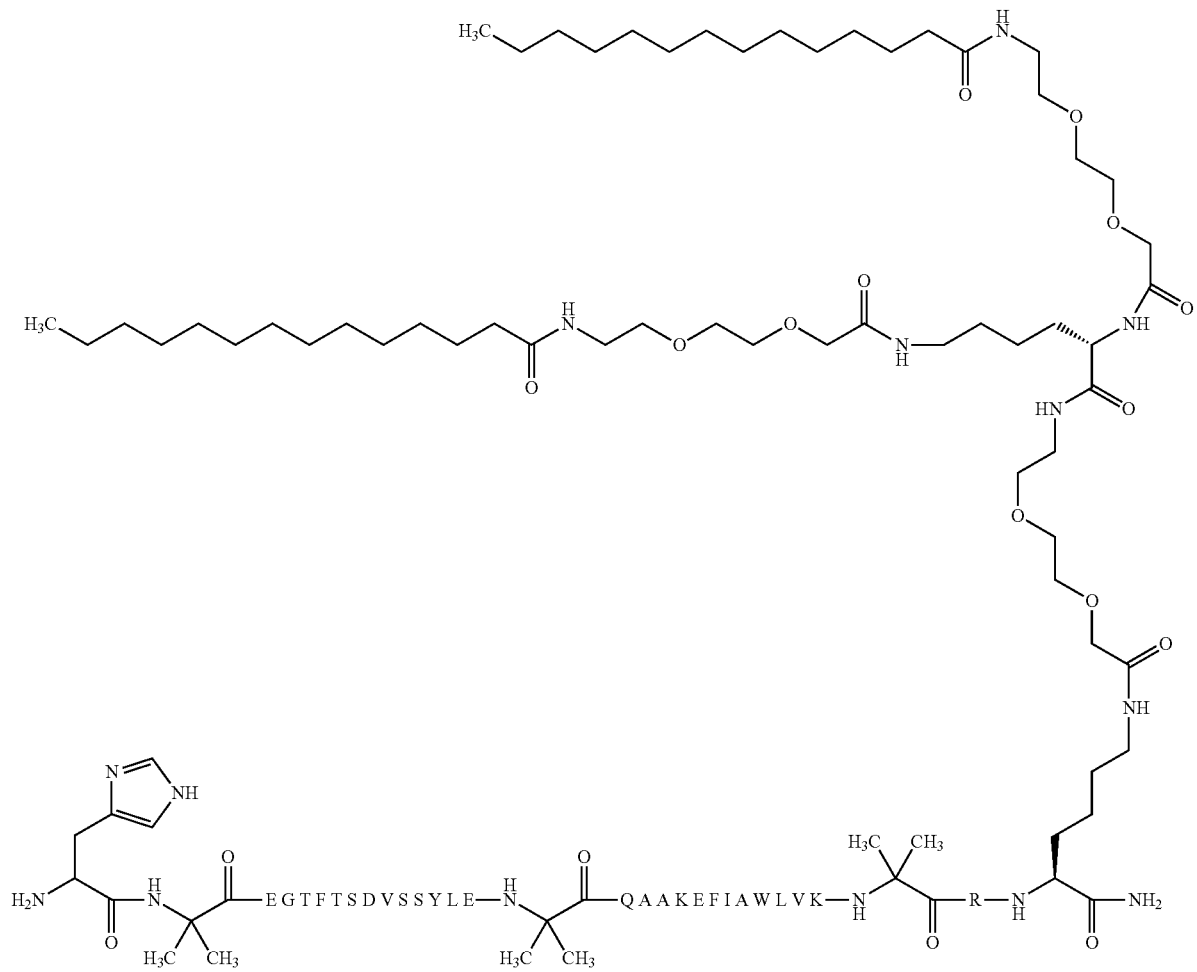

The peptide is SEQ ID NO: 19.

This is the compound of Example 9 of WO2005/027978 A2.

Synthesis method: SPPS_P; SC_P; CP_M1
UPLC02v01: Rt=12.9 min
LCMS01v01: Rt=2.9; m/3=1494; m/4=1121

Pharmacological Methods

Example 35

In Vitro Potency

The purpose of this example is to test the activity, or potency, of the GLP-1 derivatives in vitro. The in vitro potency is the measure of human GLP-1 receptor activation in a whole cell assay.

The potencies of the GLP-1 derivatives of Examples 1-32 and Comparative Examples 1 and 2 were determined as described below. Semaglutide was included for comparison.

coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in Cell Culture Medium. They were aliquoted and stored in liquid nitrogen. Before each assay an aliquot is taken up and washed twice in PBS before being suspended at the desired concentration in the assay specific buffer. For 96-well plates the suspension was made to give a final concentration of 5×10³ cells/well.

Materials

The following chemicals were used in the assay: Pluronic F-68 (10%) (Gibco 2404), human serum albumin (HSA) (Sigma A9511), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Buffers

Cell Culture Medium consisted of DMEM medium with 10% FBS (Fetal Bovine Serum; Invitrogen 16140-071), 1 mg/ml G418 (Invitrogen 15140-122), 240 nM MTX (methotrexate; Sigma M9929) and 1% pen/strep (penicillin/streptomycin; Invitrogen 15140-122).

Assay Medium consisted of DMEM w/o phenol red, 10 mM Hepes and 1× Glutamax. The Assay Buffer consisted of 2% ovalbumin and 0.2% Pluronic F-68 in Assay Medium.

Procedure

1) Cell stocks were thawed in a 37° C. water bath.
2) Cells were washed three times in PBS.
3) The cells were counted and adjusted to 5×10³ cells/50 µl (1×10⁵ cells/ml) in Assay Medium. A 50 µl aliquot of cells was transferred to each well in the assay plate.
4) Stocks of the test compounds and reference compounds were diluted to a concentration of 0.2 µM in Assay Buffer. Compounds were diluted 10-fold to give the following concentrations: $2\times10^{-7}$ M, $2\times10^{-8}$ M, $2\times10^{-9}$ M, $2\times10^{-10}$ M, $2\times10^{-11}$ M, $2\times10^{-12}$ M, $2\times10^{-13}$ M, and $2\times10^{-14}$ M.
5) A 50 µl aliquot of compound or blank was transferred from the dilution plate to the assay plate. Compounds were tested at the following final concentrations: $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M, and $1\times10^{-14}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate (reagent was light sensitive).
9) Each assay plate was covered with aluminum foil to protect it from light and shaken for 30 min at room temperature.
10) Each assay plate was read in a Packard TopCount NXT instrument.

Calculations and Results

The data from the TopCount instrument were transferred to Graph Pad Prism software. The software performs a non-linear regression (log(agonist) vs response). $EC_{50}$ values which were calculated by the software and reported in pM are shown in Table 1 below.

A minimum of two replicates was measured for each sample. The reported values are averages of the replicates.

TABLE 1

| In vitro potency | |
|---|---|
| Example no. | $EC_{50}$ (pM) |
| 1 | 94 |
| 2 | 87 |
| 3 | 51 |
| 4 | 44 |
| 5 | 23 |
| 6 | 15 |
| 7 | 70 |
| 8 | 95 |

TABLE 1-continued

| In vitro potency | |
|---|---|
| Example no. | $EC_{50}$ (pM) |
| 9 | 25 |
| 10 | 37 |
| 11 | 50 |
| 12 | 99 |
| 13 | 19 |
| 14 | 16 |
| 15 | 50 |
| 16 | 38 |
| 17 | 64 |
| 18 | 55 |
| 19 | 58 |
| 20 | 35 |
| 21 | 48 |
| 22 | 6.4 |
| 23 | 10 |
| 24 | 7.4 |
| 25 | 8.5 |
| 26 | 13 |
| 27 | 15 |
| 28 | 14 |
| 29 | 22 |
| 30 | 12 |
| 31 | 19 |
| 32 | 8.6 |
| 33 | 16 |
| 34 | 12 |
| Comparative Example 1 | 6.0 |
| Comparative Example 2 | 4.6 |
| semaglutide | 8.3 |

All compounds have a very satisfactory potency which confirms that they are all GLP-1 receptor agonists.

Example 36

GLP-1 Receptor Binding

The purpose of this example is to test the receptor binding of the GLP-1 derivatives in vitro. The receptor binding is a measure of affinity of a derivative for the human GLP-1 receptor.

Principle

The receptor binding of the GLP-1 derivatives of Examples 1-32 and Comparative Examples 1-2 to the human GLP-1 receptor was measured in a competitive binding assay. In this type of assay a labelled ligand (in this case $^{125}$I-GLP-1) is bound to the receptor. Each derivative is added in a series of concentrations to isolated membranes containing the human GLP-1 receptor and displacement of the labelled ligand is monitored. The receptor binding is reported as the concentration at which half of the labelled ligand is displaced from the receptor, the $IC_{50}$ value. Semaglutide was included as comparative compound. In order to test the binding of the derivatives to albumin, the assay is performed in a low concentration of serum albumin (max. 0.001% final assay concentration as well as in the presence of a considerably higher concentration of serum albumin (2.0% final assay concentration). An increase of the $IC_{50}$ value in the presence of serum albumin indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36)$NH_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM $MgCl_2$, 0.005% Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418.

To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005%) 50 µl of the assay buffer was added to each well of an assay plate. Assay continued with step 3.
2. For the receptor binding assay in the presence of high HSA (2%) 50 µl of the 8% albumin stock was added to each well of an assay plate. Assay continued with step 3.
3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 pM solution of [$^{125}$I]-GLP-1]-(7-36)$NH_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

The data from the TopCount instrument were transferred to Graph Pad Prism software. The software averaged the values for the replicates and performed a non-linear regression. $IC_{50}$ values were calculated by the software and reported in nM.

Results

The following results were obtained:

TABLE 2

| GLP-1 receptor binding | | |
|---|---|---|
| Example no. | Low HSA $IC_{50}$ (nM) | High HSA $IC_{50}$ (nM) |
| 1 | 1.64 | 175 |
| 2 | 1.93 | 59 |
| 3 | 0.74 | 25 |
| 4 | 0.61 | 83 |
| 5 | 1.11 | 103 |
| 6 | 0.65 | 64 |
| 7 | 0.90 | 78 |
| 8 | 1.86 | 132 |
| 9 | 0.45 | 64 |
| 10 | 0.62 | 58 |
| 11 | 1.06 | 117 |
| 12 | 0.99 | 28 |
| 13 | 0.34 | 110 |
| 14 | 0.25 | 101 |
| 15 | 0.66 | 99 |
| 16 | 0.41 | 43 |
| 17 | 1.72 | 138 |
| 18 | 0.76 | 68 |
| 19 | 0.53 | 220 |
| 20 | 0.48 | 149 |
| 21 | 0.97 | 4.9 |
| 22 | 0.60 | 39 |
| 23 | 0.75 | 46 |
| 24 | 0.73 | 52 |
| 25 | 0.86 | 38 |
| 26 | 1.7 | 27 |
| 27 | 2.9 | 50 |
| 28 | 2.9 | 68 |
| 29 | 4.8 | 51 |
| 30 | 3.2 | 63 |
| 31 | 3.1 | 85 |
| 32 | 1.2 | 84 |
| 33 | 0.91 | 54 |
| 34 | 0.57 | 84 |
| Comparative Example 1 | 0.39 | 0.14 |
| Comparative Example 2 | 1.9 | 0.68 |
| semaglutide | 0.56 | 326 |

All compounds show a very good binding to the GLP-1 receptor in the absence as well as in the presence of albumin.

Example 37

Pharmacokinetic Study in Minipigs

The purpose of this study is to determine the protraction in vivo of the GLP-1 derivatives after i.v. administration to minipigs, i.e. the prolongation of their time in the body and thereby their time of action. This is done in a pharmacokinetic (PK) study, where the terminal half-life of the derivative in question is determined. By terminal half-life is meant the time it takes to halve a certain plasma concentration in the terminal elimination phase.

The derivatives of Examples 1-6 were dosed 2 nmol/kg, the derivative of Examples 7 and 24, as well as the derivatives of Comparative Examples 1 and 2 were dosed 5 nmol/kg, and the derivatives of Examples 8-10, 12, 14-16, 18, and 21 were dosed 15 nmol/kg. Semaglutide was included for comparison (1.5 nmol/kg).

Male Göttingen minipigs were obtained from Ellegaard Göttingen Minipigs (Dalmose, Denmark) approximately 7-14 months of age and weighing approximately 16-35 kg were used in the studies. The minipigs were housed either individually (pigs with permanent catheters) or in a group and fed restrictedly once or twice daily with SDS minipig diet (Special Diets Services, Essex, UK).

After at least 2 weeks of acclimatisation two permanent central venous catheters were implanted in vena cava caudalis or cranialis in each animal. The animals were allowed 1 week recovery after the surgery, and were then used for repeated pharmacokinetic studies with a suitable wash-out period between successive GLP-1 derivative dosings.

The GLP-1 derivatives of Examples 1-10, 12, 14-16, and 18 were dissolved in 50 mM sodium phosphate, 145 mM sodium chloride, 0.05% tween 80, pH 7.4, the GLP-1 derivatives of Examples 21 and 24 were dissolved in 50 mM sodium phosphate, 70 mM sodium chloride, 0.05% polysorbate 80, pH 7.4, and the GLP-1 derivatives of Comparative Examples 1 and 2 were dissolved in 2 mM sodium acetate, 250 mM glycerol and 0.025% polysorbate 20, pH 4.0, all to a concentration of usually from 20-60 nmol/ml.

Intravenous injections (the volume corresponding to for example 0.050-0.125 ml/kg) of the compounds were given through one catheter or through the venflon, and blood was sampled at predefined time points for up till 25 days post dosing (preferably through the other catheter or by venipuncture). Blood samples (for example 0.8 ml) were collected in EDTA buffer (8 mM) and then centrifuged at 4° C. and 1942 G for 10 minutes.

Plasma was pipetted into Micronic tubes on dry ice, and kept at −20° C. until analysed for plasma concentration of the respective GLP-1 compound using LOCI. Individual plasma concentration-time profiles were analyzed by a non-compartmental pharmacokinetic method in Phoenix v. 6.2 (Pharsight Inc., Mountain View, Calif., USA), or other relevant software for PK analysis, and the resulting terminal half-lives (harmonic mean) determined.

Results

TABLE 3

Pharmacokinetic study in minipigs (i.v.)

| Example no. | Terminal half-live (h) |
|---|---|
| 1 | 138 |
| 2 | 133 |
| 3 | 122 |
| 4 | 164 |
| 5 | 141 |
| 6 | 128 |
| 7 | 116 |
| 8 | 139 |
| 9 | 131 |
| 10 | 141 |
| 12 | 169 |
| 14 | 133 |
| 15 | 184 |
| 16 | 131 |
| 18 | 140 |
| 21 | 140 |
| 24 | 179 |
| Comparative Example 1 | 3 |
| Comparative Example 2 | 3 |
| semaglutide | 55 |

The tested derivatives of the invention have very long terminal half-lives (at least twice that of semaglutide, and at least forty times that of the comparative example compounds).

Example 38

Pharmacodynamic Study in Db/Db Mice

The purpose of the study is to verify the acute effect of the GLP-1 derivatives on blood glucose (BG) and body weight (BW) in a diabetic setting.

The GLP-1 derivatives of Examples 1-10, 12, 14-16, 18, 21-23, and 25 were tested in a single-dose study in an obese, diabetic mouse model (db/db mice) as described in the following. The derivatives were tested at a dose of 10 nmol/kg (Examples 21-23, 25), 30 nmol/kg (Examples 5, 9, 12, 14-16, 18), and 100 nmol/kg (Examples 1-4, 6-8, 10).

Six db/db mice per compound to be tested (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. The mice were given free access to standard chow (e.g. Altromin 1324, Brogaarden, Gentofte, Denmark) and tap water and kept at 24° C. After 1-2 weeks of acclimatisation, the basal blood glucose was assessed twice on two consecutive days (i.e. at 9 am). The mice were allocated to treatment groups based on matching blood glucose levels and body weights. The mice were used in experiments with a duration of 120 hours, and were re-used for up to 2 times. After the last experiment the mice were euthanised.

The animals were grouped to receive treatment as follows: Vehicle, s.c., or GLP-1 derivative, s.c., where vehicle was 50 mM sodium phosphate, 70 mM sodium chloride, 0.05% polysorbate 80, pH 7.4.

The GLP-1 derivative was dissolved in the vehicle, to a dosing concentration of 1.7-17 nmol/ml dependent on the respective dose. Animals were dosed once, at the start of the experiment, s.c. with a dose-volume of 6 ml/kg (i.e. 300 μl per 50 g mouse).

On the day of dosing, blood glucose was assessed at time −½ h (8.30 am), the mice were weighed after this. The GLP-1 derivative was dosed at approximately 9 am (time 0). On the day of dosing, blood glucose was assessed at times 1, 2, 4 and 8 h (10 am, 11 am, 1 pm and 5 pm) after dosing.

On the following days, the blood glucose was assessed at time 24 h, 48 h, 72 h, and 96 h. On each day, the mice were weighed following blood glucose sampling.

The mice were weighed individually on a digital weighing scale.

Samples for the measurement of blood glucose were obtained from the tail tip capillary of conscious mice. Blood, 10 μl, was collected into heparinised capillaries and transferred to 500 μl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

The data are presented as percent change in blood glucose or body weight measured at the 48 h and the 96 h time points. For example, the percent change in blood glucose level at 48 h for each individual is calculated as follows: [[(blood glucose level at 48 h)−(basal blood glucose level)]/(basal blood glucose level)]×100%], where basal blood glucose level refers to the level before the administration of any treatment—and vice versa for the body weight change. A negative value refers to a % reduction.

The following results were obtained (averages of all individual determinations corresponding to the respective treatment):

TABLE 4

Effect on blood glucose and body weight in db/db mice

| Example no. | % change in blood glucose | | % change in body weight | |
|---|---|---|---|---|
| | 48 h | 96 h | 48 h | 96 h |
| 1 | −53 | −30 | −7 | −5 |
| 2 | −64 | −50 | −7 | −6 |
| 3 | −62 | −41 | −7 | −5 |
| 4 | −61 | −42 | −6 | −5 |
| 5 | −22 | −12 | −2 | −3 |
| 6 | −59 | −33 | −7 | −5 |
| 7 | −61 | −46 | −7 | −6 |
| 8 | −67 | −42 | −7 | −5 |
| 9 | −55 | −25 | −7 | −5 |
| 10 | −64 | −50 | −7 | −6 |
| 12 | −36 | −11 | −4 | −2 |
| 14 | −39 | −20 | −3 | −3 |
| 15 | −54 | −21 | −5 | −4 |
| 16 | −45 | −34 | −5 | −4 |
| 18 | −36 | −14 | −4 | −3 |
| 21 | −20 | −4 | −4 | −2 |
| 22 | −50 | −29 | −4 | −1 |
| 23 | −47 | −7 | −5 | −2 |
| 25 | −22 | −1 | −4 | −3 |

All derivatives tested showed effect in vivo by decreasing BG as well as BW after 48 h as well as after 96 h.

Example 39

Pharmacodynamic Study in LYD Pig

The purpose of this experiment is to investigate the effect of GLP-1 derivatives on food intake in pigs. This is done in a pharmacodynamic (PD) study as described below, in which food intake is measured from 1 to 4 days after administration of a single dose of the GLP-1 derivative, as compared to a vehicle-treated control group.

Female Landrace Yorkshire Duroc (LYD) pigs, approximately 3 months of age, weighing approximately 30-35 kg are used (n=3-4 per group). The animals are housed in a group for approximately 1 week during acclimatisation to the animal facilities. During the experimental period the animals are placed in individual pens at least 2 days before dosing and during the entire experiment for measurement of individual food intake. The animals are fed ad libitum with pig food (Svinefoder, Danish Top, or HRC Sow and Weaner Diet) at all times both during the acclimatisation and the experimental period. Food intake is monitored either on line by logging the weight of food every 15 minutes, or manually. The weight of food is recorded daily for each animal (24 h periods) from day −2 to day 6 (120 hour) after dose, administration inclusive.

The GLP-1 derivatives are first dissolved in a phosphate buffer (50 mM phosphate, 0.05% tween 80, pH 8; or 50 mM phosphate, 145 mM sodium chloride, 0.05% tween 80, pH 7.4) at the desired concentration (such as 12, 40, 120, 400 or 1200 nmol/ml corresponding to doses of 10, 15, or 30 nmol/kg). The phosphate buffer serves as vehicle. Animals are dosed with a single subcutaneous dose of the GLP-1 derivative or vehicle (usual dose volume 0.025 ml/kg) on the morning of day 1, and food intake is measured for 1-4 days after dosing. On the last day of each study, 1-4 days after dosing, a blood sample for measurement of plasma exposure of the GLP-1 derivative is taken from the jugular/anterior vena cava. The animals are re-used for three experiments. Plasma content of the GLP-1 derivatives is analysed using LOCI.

Food intake is calculated as mean 24 h food intake in 24 h intervals (0-24 h, 24-48 h, 48-72 h, and 72-96 h) and may, e.g., be indicated as percentage of the food intake of the vehicle group in the same time interval.

Statistical comparisons of the food intake in the 24 hour intervals in the vehicle vs. GLP-1 derivative group are done using two-way-ANOVA repeated measures, followed by Bonferroni post-test.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of a GLP-1 peptide, wherein the GLP-1 peptide is of Formula I:

Xaa$_7$-Xaa$_8$-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$, wherein Xaa$_7$ is L-histidine, (S)-2-Hydroxy-3-(1H-imidazol-4-yl)-propionic acid, D-histidine, desamino-histidine, homo-histidine, N$^\alpha$-acetyl-histidine, N$^\alpha$-formyl-histidine, α-methyl-histidine, 3-pyridylalanine, 2-pyridylalanine, or 4-pyridylalanine;

Xaa$_8$ is Ala, Gly, Ser, Aib, (1-aminocyclopropyl) carboxylic acid, or(1-aminocyclobutyl) carboxylic acid;

Xaa$_{12}$ is Phe or Leu;
Xaa$_{16}$ is Val or Leu;
Xaa$_{18}$ is Ser, Val, Lys, Arg, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val, Lys, or Arg;
Xaa$_{34}$ is Arg, Lys, His, Asn, or Gln;
Xaa$_{35}$ is Gly or Ala;
Xaa$_{36}$ is Arg or Gly;
Xaa$_{37}$ is Gly, Pro, or Lys;
Xaa$_{38}$ is Ser, Gly, Ala, Glu, Pro, Lys, or absent;
Xaa$_{39}$ is Ser, Gly, Ala, Glu, Pro, Lys, or absent;
Xaa$_{40}$ is Ser, Gly, Ala, Glu, Pro, Lys, or absent;
Xaa$_{41}$ is Ser, Gly, Ala, Glu, Pro, Lys, or absent;
Xaa$_{42}$ is Ser, Gly, Ala, Glu, Pro, Lys, or absent; and
Xaa$_{43}$ is Ser, Gly, Ala, Glu, Pro, Lys, or absent;
wherein
i) if Xaa$_{42}$ is absent, then Xaa$_{43}$ is also absent;
ii) if Xaa$_{41}$ is absent, then Xaa$_{42}$ and Xaa$_{43}$ is also absent;
iii) if Xaa$_{40}$ is absent, then Xaa$_{41}$, Xaa$_{42}$, and Xaa$_{43}$ are also absent;
iv) if Xaa$_{39}$ is absent, then Xaa$_{40}$, Xaa$_{41}$, Xaa$_{42}$, and Xaa$_{43}$ are also absent; and/or
v) if Xaa$_{38}$ is absent, then Xaa$_{39}$, Xaa$_{40}$, Xaa$_{41}$, Xaa$_{42}$, and Xaa$_{43}$ are also absent;
wherein the GLP-1 peptide comprises a Lys residue at a position corresponding to position 27, 37, 38, 39, 40, 41, 42, or 43 of GLP-1(7-37) (SEQ ID NO: 1);
wherein the derivative comprises
a first and a second protracting moiety selected from Chem. 1 and Chem. 1a:

HOOC—(CH$_2$)$_{18}$—CO—*, and      Chem. 1:

HOOC—(CH$_2$)$_{20}$—CO—*;      Chem. 1a:

a branched linker of formula Chem. 2:

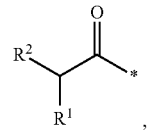

Chem. 2 wherein
R$^1$ is —(CH$_2$)$_q$—NH—*, wherein q is an integer in the range of 0-5,
R$^2$ is —(CH$_2$)$_w$—NH—*, wherein w is an integer in the range of 0-5,
with the provisos that when w is 0 q is an integer in the range of 1-5, and when q is 0 w is an integer in the range of 1-5; and
a first and a second further linker, each comprising an element_1 of formula Chem. 3:

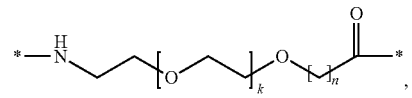

Chem. 3 wherein k is an integer in the range of 1-15, and n is an integer in the range of 1-5;
wherein
the first protracting moiety is attached at its *—CO end to a first *—NH end of the branched linker, via the first further linker,
the second protracting moiety is attached at its *—CO end to a second *—NH end of the branched linker, via the second further linker; and
the branched linker is attached at its *—CO end to the epsilon amino group of the Lys residue at a position corresponding to position 27,37,38,40,41,42, or 43 of GLP-1(7-37) (SEQ ID NO: 1) of the GLP-1 peptide;
or a pharmaceutically acceptable salt, amide, or ester thereof.

2. The derivative of claim 1, wherein q=4 and w=0.

3. The derivative of claim 1, wherein the first further linker and the second further linker each comprises an element _2 of formula Chem. 4:

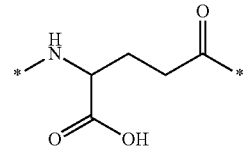

Chem. 4

4. The derivative of claim 1, wherein Xaa$_8$ is Aib.

5. The derivative of claim 1, wherein Xaa$_7$ is L-histidine, (S)-2-Hydroxy-3-(1H-imidazol-4-yl)-propionic acid, D-histidine, desamino-histidine, N$^\alpha$-acetyl-histidine, N$^\alpha$-formyl-histidine, or α-methyl-histidine; Xaa$_8$ is Ala, Gly, Ser, Aib, (1-aminocyclopropyl) carboxylic acid, or(1-aminocyclobutyl) carboxylic acid; Xaa$_{12}$ is Phe; Xaa$_{16}$ is Val or Leu; Xaa$_{18}$ is Ser, Lys, or Arg; Xaa$_{19}$ is Tyr or Gln; Xaa$_{20}$ is Leu or Met; Xaa$_{22}$ is Gly or Glu; Xaa$_{23}$ is Gln, Glu, or Arg; Xaa$_{25}$ is Ala or Val; Xaa$_{26}$ is Arg or Lys; Xaa$_{27}$ is Glu, Lys, or Leu; Xaa$_{30}$ is Ala or Glu; Xaa$_{31}$ is Trp or His; Xaa$_{33}$ is Val, Lys, or Arg; Xaa$_{34}$ is Arg, Lys, or Asn; Xaa$_{35}$ is Gly; Xaa$_{36}$ is Arg or Gly; Xaa$_{37}$ is Gly, Pro, or Lys; Xaa$_{38}$ is Ser, Gly, Ala, Glu, Pro, Lys, or absent; Xaa$_{39}$ is Ser, Gly, Ala, Glu, Pro, Lys, or absent; Xaa$_{40}$ is Ser, Gly, Ala, Glu, Pro, Lys, or absent; Xaa$_{41}$ is Ser, Gly, Ala, Glu, Pro, Lys, or absent; Xaa$_{42}$ is Gly, Ala, Glu, Pro, Lys, or absent; and Xaa$_{43}$ is Lys or absent.

6. The derivative of claim 1, wherein the GLP-1 peptide has a maximum of 12 amino acid changes, when compared with GLP-1(7-37) (SEQ ID NO: 1).

7. The derivative of claim 1, wherein the first further linker and the second further linker each comprises an element _3 of formula Chem. 5:

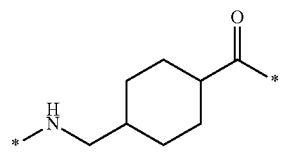

Chem. 5

8. The derivative of claim 1, wherein the first further linker and the second further linker each comprises an element _4 of formula Chem. 6:

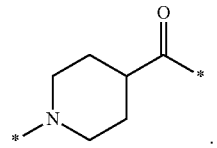

Chem. 6

9. A GLP-1 derivative selected from the following: Chem. 21

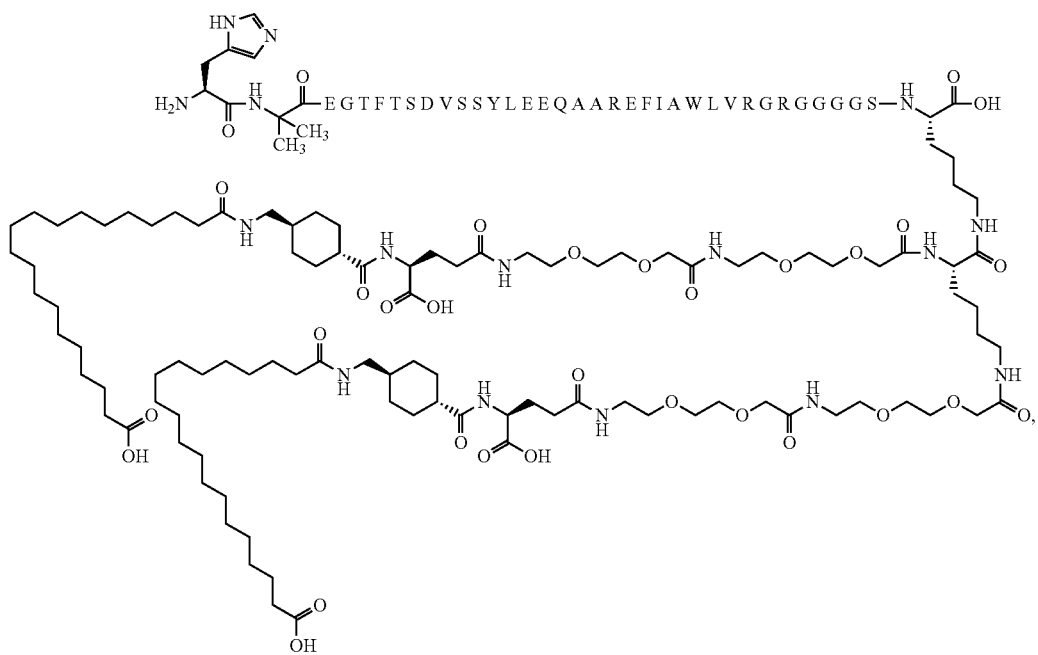

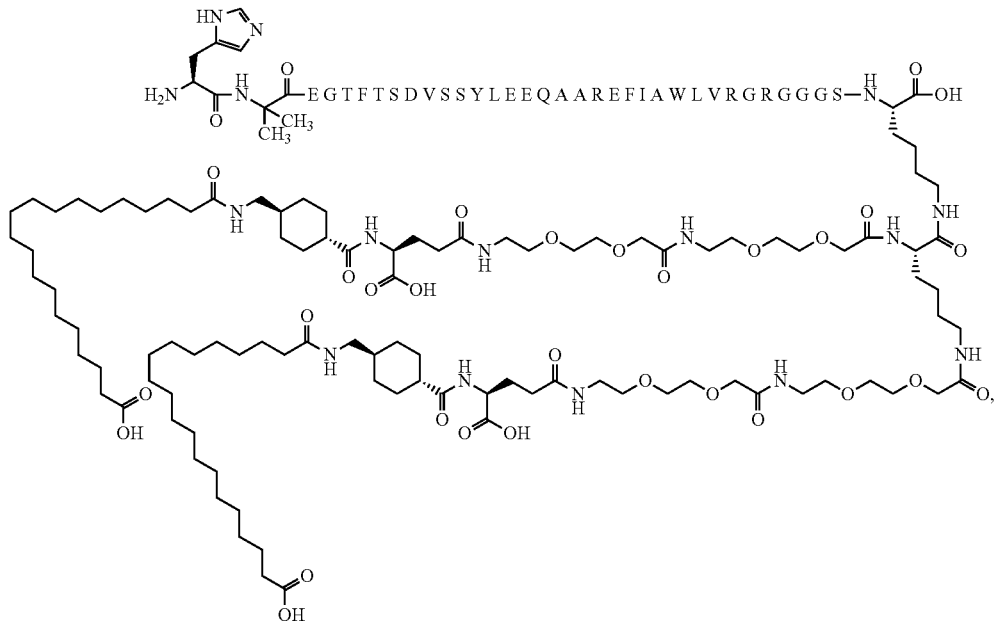
Chem. 22
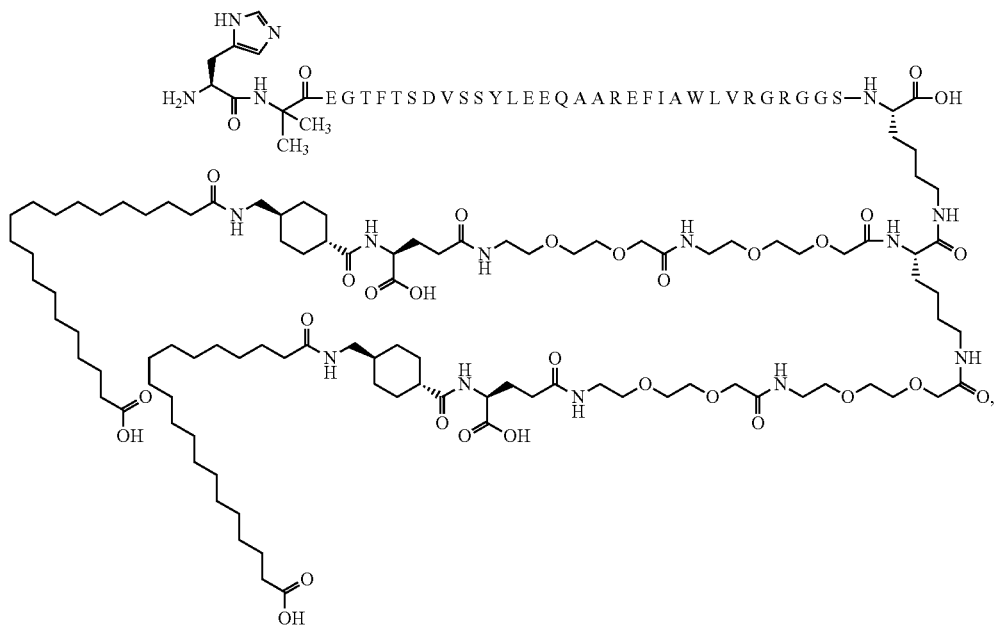
Chem. 23

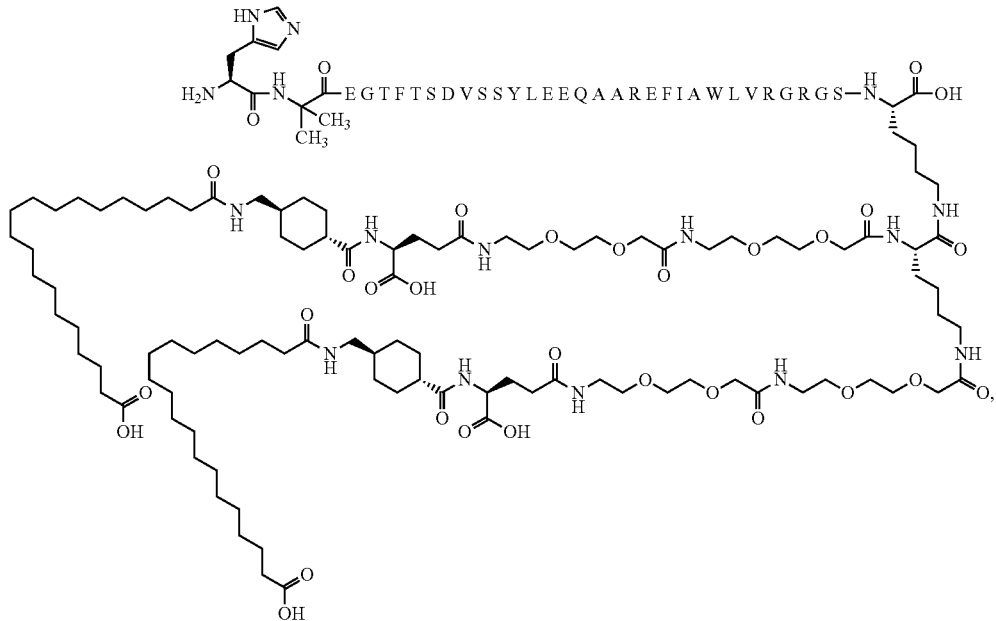
Chem. 24
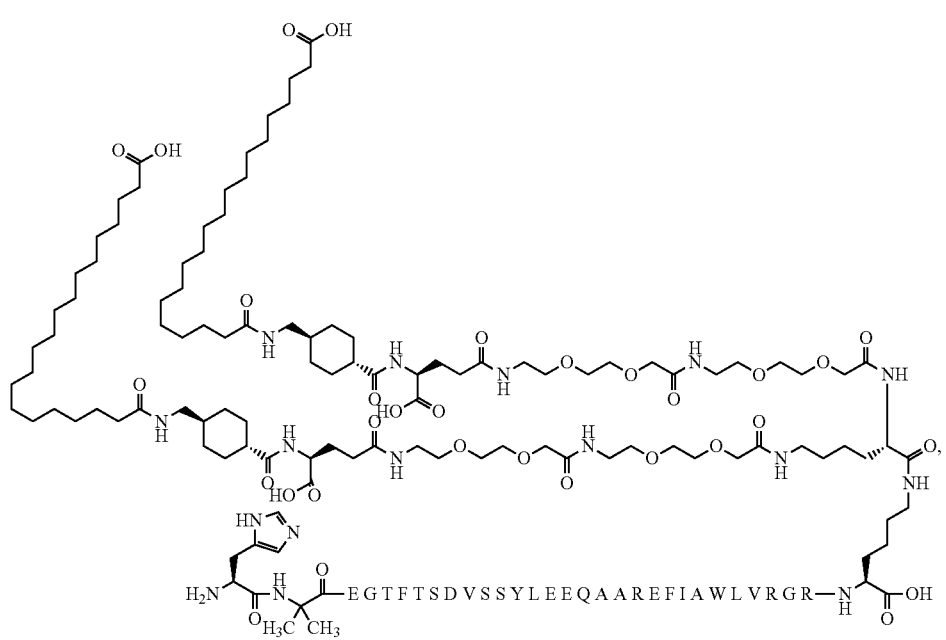
Chem. 25

Chem. 26
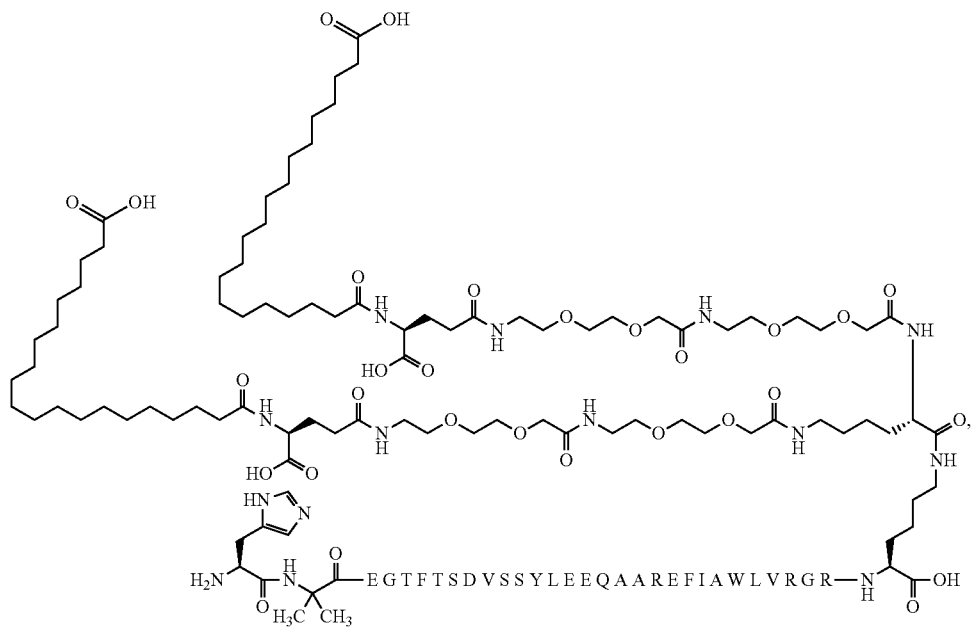
Chem. 27
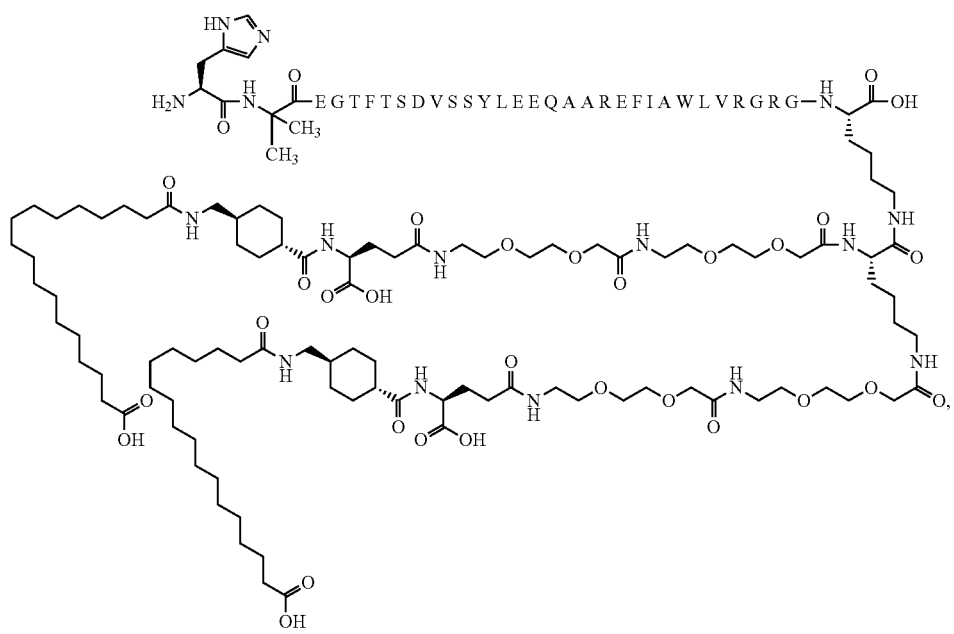

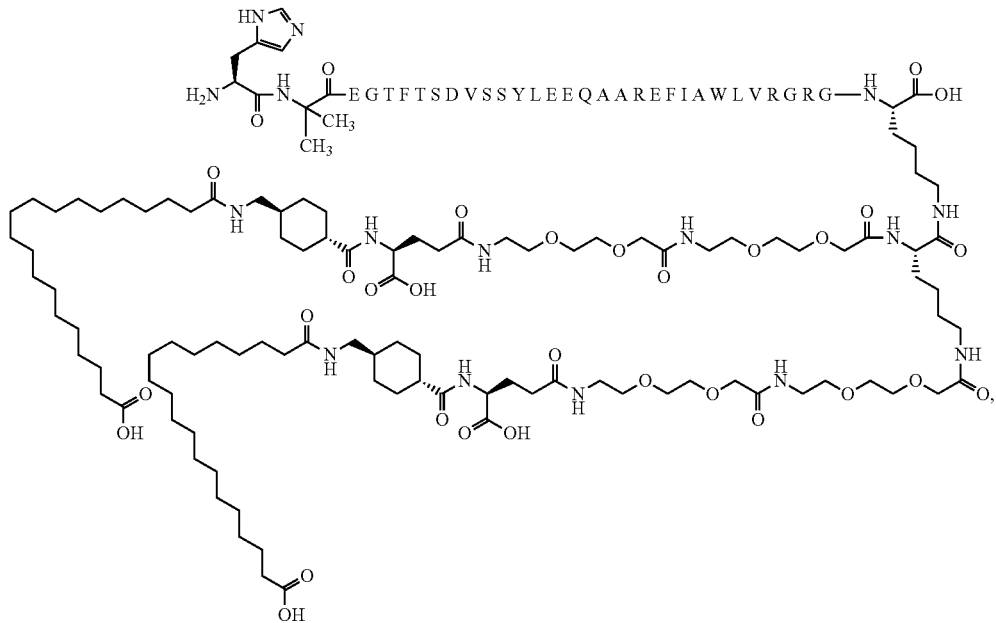
Chem. 28
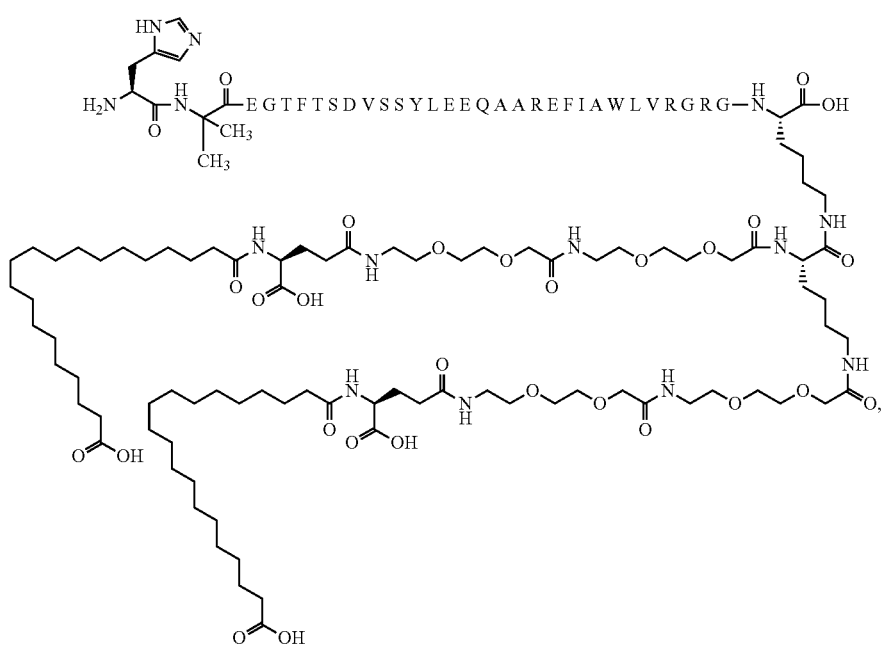
Chem. 29

Chem. 30
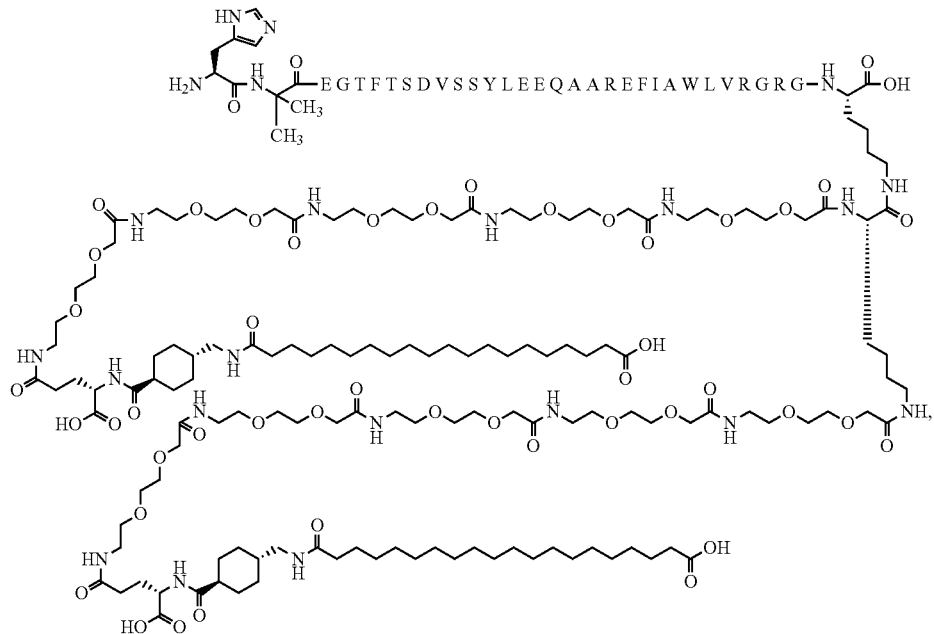
Chem. 31
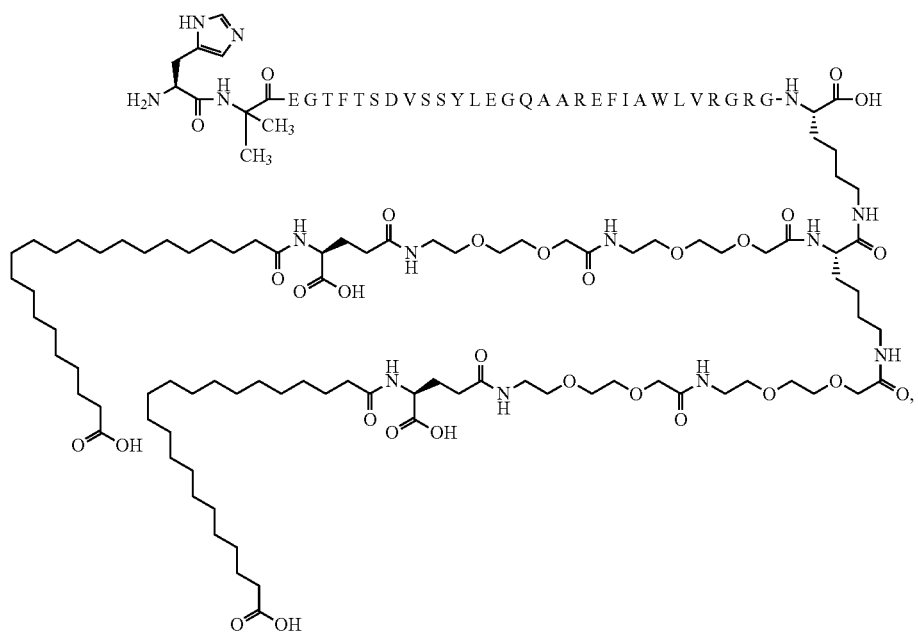

Chem. 32
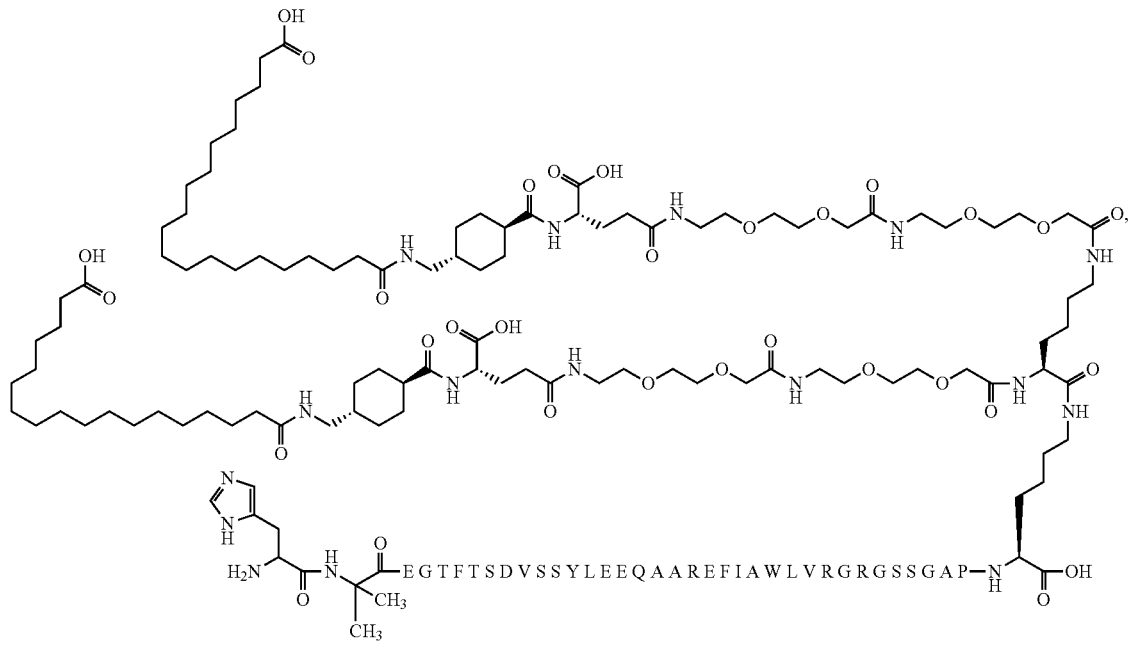
Chem. 33
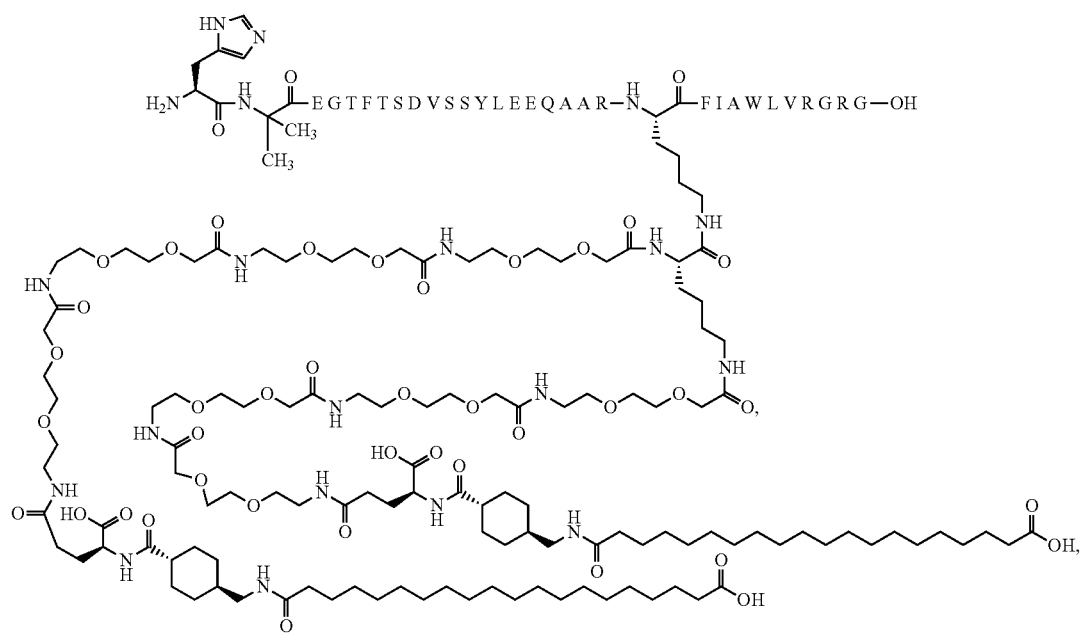

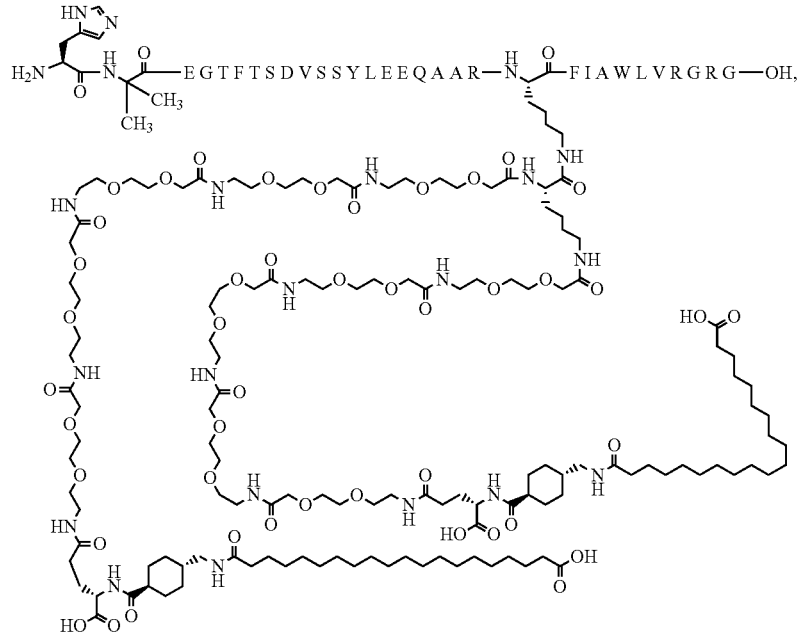
Chem. 34
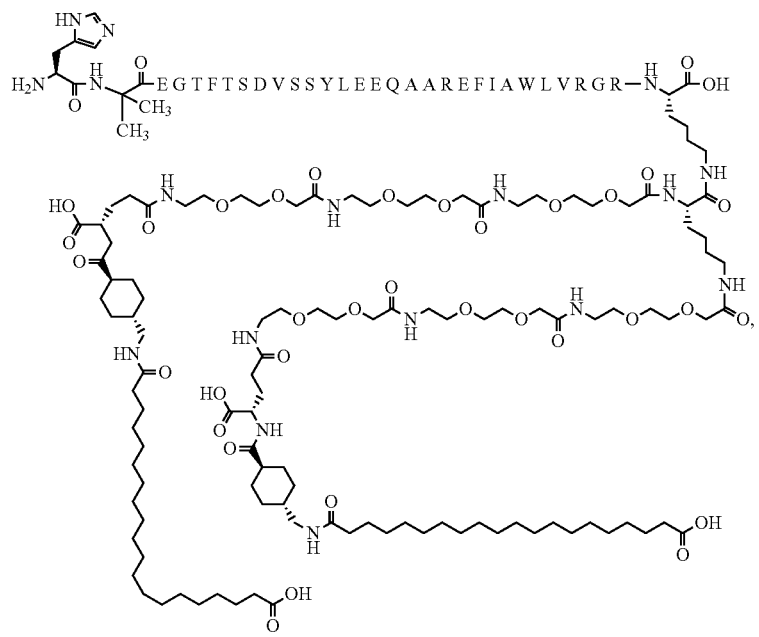
Chem. 35

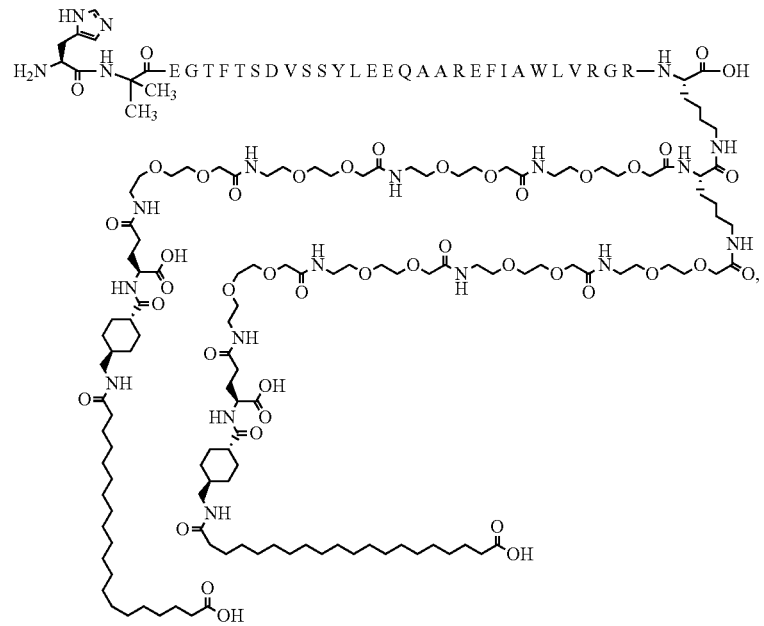
Chem. 36
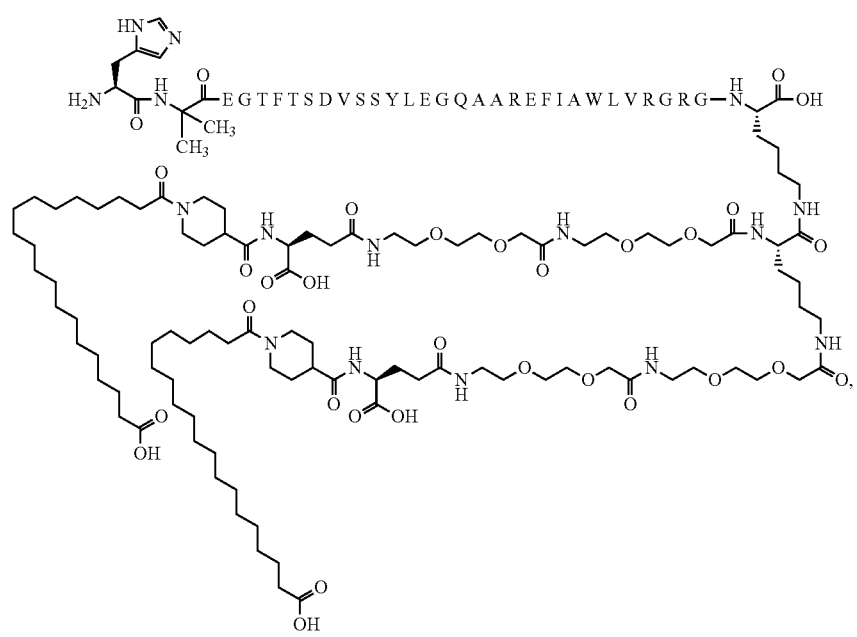
Chem. 37

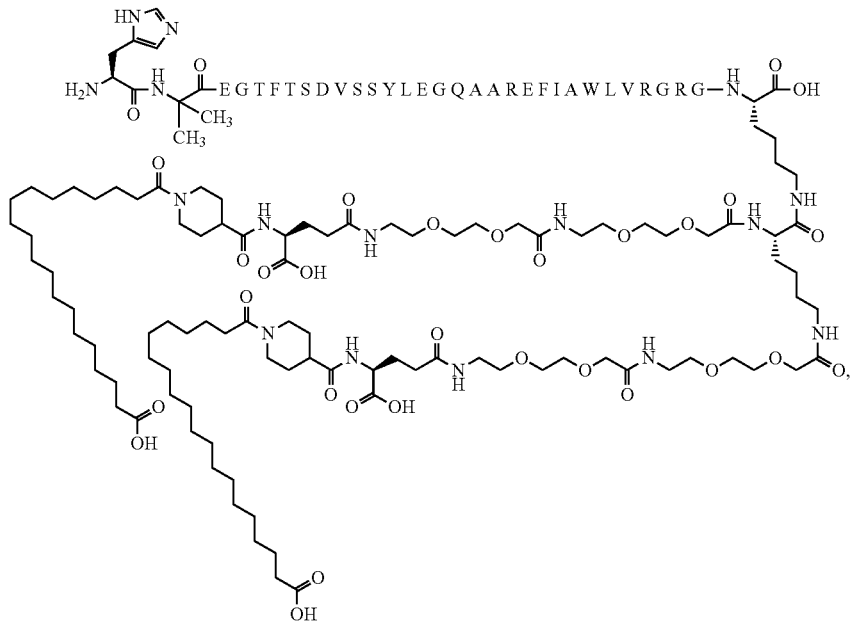
Chem. 38
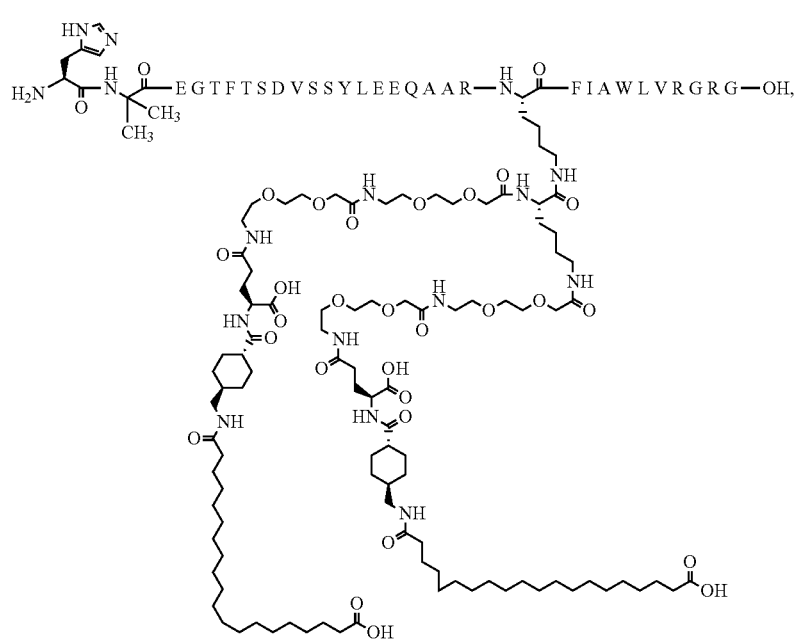
Chem. 39

-continued
Chem. 40
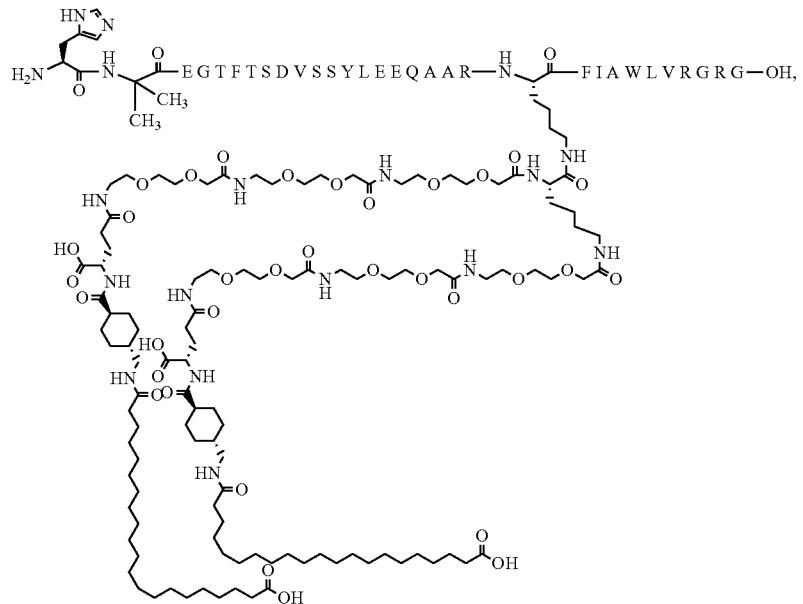
Chem. 41
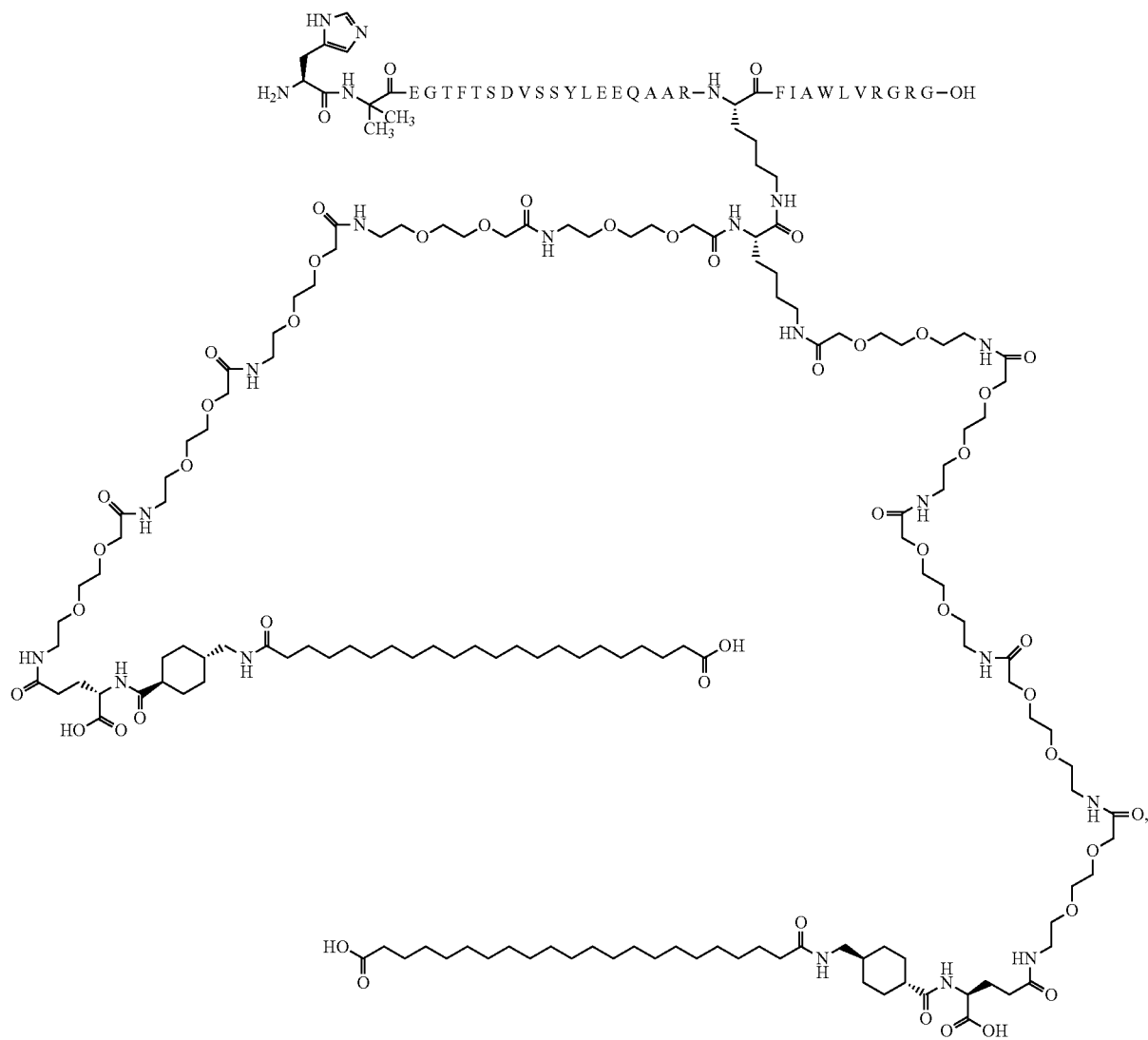

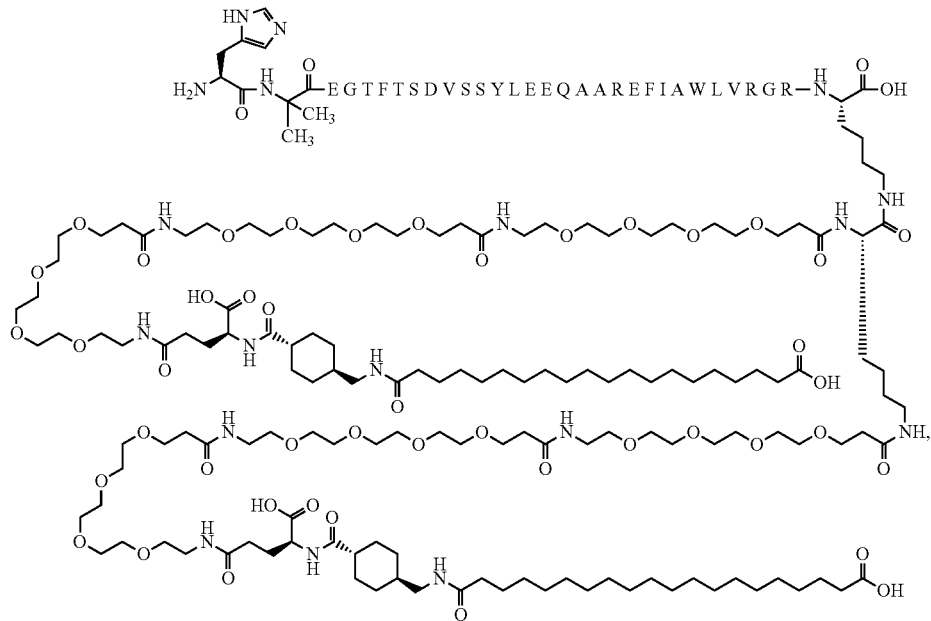
Chem. 42
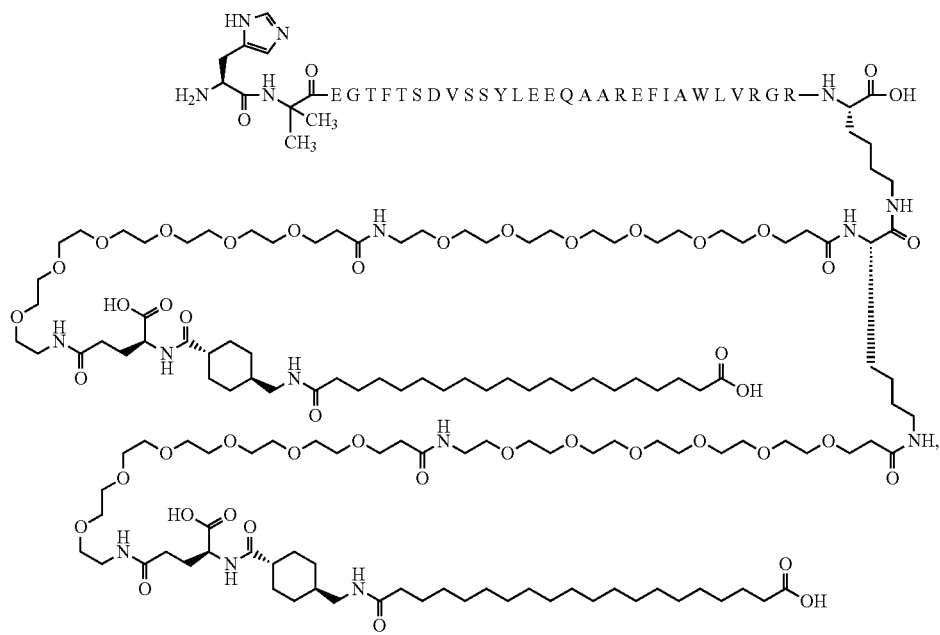
Chem. 43

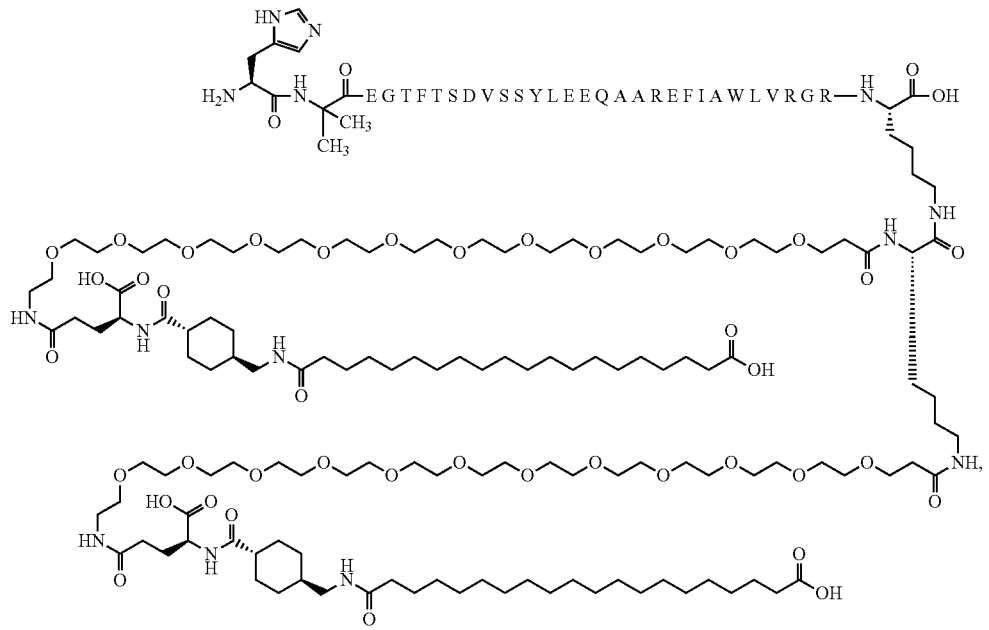
Chem. 44
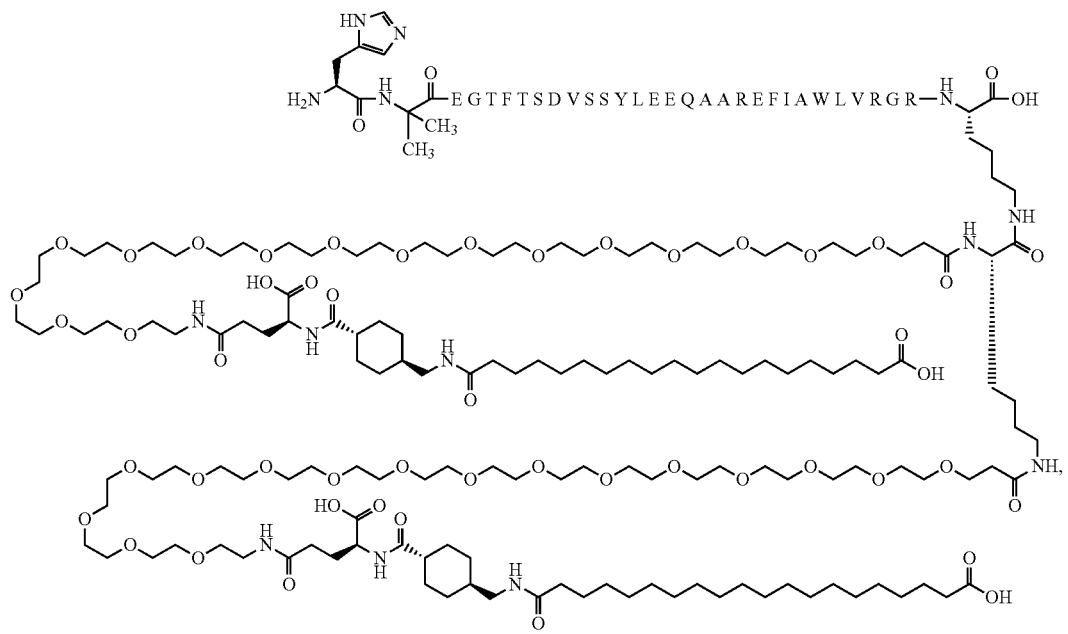
Chem. 45

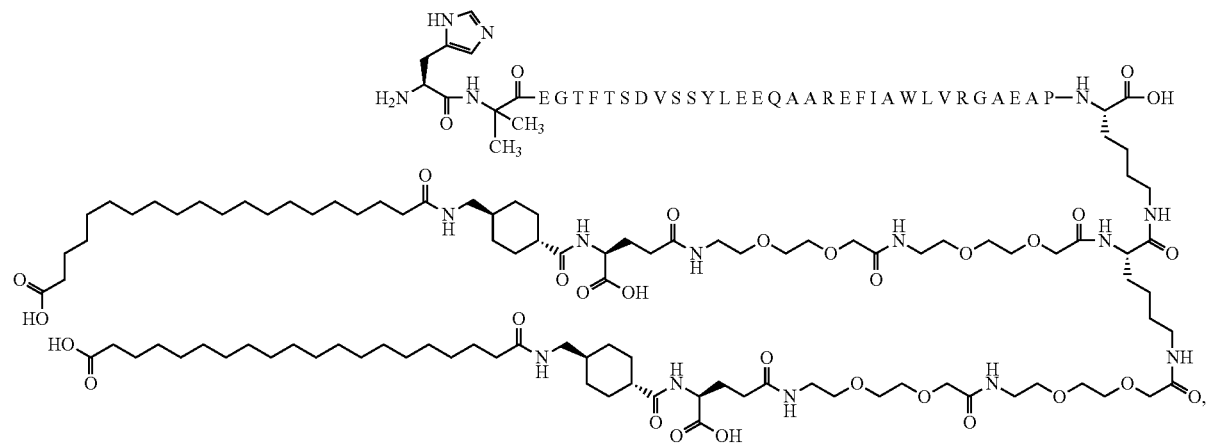
Chem. 46
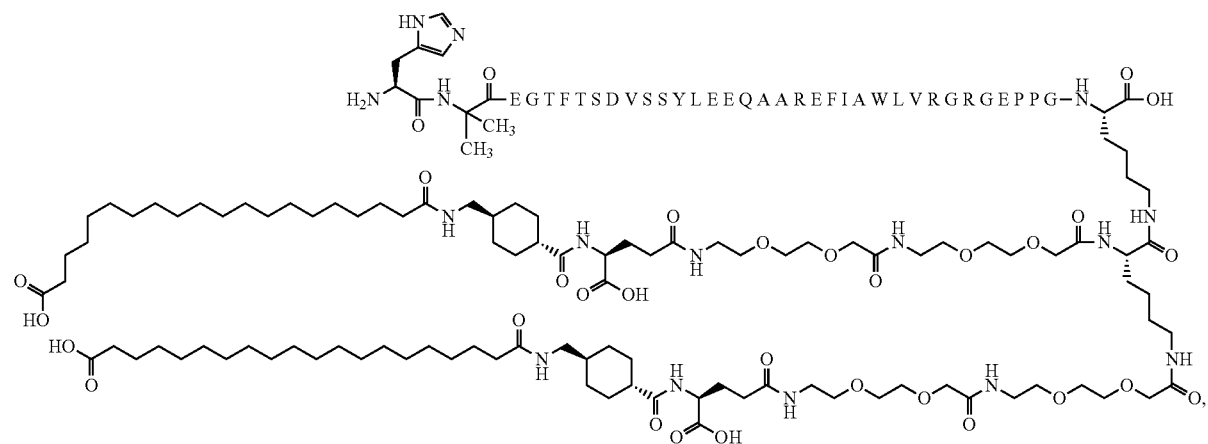
Chem. 47
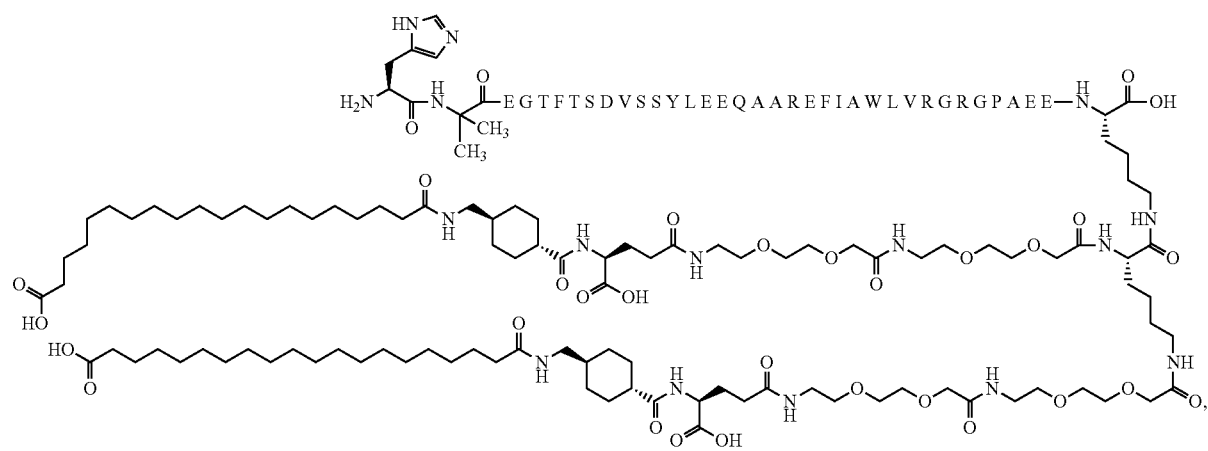
Chem. 48

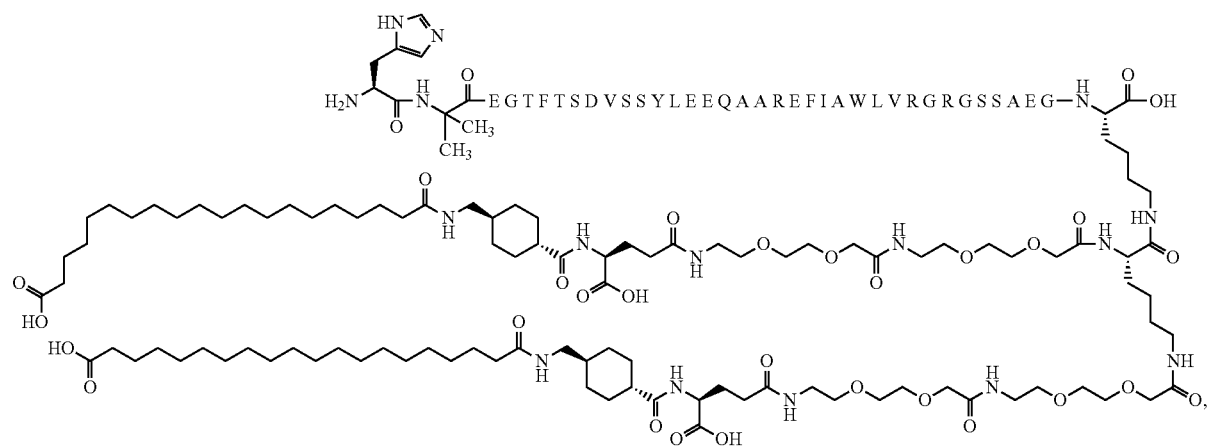
Chem. 50
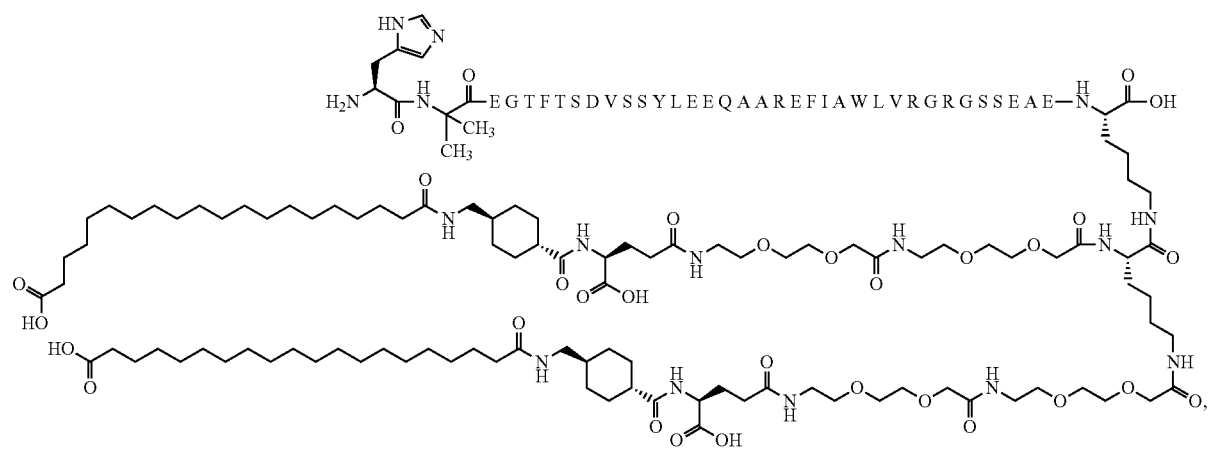
Chem. 51

Chem. 52
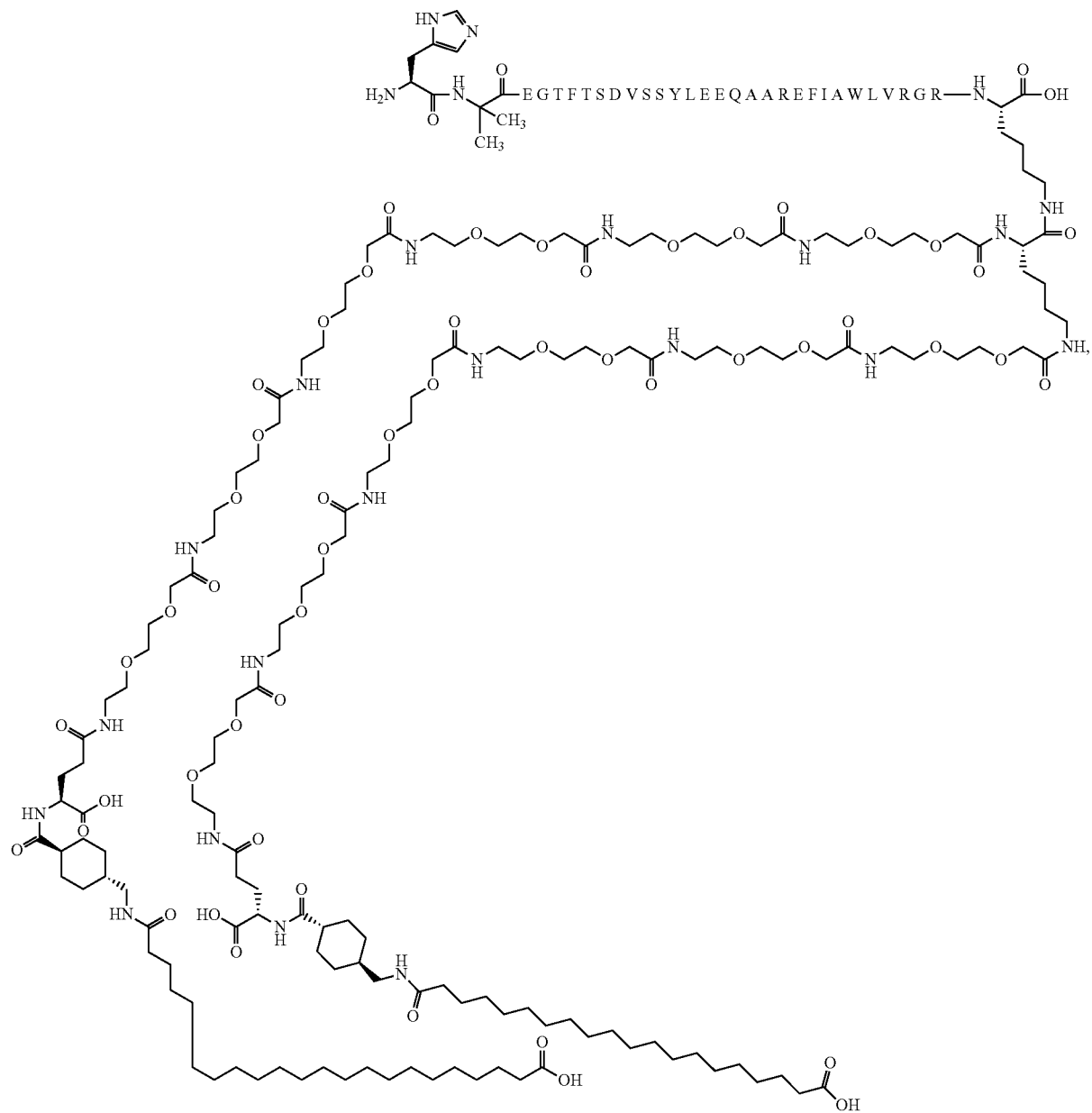

Chem. 53
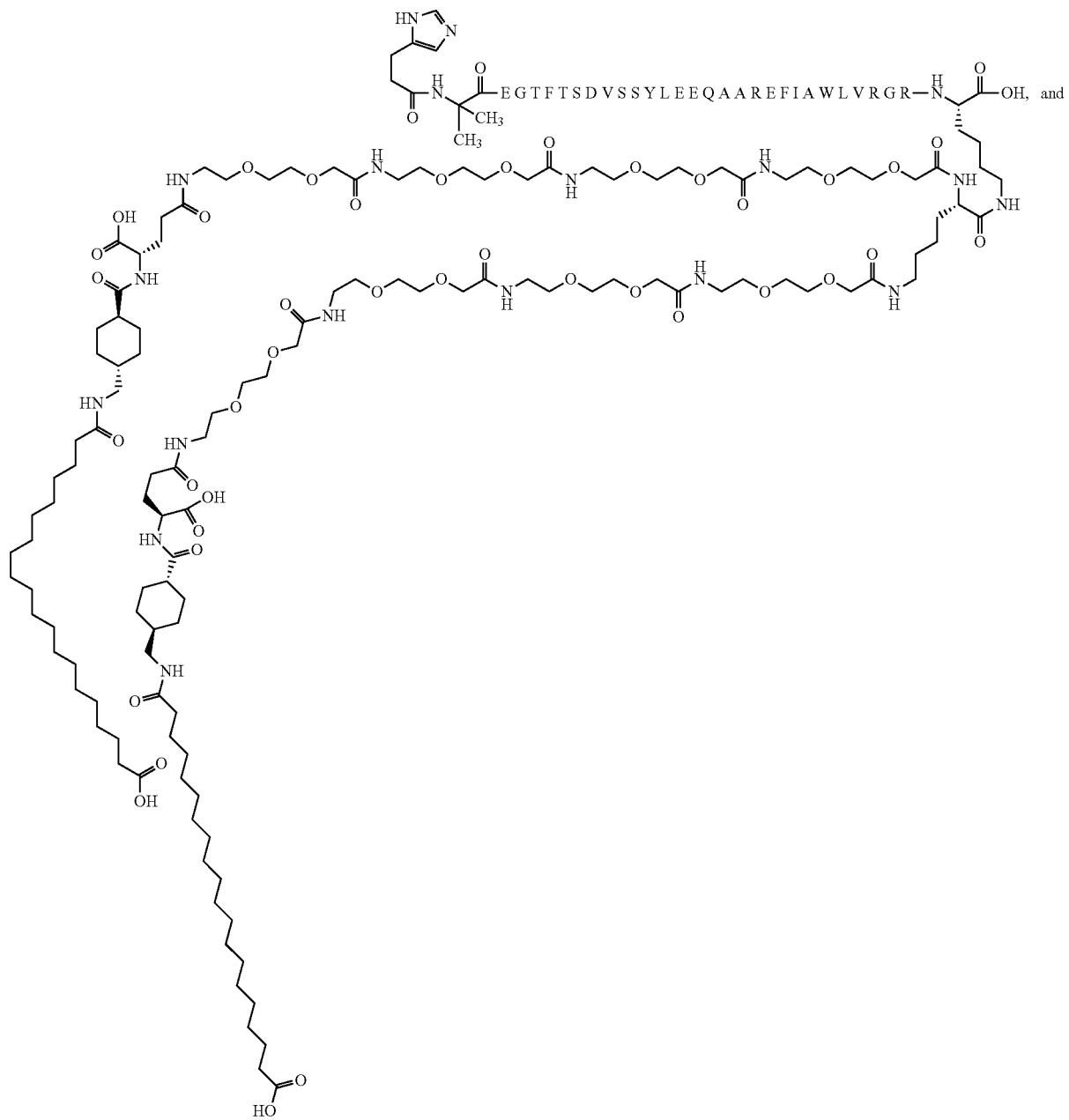

Chem. 54

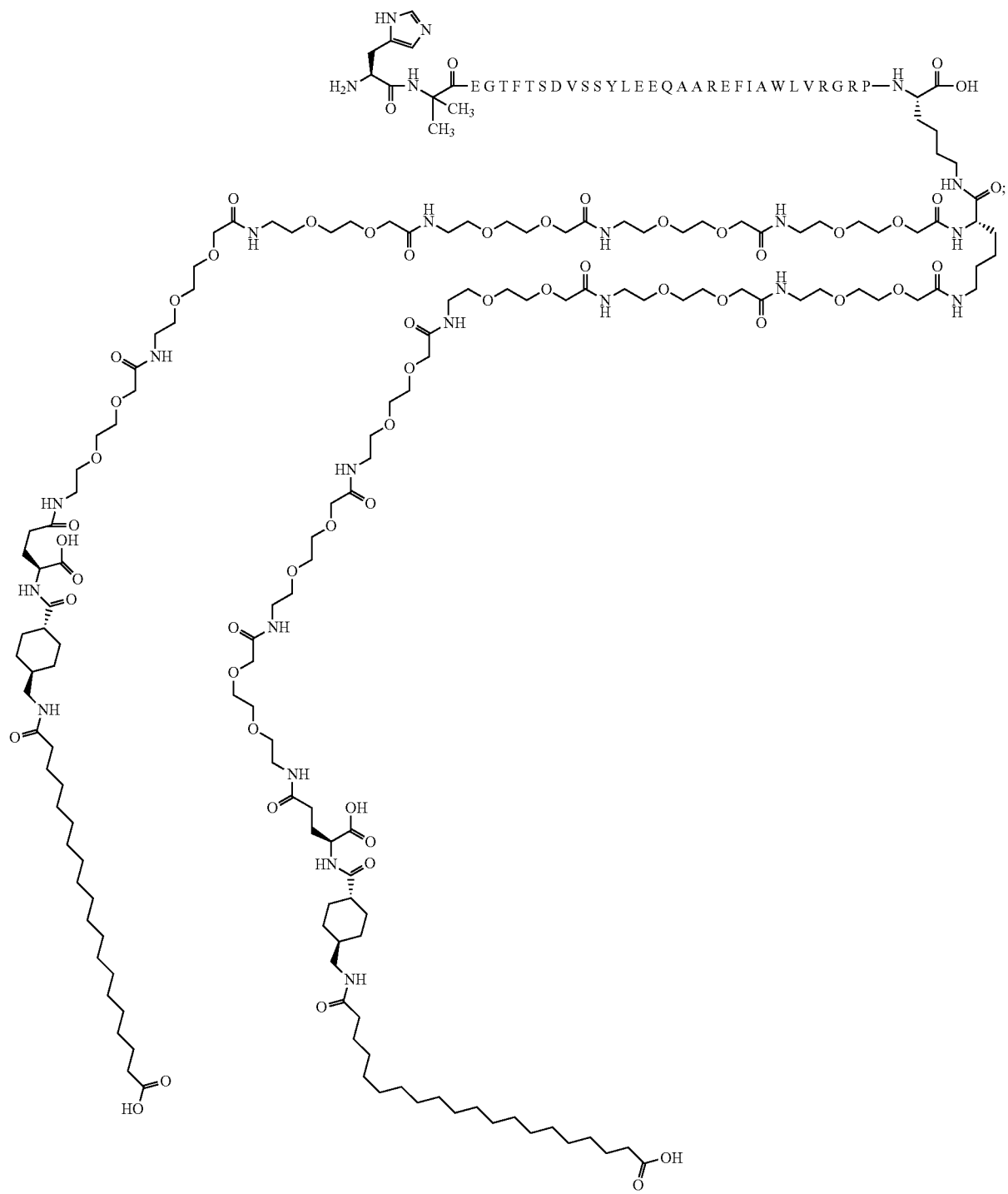

or a pharmaceutically acceptable salt, amide, or ester thereof.

10. A pharmaceutical composition comprising a derivative according to claim 1 and a pharmaceutically acceptable excipient.

11. A method for
treating hyperglycemia, type 2 diabetes, impaired glucose tolerance, type 1 diabetes, non-insulin dependent diabetes, MODY (maturity onset diabetes of the young), and/or gestational diabetes in a subject in need of such treatment;
wherein said method comprises administering to said subject a pharmaceutically active amount of a derivative according to claim 1.

12. A method for
treating hyperglycemia, type 2 diabetes, impaired glucose tolerance, type 1 diabetes, non-insulin dependent diabetes, MODY (maturity onset diabetes of the young), and/or gestational diabetes in a subject in need of such treatment;

wherein said method comprises administering to said subject a pharmaceutically active amount of a derivative according to claim 9.

* * * * *

UNITED STATES PATENT AND TRADEMARK OFFICE
CERTIFICATE OF CORRECTION

PATENT NO. : 10,195,255 B2
APPLICATION NO. : 14/897738
DATED : February 5, 2019
INVENTOR(S) : Steffen Reedtz-Runge et al.

It is certified that error appears in the above-identified patent and that said Letters Patent is hereby corrected as shown below:

In the Claims

At Column 175-176, Claim number 9, after "Chem. 28", please replace the formula with the formula below:

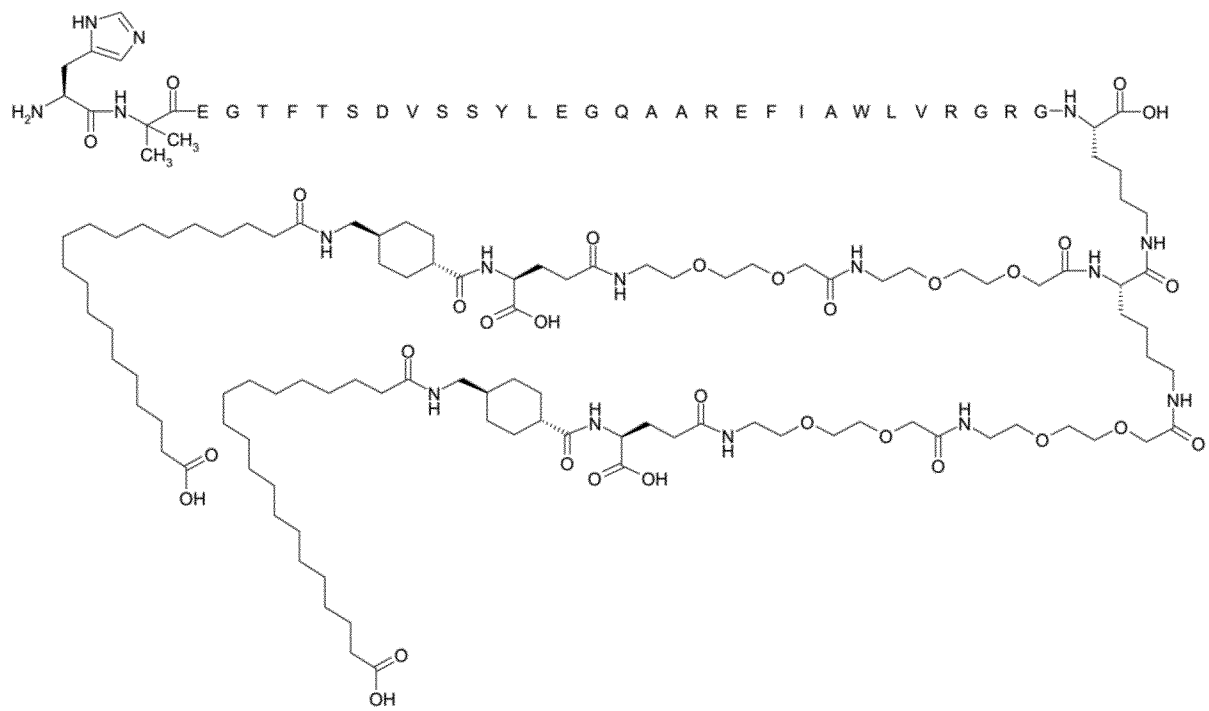

Signed and Sealed this
Sixteenth Day of April, 2019

Andrei Iancu
*Director of the United States Patent and Trademark Office*

CERTIFICATE OF CORRECTION (continued)
U.S. Pat. No. 10,195,255 B2

Page 2 of 2

At Column 185-186, Claim number 9, after "Chem. 38", please replace the formula with the formula below:

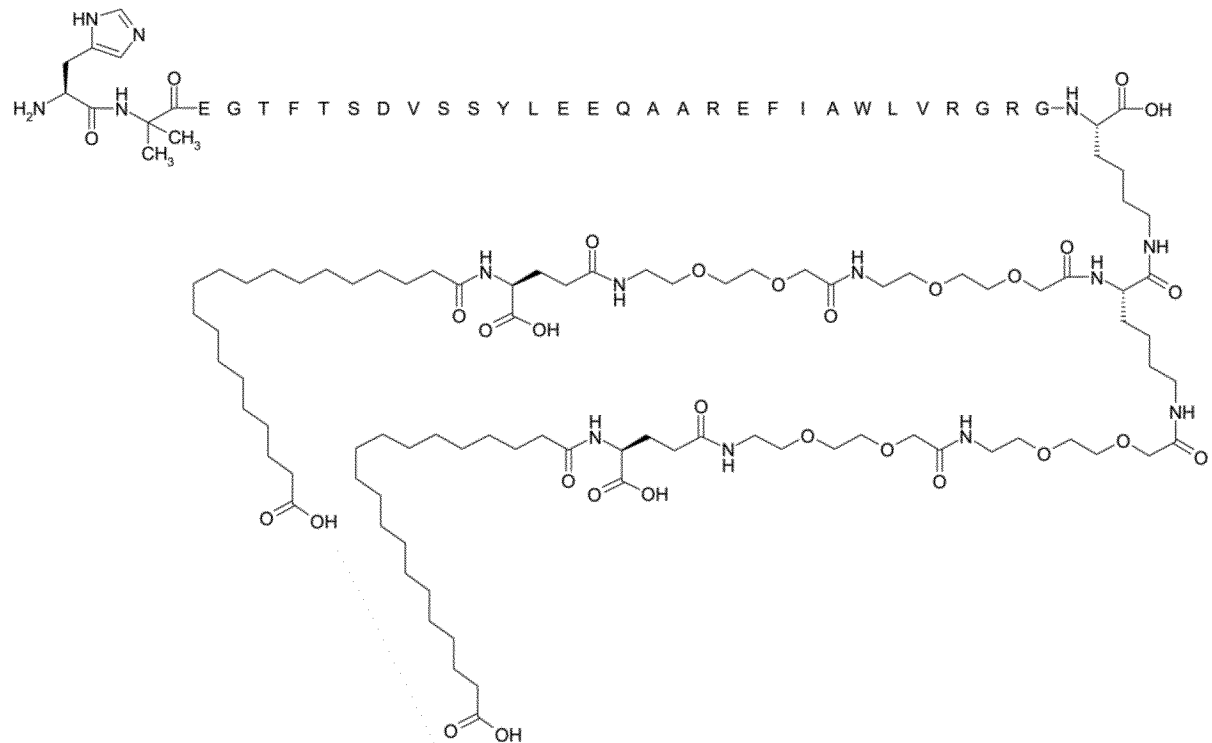

At Column 195-196, Claim number 9, after "Chem. 48" and formula, please insert the following:

--, Chem. 49

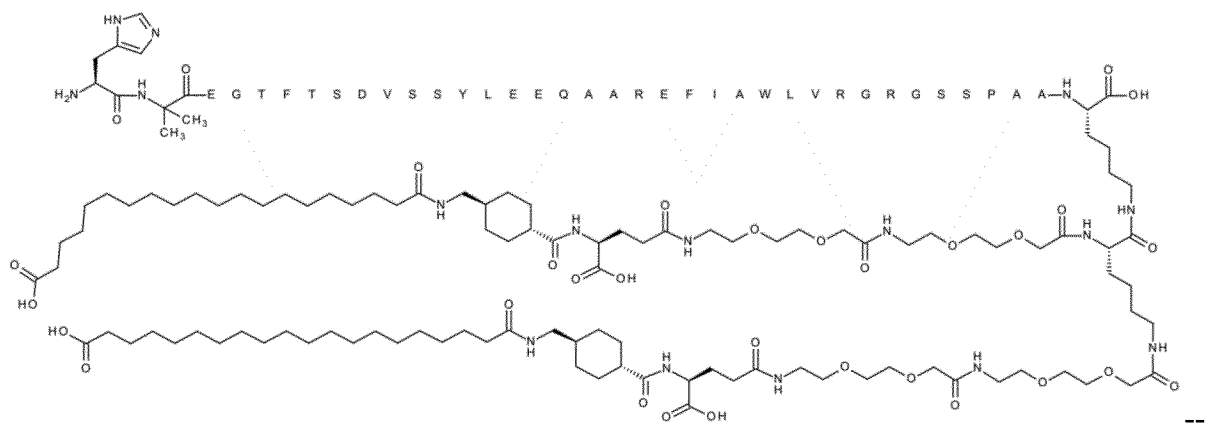

--

SEQUENCE LISTING

```
<160> NUMBER OF SEQ ID NOS: 19

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30

<210> SEQ ID NO 2
<211> LENGTH: 36
<212> TYPE: PRT
<213> ORGANISM: Artificial Sequence
<220> FEATURE:
<223> OTHER INFORMATION: GLP-1 analogue
```

```
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 2

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Gly
            20                  25                  30

Gly Gly Ser Lys
        35

<210> SEQ ID NO 3
<211> LENGTH: 35
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 3

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Gly
            20                  25                  30

Gly Ser Lys
        35

<210> SEQ ID NO 4
<211> LENGTH: 34
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 4

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Gly
            20                  25                  30

Ser Lys

<210> SEQ ID NO 5
<211> LENGTH: 33
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 5

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Ser
```

```
            20                  25                  30
Lys

<210> SEQ ID NO 6
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 6

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Lys
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 7

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Lys
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 8

His Xaa Glu Gly Thr Phe Thr Ser Asp Val Ser Ser Tyr Leu Glu Gly
 1               5                  10                  15

Gln Ala Ala Arg Glu Phe Ile Ala Trp Leu Val Arg Gly Arg Gly Lys
            20                  25                  30

<210> SEQ ID NO 9
<211> LENGTH: 37
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 9

His Xaa Glu Gly Thr Phe Thr Ser Asp Val Ser Ser Tyr Leu Glu Glu
```

```
                1               5                   10                  15
His Xaa Glu Gly Thr Phe Thr Ser Asp Val Ser Ser Tyr Leu Glu Glu
Gln Ala Ala Arg Glu Phe Ile Ala Trp Leu Val Arg Gly Arg Gly Ser
                20                  25                  30
Ser Gly Ala Pro Lys
        35

<210> SEQ ID NO 10
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 10

His Xaa Glu Gly Thr Phe Thr Ser Asp Val Ser Ser Tyr Leu Glu Glu
  1               5                   10                  15
Gln Ala Ala Arg Lys Phe Ile Ala Trp Leu Val Arg Gly Arg Gly
                20                  25                  30

<210> SEQ ID NO 11
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 11

His Xaa Glu Gly Thr Phe Thr Ser Asp Val Ser Ser Tyr Leu Glu Glu
  1               5                   10                  15
Gln Ala Ala Arg Glu Phe Ile Ala Trp Leu Val Arg Gly Arg Gly Ala
                20                  25                  30
Glu Ala Pro Lys
        35

<210> SEQ ID NO 12
<211> LENGTH: 36
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 12

His Xaa Glu Gly Thr Phe Thr Ser Asp Val Ser Ser Tyr Leu Glu Glu
  1               5                   10                  15
Gln Ala Ala Arg Glu Phe Ile Ala Trp Leu Val Arg Gly Arg Gly Glu
                20                  25                  30
Pro Pro Gly Lys
        35

<210> SEQ ID NO 13
<211> LENGTH: 36
<212> TYPE: PRT
<213> ORGANISM: Artificial Sequence
```

```
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 13

His Xaa Glu Gly Thr Phe Thr Ser Asp Val Ser Ser Tyr Leu Glu Glu
  1               5                  10                  15

Gln Ala Ala Arg Glu Phe Ile Ala Trp Leu Val Arg Gly Arg Gly Pro
             20                  25                  30

Ala Glu Glu Lys
         35

<210> SEQ ID NO 14
<211> LENGTH: 37
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 14

His Xaa Glu Gly Thr Phe Thr Ser Asp Val Ser Ser Tyr Leu Glu Glu
  1               5                  10                  15

Gln Ala Ala Arg Glu Phe Ile Ala Trp Leu Val Arg Gly Arg Gly Ser
             20                  25                  30

Ser Pro Ala Ala Lys
         35

<210> SEQ ID NO 15
<211> LENGTH: 37
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 15

His Xaa Glu Gly Thr Phe Thr Ser Asp Val Ser Ser Tyr Leu Glu Glu
  1               5                  10                  15

Gln Ala Ala Arg Glu Phe Ile Ala Trp Leu Val Arg Gly Arg Gly Ser
             20                  25                  30

Ser Ala Glu Gly Lys
         35

<210> SEQ ID NO 16
<211> LENGTH: 37
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 16

His Xaa Glu Gly Thr Phe Thr Ser Asp Val Ser Ser Tyr Leu Glu Glu
```

```
                1               5                   10                  15
Gln Ala Ala Arg Glu Phe Ile Ala Trp Leu Val Arg Gly Arg Gly Ser
                20                  25                  30

Ser Glu Ala Glu Lys
            35
```

<210> SEQ ID NO 17
<211> LENGTH: 33
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (1)..(1)
<223> OTHER INFORMATION: /mod_res= "Imp (3-(Imidazol-5-yl)propanoic acid)"
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 17

```
Xaa Xaa Glu Gly Thr Phe Thr Ser Asp Val Ser Ser Tyr Leu Glu Glu
 1               5                   10                  15

Gln Ala Ala Arg Glu Phe Ile Ala Trp Leu Val Arg Gly Arg Gly Gly
                20                  25                  30

Lys
```

<210> SEQ ID NO 18
<211> LENGTH: 32
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"

<400> SEQUENCE: 18

```
His Xaa Glu Gly Thr Phe Thr Ser Asp Val Ser Ser Tyr Leu Glu Glu
 1               5                   10                  15

Gln Ala Ala Arg Glu Phe Ile Ala Trp Leu Val Arg Gly Arg Pro Lys
                20                  25                  30
```

<210> SEQ ID NO 19
<211> LENGTH: 31
<212> TYPE: PRT
<213> ORGANISM: Artificial Sequence
<220> FEATURE:
<223> OTHER INFORMATION: GLP-1 analogue
<220> FEATURE:
<221> NAME/KEY: Mod_Res
<222> LOCATION: (2)..(2)
<223> OTHER INFORMATION: /mod_res= "Aib (2-Aminoisobutyric acid)"
<220> FEATURE:
<221> NAME/KEY: Mod_Res
<222> LOCATION: (16)..(16)
<223> OTHER INFORMATION: /mod_res= "Aib (2-Aminoisobutyric acid)"
<220> FEATURE:
<221> NAME/KEY: Mod_Res
<222> LOCATION: (29)..(29)
<223> OTHER INFORMATION: /mod_res= "Aib (2-Aminoisobutyric acid)"
<220> FEATURE:
<221> NAME/KEY: Mod_Res
<222> LOCATION: (31)..(31)
<223> OTHER INFORMATION: /mod_res= "Amidation"

```
<400> SEQUENCE: 19

His Xaa Glu Gly Thr Phe Thr Ser Asp Val Ser Ser Tyr Leu Glu Xaa
 1               5                  10                  15

Gln Ala Ala Lys Glu Phe Ile Ala Trp Leu Val Lys Xaa Arg Lys
             20                  25                  30
```